US009115370B2

(12) United States Patent
Lagudah et al.

(10) Patent No.: US 9,115,370 B2
(45) Date of Patent: *Aug. 25, 2015

(54) RESISTANCE GENES

(71) Applicants:Grains Research and Development Corporation, Barton, ACT (AU); Commonwealth Scientific and Industrial Research Organisation, Campbell, ACT (AU); University of Zurich, Zurich (CH)

(72) Inventors: Evans Lagudah, Ngunnawal (AU); Wolfgang Spielmeyer, Gundaroo (AU); Beat Keller, Zurich (CH); Simon Krattinger, Zurich (CH)

(73) Assignees: Grains Research and Development Corporation, Barton (AU); Commonwealth Scientific and Industrial Research Organisation, Campbell (AU); University of Zurich, Zurich (CH)

( * ) Notice: Subject to any disclaimer, the term of this patent is extended or adjusted under 35 U.S.C. 154(b) by 129 days.

This patent is subject to a terminal disclaimer.

(21) Appl. No.: 14/050,058

(22) Filed: Oct. 9, 2013

(65) Prior Publication Data

US 2014/0101791 A1    Apr. 10, 2014

Related U.S. Application Data

(63) Continuation of application No. 13/061,005, filed as application No. PCT/AU2009/001090 on Aug. 25, 2009, now Pat. No. 8,581,038.

(30) Foreign Application Priority Data

Aug. 25, 2008  (AU) .............................. 2008904364

(51) Int. Cl.
  *C12N 15/82*    (2006.01)
  *C12N 5/14*     (2006.01)
  *C12N 15/29*    (2006.01)
  *C07K 14/415*   (2006.01)
  *A01H 5/10*     (2006.01)

(52) U.S. Cl.
  CPC .............. *C12N 15/8282* (2013.01); *A01H 5/10* (2013.01); *C07K 14/415* (2013.01); *C12N 5/14* (2013.01)

(58) Field of Classification Search
  None
  See application file for complete search history.

(56) References Cited

U.S. PATENT DOCUMENTS

| | | |
|---|---|---|
| 4,399,216 A | 8/1983 | Axel et al. |
| 4,945,050 A | 7/1990 | Sanford et al. |
| 5,004,863 A | 4/1991 | Umbeck |
| 5,104,310 A | 4/1992 | Saltin |
| 5,141,131 A | 8/1992 | Miller et al. |
| 5,159,135 A | 10/1992 | Umbeck |
| 5,164,316 A | 11/1992 | McPherson et al. |
| 5,177,010 A | 1/1993 | Goldman et al. |
| 5,384,253 A | 1/1995 | Krzyzek et al. |
| 5,416,011 A | 5/1995 | Hinchee et al. |
| 5,451,513 A | 9/1995 | Maliga et al. |
| 5,459,252 A | 10/1995 | Conkling et al. |
| 5,463,174 A | 10/1995 | Moloney et al. |
| 5,472,869 A | 12/1995 | Krzyzek et al. |
| 5,518,908 A | 5/1996 | Corbin et al. |
| 5,545,818 A | 8/1996 | McBride et al. |
| 5,569,834 A | 10/1996 | Hinchee et al. |
| 5,589,617 A | 12/1996 | Nehra et al. |
| 5,877,402 A | 3/1999 | Maliga et al. |
| 5,932,479 A | 8/1999 | Daniell et al. |
| 6,100,447 A | 8/2000 | Wu et al. |
| 6,541,257 B2 | 4/2003 | Lemaux |
| 8,581,038 B2 | 11/2013 | Lagudah et al. |
| 2004/0123343 A1 | 6/2004 | La Rosa et al. |
| 2006/0123505 A1 | 6/2006 | Kikuchi et al. |
| 2007/0124833 A1 | 5/2007 | Abad et al. |
| 2009/0100536 A1 | 4/2009 | Adams et al. |
| 2011/0223303 A1 | 9/2011 | Lagudah et al. |

FOREIGN PATENT DOCUMENTS

| | | |
|---|---|---|
| AU | 609082 | 4/1991 |
| AU | 610825 | 5/1991 |
| AU | 667939 | 4/1996 |
| CA | 2092588 | 9/1994 |
| EP | 0154204 | 9/1985 |
| WO | WO 8705327 | 9/1987 |
| WO | WO 8706614 | 11/1987 |
| WO | WO 9102071 | 2/1991 |
| WO | WO 9113992 | 9/1991 |
| WO | WO 9209696 | 6/1992 |
| WO | WO 9321335 | 10/1993 |
| WO | WO 9419930 | 9/1994 |
| WO | WO 9748814 | 12/1997 |

(Continued)

OTHER PUBLICATIONS

Eurasian Office Action dated Dec. 19, 2013 for Eurasian Application No. 201170372.

(Continued)

*Primary Examiner* — David T Fox
*Assistant Examiner* — Matthew Keogh
(74) *Attorney, Agent, or Firm* — Carol L. Francis; Bozicevic, Field & Francis LLP

(57) ABSTRACT

The present invention relates to polynucleotides encoding adult plant pathogen resistance proteins. Also provided are transgenic plants expressing these polynucleotides to enhance the resistance of the plants to pathogens.

20 Claims, 9 Drawing Sheets

(56) References Cited

FOREIGN PATENT DOCUMENTS

Figure 1:
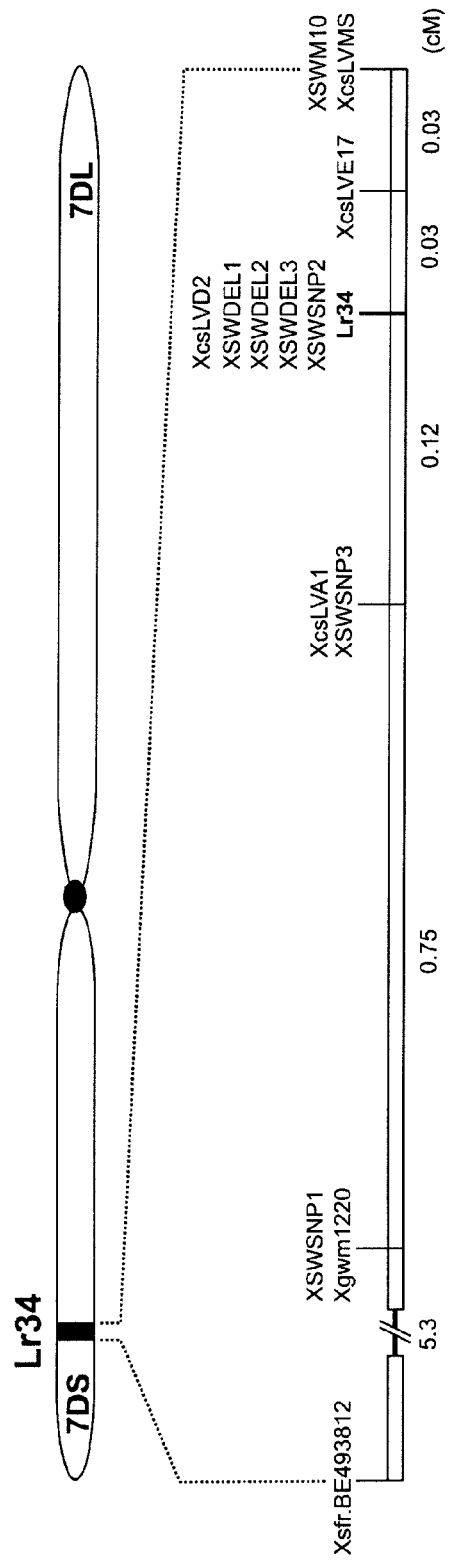

| WO | WO 9905265 | 2/1999 |
|---|---|---|
| WO | WO 9914314 | 3/1999 |
| WO | WO 9938989 | 8/1999 |
| WO | WO 0012736 | 3/2000 |
| WO | WO 0140512 | 6/2001 |
| WO | 2004022715 | 3/2004 |

OTHER PUBLICATIONS

Response to Australian Examiner's Report dated Oct. 21, 2013 for Australian Application No. 2009287411.
Response to Eurasian Office Action dated Feb. 19, 2014 for Eurasian Application No. 201170372.
Ukrainian Office Action dated Oct. 21, 2013 for Ukrainian Application No. 201103544.
Chinese Office Action dated Feb. 7, 2014 for Chinese Application No. CN 200980141964.5.
Chinese Office Action Response filed Jun. 12, 2014 for Chinese Application No. CN 200980141964.5.
Eurasian Office Action, 2014, for Eurasian Application No. 201170372 filed Mar. 24, 2011.
Abdullah et al. (1986) "Efficient Plant Regeneration from Rice Protoplasts through Somatic Embryogenesis" Nat Biotechnology 4:1087-1090.
Altpeter et al. (2005) "Stable Expression of a Defense-Related Gene in Wheat Epidermis under Transcriptional Control of a Novel Promoter Confers Pathogen Resistance" Plant Mo Biol 57(2):271-283.
Australian Examination Report for Australian Application No. 2009287411 dated Sep. 25, 2012.
Baloch (1999) "Wheat: Post-Harvest Operations" Pakistan Agricultural Research Council, p. 1-21.
Bevan et al. (1983) "Structure and transcription of the nopaline synthase gene region of T-DNA" Nucl. Acid Res. 11(2):369-385.
Brueggeman et al. (2002) "The barley stem rust-resistance gene Rpg1 is a novel disease-resistance gene with homology to receptor kinases" Proc. Natl.Acad. Sci. USA 99(14):9328-9333.
Capecchi (1980) "High efficiency transformation by direct microinjection of DNA into cultured mammalian cells" Cell 22(2 Pt 2):479-488.
Cheng et al. (1996) "Production of Fertile Transgenic Peanut (*Arachis hypogaea* L.) plants using *Agrobacterium tumefaciens*" Plant Cell Rep. 15:653-657.
Chinese Office Action for Chinese Application No. 200980141964.5 dated Aug. 30, 2012.
Chinese Office Action Response for Chinese Application No. 200980141964.5 dated Mar. 8, 2013.
Clapp (1993) "Somatic Gene Therapy into Hematopoietic Cells: Current Status and Future Implications" Clin. Perinatol. 20(1):155-168.
Cloutier et al. (2007) "Leaf rust resistance gene Lr1, isolated from bread wheat (*Triticum aestivum* L.) is a member of the large psr567 gene family" Plant Mol. Biol. 65(1-2):93-106.
Collins et al. (1999) "Molecular characterization of the maize Rp1-D rust resistance haplotype and its mutants" Plant Cell 11(7):1365-1376.
Comai et al. (2004) "Efficient discovery of DNA polymorphisms in natural populations by Ecotilling" Plant J 37(5):778-786.
Crouzet et al. (2006) "Organization and function of the plant pleiotropic drug resistance ABA transporter family" FEBS Letters 580(4):1123-1130.
Curiel et al. (1992) "High-efficiency gene transfer mediated by adenovirus coupled to DNA-polylysine complexes" Hum. Gen. Ther. 3(2):147-154.
Dyck & Samborski (1982) "The Inheritance of Resistance to *Puccinia Recondita* in a Group of Common Wheat Cultivars" Can. J. Genet. Cytol. 24: 273-283.
Dyck (1977) "Genetics of Leaf Rust Reaction in Three Introductions of Common Wheat" Can. J. Genet. Cytol. 19:711-716.
Dyck et al. (1966) "Inheritance of Adult-Plant Leaf Rust Resistance Derived from the Common Wheat Varieties Exchange and Frontana" Can. J. Genet.Cytol. 8:665-671.
Dyck et al. (1987) "The Association of a Gene for Leaf Rust Resistance with the Chromosome 7D Suppressor of Stem Rust Resistance in Common Wheat" Genome 29:467-469.
Eglitis & Anderson (1988) "Retroviral vectors for introduction of genes into mammalian cells" Biotechniques 6(7):608-614.
Eurasian Office Action for Eurasian Application No. 201170372 dated Dec. 14, 2012.
European Examination Report for Application No. 09809096.2 dated Jul. 9, 2012.
European Examination Report for Application No. 09809096.2 dated May 2, 2013.
European Examination Report Response for Application No. 09809096.2 dated May 28, 2012.
European Examination Report Response for Application No. 09809096.2 dated Nov. 19, 2012.
European Extended Supplementary Search Report for Application No. 09809096.2 dated Oct. 19, 2012.
Feuillet et al. (2003) "Map-based isolation of the leaf rust disease resistance gene Lr10 from the hexaploid wheat (*Triticum aestivum* L.) genome" Proc. Natl. Acad. Sci. 100(25):15253-15258.
Fujimura et al. (1985) "Regeneration of Rice Plants from Protoplasts" Plant Tissue Cultural Letters 2(2):74-75.
GenBank Accession No. ACL36480, Jan. 13, 2009 "PDR-like ABC transporter [*Aegilops tauschii*]".
GenBank Accession No. ACN41354, Mar. 4, 2009 "LR34 [*Triticum aestivum*]".
GenBank Accession No. AK102367, Jul. 18, 2003 "*Oryza sativa* Japonica Group cDNA clone:J033091K10, full insert sequence".
GenBank Accession No. AK103110, Jul. 18, 2003 "*Oryza sativa* Japonica Group cDNA clone:J033119C07, full insert sequence".
GenBank Accession No. BU991506 "HD07C03r HD *Hordeum vulgare* cDNA clone HD07C03 5-PRIME, mRNA sequence" dated Jan. 29, 2009.
GenBank Accession No. CAD59575 "PDR-like ABC transporter [*Oryza sativa* Japonica Group]" dated Nov. 14, 2006.
GenBank Accession No. CAH39853 "PDR-like ABC trasporter [*Nicotiana tabacum*]" dated Dec. 13, 2005.
GenBank Accession No. CAN65735 "hypothetical protein VITISV_03775 [*Vitis vinifera*]" dated Feb. 5, 2008.
GenBank Accession No. CJ562397 "CJ562397 Y.Ogihara unpublished cDNA library Wh_KMV *Triticum aestivum* cDNA clone rwhkv19d01 3-, mRNA sequence" dated Feb. 23, 2011.
GenBank Accession No. CJ669561 "CJ669561 Y.Ogihara unpublished cDNA library Wh_KMV *Triticum aestivum* cDNA clone whkv19d01 5-, mRNA. sequence" dated Feb. 23, 2013.
GenBank Accession No. CV773074 "FGAS067470 *Triticum aestivum* FGAS: Library 2 Gate 3 *Triticum aestivum* cDNA, mRNA sequence" dated Nov. 10, 2004.
GenBank Accession No. DAA00881 "TPA_exp: PDR13 ABC transporter [*Arabidopsis thaliana*]" dated Feb. 3, 2006.
GenBank Accession No. DR733734 "FGAS079492 *Triticum aestivum* FGAS. Library 2 Gate 3 *Triticum aestivum* cDNA, mRNA sequence" dated Jul. 18, 2005.
GenBank Accession No. EAY83289 "hypothetical protein OsI_037248 [*Oryza saliva* (indica cultivar-group)]" dated Feb. 9, 2007.
GenBank Accession No. EAZ20654 "hypothetical protein OsJ_034863 [*Oryza saliva* (japonica cultivar-group)]" dated Feb. 12, 2007.
GenBank Accession No. NM_001073407, Oct. 2, 2006 *Oryza sativa Japonica* Group Os12g0512700 (Os12g0512700) mRNA, partial cds.
GenBank Accession No. NP_176196 "ABC transporter G family member 36 [*Arabidopsis thaliana*]" dated May 28, 2011.
GenBank Accession No. NP_181265, Aug. 13, 2001 "ABC transporter G family member 33 [*Arabidopsis thaliana*]".
GenBank Accession No. NP_190916, Aug. 13, 2001 "ABC transporter G family member 37 [*Arabidopsis thaliana*]".

(56) References Cited

OTHER PUBLICATIONS

GenBank Accession No. Q5W274, Feb. 1, 2005 "RecName: Full=Pleiotropic drug resistance protein 3; AltName: Full=NtPDR3".
German & Kolmer (1992) "Effect of Gene *Lr34* in the Enhancement of Resistance to Leaf Rust of Wheat" Theor. Appl. Genet. 84:97-105.
Gotor et al. (1993) "Analysis of three tissue-specific elements from the wheat Cab-1 enhancer" Plant J. 3(4):509-518.
Graham & Van Der Eb (1973) "Transformation of rat cells by DNA of human adenovirus 5" Virology 54(2):536-539.
Grant et al. (1995) "Transformation of Peas (*Pisum Sativum* L.) Using Immature Cotyledons" Plant Cell Rep. 15:254-258.
Harayama (1998) "Artificial evolution by DNA shuffling" Trends Biotechnol. 16(2):76-82.
Henikoff et al. (2004) "TILLING. Traditional mutagenesis meets functional genomics" Plant Physiol 135(2):630-636.
Huang et al. (2003) "Map-based cloning of leaf rust resistance gene Lr21 from the large and polyploid genome of bread wheat" Genetics 164(2):655-664.
Joshi (1987) "An inspection of the domain between putative TATA box and translation start site in 79 plant genes" Nucleic. Acid Res. 15(16): 6643-6653.
Joshi et al. (2004) "Leaf Tip Necrosis: A Phenotypic Marker Associated with Resistance to Spot Blotch Disease in Wheat" Crop Science 44:792-796.
Kim, et al. (2006) "AtATM3 is Involved in Heavy Metal Resistance in *Arabidopis*" Plant Physiol. 140(3):922-932.
Kolmer et al. (2003) "Physiologic Specialization of *Puccinia triticina* on Wheat in the United States in 2001" Plant Disease 87:859-866.
Kolmer et al. (2008) "Analysis of the *Lr34/Yr18* Rust Resistance Region in Wheat Germplasm" Crop Science 48:1037-1047.
Krattinger et al. (2009) "A putative ABC transporter confers durable resistance to multiple fungal pathogens in wheat" *Science* 323:1360-1363.
Krupinska et al. (2002) "A novel nucleus-targeted protein is expressed in barley leaves during senescence and pathogen infection" Plant Physiol. 130(3):1172-1180.
Kwon et al. (1994) "Identification of a light-responsive region of the nuclear gene encoding the B subunit of chloroplast glyceraldehyde 3-phosphate dehydrogenase from *Arabidopsis thaliana*" Plant Physiol. 105(1):357-367.
Lagudah et al. (2006) "Molecular genetic characterization of the Lr34/Yr18 slow rusting resistance gene region in wheat" Theor. Appl. Genet. 114(1):21-30.
Langridge et al. (2001) "Trends in Genetic and Genome Analysis in Wheat: A Review" Aust. J. Agric. Res. 52:1043-1077.
Lemieux (2000) "High Throughput Single Nucleotide Polymorphism Genotyping Technology" Current Genomics 1(4):301-311.
Liang et al. (2006) "Quantitative trait Loci mapping for adult-plant resistance to powdery mildew in bread wheat" Phytopathology 96(7):784-789.
Lu et al. (1993) "High efficiency retroviral mediated gene transduction into single isolated immature and replatable CD34(3+) hematopoietic stem/progenitor cells from human umbilical cord blood" J. Exp. Med. 178(6):2089-2096.
Matsuoka et al. (1993) "Tissue-specific light-regulated expression directed by the promoter of a C4 gene, maize pyruvate,orthophosphate dikinase, in a C3 plant, rice" Proc. Natl. Acad. Sci. USA 90(20):9586-9590.
McIntosh (1992) "Close Genetic Linkage of Genes Conferring Adult-Plant Resistance to Leaf Rust and Stripe Rust in Wheat" Plant Pathol. 41:523-527.
Medberry & Olszewski (1993) "Identification of cis elements involved in Commelina yellow mottle virus promoter activity" Plant J. 3(4):619-626.
Medberry et al. (1992) "The Commelina yellow mottle virus promoter is a strong promoter in vascular and reproductive tissues" Plant Cell 4(2):185-192.

Needleman & Wunsch (1970) "A general method applicable to the search for similarities in the amino acid sequence of two proteins" J. Mol Biol. 48(3):443-453.
Oldach et al. (2001) "Heterologous Expression of Genes Mediating Enhanced Fungal Resistance in Transgenic Wheat" *Mol Plant Microbe Interact* 14(7):832-838.
Orozco & Ogren (1993) "Localization of light-inducible and tissue-specific regions of the spinach ribulose bisphosphate carboxylase/oxygenase (rubisco) activase promoter in transgenic tobacco plants" Plant Mol. Biol. 23(6):1129-1138.
Ow et al. (1986) "Transient and stable expression of the firefly luciferase gene in plant cells and transgenic plants" Science 234(4778):856-859.
Pellegrineschi et al. (2002) "Identification of highly transformable wheat genotypes for mass production of fertile transgenic plants" Genome 45(2):421-430.
Rae (2007) "Plant ATP-binding cassette transporters" Annu. Rev. Plant Biol. 58:347-375.
Rogers et al (2001) "The pleitropic drug ABC transporters from *Saccharomyces cerevisiae*" J. Mol. Microbiol. Biotechnol. 3: 207-214.
Rubiales & Niks (1995) "Characterization of *Lr34*, a Major Gene Conferring Nonhypersensitive Resistance to Wheat Leaf Rust" Plant Dis. 79(12):1208-1212.
Salomon et al. (1984) "Genetic identification of functions of TR-DNA transcripts in octopine crown galls" EMBO J. 3: 141-146.
Schunmann et al. (2003) "A Suite of Novel Promoters and Terminators for Plant Biotechnology. II. The pPLEX Series for Use in Monocots" Functional Plant Biology 30:453-460.
Singh & Rajaram (1994) "Genetics of Adult Plant Resistance to Stripe Rust in Ten Spring Bread Wheats" Euphytica 72:1-7.
Singh (1992) "Association between Gene *Lr34* for Leaf Rust Resistance and Leaf Tip Necrosis in Wheat" Crop Science 32: 874-878.
Singh (1992) "Genetic Association of Leaf Rust Resistance Gene Lr34 with Adult Plant Resistance to Stripe Rust in Bread Wheat" Phytopathology 82(8):835-838.
Slade & Knauf (2005) "TILLING moves beyond functional genomics into crop improvement" Transgenic Res. 14(2):109-115.
Spielmeyer et al. (2005) "Powdery mildew resistance and Lr34/Yr18 genes for durable resistance to leaf and stripe rust cosegregate at a locus on the short arm of chromosome 7D of wheat" Theor. Appl. Genet. 111(4):731-735.
Spielmeyer et al. (2008) "Fine scale genetic and physical mapping using interstitial deletion mutants of Lr34 /Yr18: a disease resistance locus effective against multiple pathogens in wheat" Theor Appl Genetics 116(4):481-490.
Stein et al. (2006) "*Arabidopsis* PEN3/PDR8, an ATP binding cassette transporter, contributes to nonhost resistance to inappropriate pathogens that enter by direct penetration" The Plant Cell 18(3):731-746.
Stockhaus et al. (1987) "Analysis of cis-active sequences involved in the leaf-specific expression of a potato gene in transgenic plants" Proc. Natl. Acad. Sci. USA 84(22):7943-7947.
Stockhaus et al. (1989) "Correlation of the expression of the nuclear photosynthetic gene ST-LS1 with the presence of chloroplasts" EMBO J. 8(9):2445-2451.
Sugiyama, et al. (2007) "Involvement of a Soybean ATP-binding Cassette-type Transporter in the Secretion of Genistein, a Signal Flavonoid in Legume-Rhizobium Symbiosis" *Plant Physiol.* 144(4):2000-2008.
Thillet et al. (1988) "Site-directed mutagenesis of mouse dihydrofolate reductase. Mutants with increased resistance to methotrexate and trimethoprim" J. Biol. Chem. 263(25):12500-12508.
Toriyama et al. (1986) "Haploid and Diploid Plant Regeneration from Protoplasts of Anther Callus in Rice" Theor. Appl. Genet. 73:16-19.
Van Den Brule & Smart (2002) "The plant PDR family of ABC transporters" Planta 216(1):95-106.
Verrier et al. (2007) "Plant ABC proteins—a unified nomenclature and updated inventory" Trends Plant Sci. 13(4):151-159.

(56) References Cited

OTHER PUBLICATIONS

Wagner et al. (1992) "Coupling of adenovirus to transferrin-polylysine/DNA complexes greatly enhances receptor-mediated gene delivery and expression of transfected genes" Proc. Natl. Acad. Sci. USA 89(13):6099-6103.

Yamamoto et al. (1997) "Light-responsive elements of the tobacco PSI-D gene are located both upstream and within the transcribed region" Plant J. 12(2):255-265.

Australian Examination Report Response filed Oct. 21, 2013 for Australian Application No. AU 2009287411.

Chinese Office Action dated Jul. 12, 2013 for Chinese Application No. CN 200980141964.5.

Chinese Office Action Response filed Sep. 27, 2013 for Chinese Application No. CN 200980141964.5.

Eurasian Office Action Response filed Jun. 3, 2013 for Eurasian Application No. EA 201170372.

European Examination Report Response filed Jun. 27, 2013 for European Application No. EP 09809096.2.

MEGLARETNPSSHHQDFTACASDERPDESELELASRQRQNGAANTEHVSENMLLDSSKLGALKRREFFD
NLLKNLEDDHLRFLRGQKERIDRVDVKLPAIEVRYNNLFVEAECRVTKGNHLPSLWNSTKGAFSGLVKL
LGFETERAKTNVLEDVSGIIKPCRLTLLLGPPGCGKSTLLRALAGKLDKSLKVTGDISYNGYELHEFVP
EKTAVYINQHDLHIAEMTVRETLDFSAQCQGVGRRPKILKEVNTRESVAGIIPDADIDLYMKVVAVEAS
ERSLQTDYILKIMGLEICADTMVGDAMRRG▓▓▓▓▓▓▓▓▓▓▓▓EMIVGPASAYFMDEISNGLDSSTTFQI
INCFQQLTNISEYTMVISLLQPTPEVFDLFDDLILMAEGKIIYHGPRNEALNFFEECGFICPERKAAAD
FLQEILSWKDQQQYWLGPHESYRYISPHELSSMFRENHRGRKLHEQSVPPKSQLGKEALAFNKYSLQKL
EMFKACGAREALLMKRNMFVYVFKTGQLAIIALVTMSVFLRTRMTISFTHANYYMGALFFSI▓MIMLNG
IPEMSMQIGRLPSFYKQKSYYFYSSWAYAIPASVLKVPISILDSLVWISITYYGIGYTPTVSRFFCQFL
ILCLLHHSVTSQ▓RFIASYFQTPIVSFFYLFLALTVFLTFGGFILPKTSMPGWLNWGFWISPMTYAEIS
IVINEFLAPRWQKESIQNITIGNQILVNHGLYYSWHYYWISFGALLGSILLFYIAFGLALDYRTPTEEY
HGSRPTKSLCQQQEKDYTIQNESDDQSNISKAKVTIPVMHLPITFHNLNYYIDTPPEMLKQGYPTRRLR
LLNNITGALRPGVLSALMGVSGAGKTTLLDVLAGRKTGGYIEGDIRIGGYPKVQETFVRILGYCEQVDI
HSPQLTVEESVTYSAWLRLPSHVDEQTRSKFVAEVLETVELDQIKDVLVGSPQKNG▓▓▓▓▓▓▓▓▓▓▓V
ELVSNPSIILMDEPTTGLDTRSAAIVIRAVKNICETGRTVVCTIHQPSTEIFEAFDELILMKSGGKTIY
SGPIGERSCKVIEYFEKISGVPKIKSNCNPATWMMDVTSTSMEVQHNMDFAILYEESSLHREAEDLVEQ
LSIPLPNSENLCFSHSFAQNGWIQLKACLWKQNITYWRSPQYNLRRIMMTVISALIYGILFWKHAKVLN
NEQDMLSVFGAMYLGFTTIGAYNDQTIIPFSTTERIVMYRERFAGMYSSWSYSFAQAFIEIPYVFIQVV
LYTLIVYPSTGYYWTAHKFLWFFYTTFCSILSYVYVGLLLVSITPNVQVATILASFFNTMQTLFSGFIL
PAPQIPKWWTWLYYLTPTSWALNALLTSQYGNIEKEVKAFGETKSVSIFLNDYFGFHQDKLSVVAAVLV
AFPFVLIILFSLSIEKLNFQKR*

Figure 4

Figure 6

```
                   ******   ..:: *: ,** :****:**:,*** *** . .*** ******:,*****,***:*,*********:*:*
Lr34_Renan  YSAWLRLPSHVDEQTRSKFVAEVLETVELDQIKDVLVGSPQKNGLSMEQRKRLTIAVELVSNPSIILMDEPTTGLDTRSA   989
Os_PDR23    YSAWLRLPSHVDKKTRSEVVAEVLETVELDQIKDVLVGTPQKNGLSMEQRKRLTIAVELVSNPSVILMDEPTTGLDTRSA   993
At_PDR5     YSAWLRLVPEINPQTKIRFVKQVLETIELEEIIDALVGVAGVSGLSTEQRKRLTVAVELVANPSIIFMDEPTTGLDARAA  1000
At_PDR9     YSAWLRLAPEIDATTKTKFVKQVLETIELDEIKDSLVGVTGVSGLSTEQRKRLTIAVELVANPSIIFMDEPTTGLDARAA  1037

***:******:..****:********  .*********:*:* **: **.**:*::*  :****:.:. : *::.: ***:**
Lr34_Renan  ATVIRAVENICETGRTVVCTIHQPSTEIFEAFDELILMKSGGKTISGEIGERSCKVIEYPEKISGVPKIKSNCNPATWM  1069
Os_PDR23    ATVIRAVENICKTGRTVVCTIHQPSTKIFEAFDELILMKNGGKIIINGEIGERSSKVIEYFEKISGVLKVKSNCNPAAWM  1073
At_PDR5     ATVMRAVKNVAETGRTIVCTIHQPSIHIFEAVDELVLLKRGGRMISGPLGQHSSCVIEYFQNIPGVAKIRDKYNPATWM  1080
At_PDR9     ATVMRAVKNVADTFGRTIVCTIHQPSIDIFEAVDELVILKRGGRMIYGPLGQHSRHILEYFESVPEIPKIKDNENPATWM  1117

:.*:* *.* : .:*** .*:.*   ::  :**.:** * .*. : *.: *.:.  * *::: ***  .::******.***
Lr34_Renan  MDVTSTSMEVQHNMDPAILVEESSLHREAEDLVEQLSIDLPNGENLCFSHSFAQNGWIQLKACLWKQNITVWRSPQYNLR  1149
Os_PDR23    MDVTSTSMEVQHNMDPAILVDESSQHRDIVELVEKLSIIPNSEILSFSHRVPRNGWIQLKACLWKQNLTVWRSPEVNLR  1153
At_PDR5     LEVTSESVETELDMDFAKIYNESDLYKNNSELVKELSKPDHGSSDLHFKRTFAQNWWEQFKSCLWKMSLSYWRSPSINLM  1160
At_PDR9     LDVSSQSVEIELGVDPAKIYHDSALYKRNSELVKQLSQPDSGSSDIQKKRTPAQSWWGQFKSILWKMNLSYWRSPSINLM  1197

*:  *.:*::::*  ***::.:  ::  :*.::.*:**:*      :*  *  :  :  :  *** *****:*******: :*::.*
Lr34_Renan  RINMMTVISALIYGILPWKHAKVLNNESDMLSVFGAMYLGFTTIGAYNDQTIIPFSTTERIVMYRERVAGMYSSWSYSFAQ  1229
Os_PDR23    RIMLTVISALVYGVLPWKRAKILNDEQDLFNVFGAMYLGSTTIGSYNHQSIIPFSTVERIVMYREKFAGMYSSWSYSFAQ  1233
At_PDR5     RIGHIFLSSFIFGLLPWNQGKKIDTQQNLFTVLGAIYGLVLFVGINNCTSALQYPETERNVMYRERFAGMYSAFAYALAQ  1240
At_PDR9     RMMHLLVSSLIFGALPWKQGQNLDTQQSMFTVFGAIYGLVLFLGINNCASALQYFETERNVMYRERFAGMYSATAYALGQ  1277

. ****:***  . :.:: ** *:* :  *.:*  :*:  **. *  :  *:.::*:*.***.  **:**  *:*  . ..:*:**
Lr34_Renan  AFIEIPYVFIQVVLYTLIVVFSTNYYWTAHKFLWFFYTTFCSILSYVVGLLLVSIFPNVQVATILASFFNTMQTLFSGF  1309
Os_PDR23    AAIKIPYVFIQVVLYTLIIVPSIGYYWTTHKFIWFFYTTPCSSLSYIYVGLLLVSLFPNVQVATILASFFNTMQTLFSGF  1313
At_PDR5     VVTEIPYIFIQSAEFVIVIVPMIGFVASPSKVFWSLVAMFGNLLCFNVLAMPFISIFPNFMVAAILQSLFFTTFNIFAGF  1320
At_PDR9     VVTEIPYIFLQAAEFVIVTVPMIGFVPSAYKVFWSLYSMPCSLLTPNYLAMPFLVSIFPNFMVAAILQSLFYVGFNLFSGF  1357

:: * .*.:* ** *:**:******:*:  ::::*****:*..:::..**::.:*: **:*******:* * :.* : :****..*  :
Lr34_Renan  ILRAPQIRKWWTNLFYLTPTEWALNALLTSGYGNIEKEVKAFGETKSVSIFLNDYFGFHQDKLSVVAAVLVAFPFVLIIL  1389
Os_PDR23    ILRAPQIRKWWVHLFYLTPTSWTLDALLTSGYGNIEKEVRAFGETKSVSIFLNDYFGFHKDKLSLVAAVLIAFPFVLIIL  1393
At_PDR5     LIEKPQIRKWWVNFFYIILPISWTLNLFFSSQYGDIHQKINAFGETKTVASFLEDYFGFHHDRLMITAIILIAFFIALATM  1400
At_PDR9     LIEQTQVPGWWINLYYLLPTSWTLNGFISSQYGDIHEEINVFGQSTTVARFLKDYFGFHHDLLAVTAVVQIAFFIALASM  1437

::: : *:****:*
Lr34_Renan  FSLSIEKLNFQKR-  1402
Os_PDR23    FSFSIEKFNFQKR-  1406
At_PDR5     YAPFVAKLNFQKR-  1413
At_PDR9     FAFFVGKLNFQRR-  1450
```

Figure 6 (continued)

SEQUENCE LISTING

```
<160> NUMBER OF SEQ ID NOS: 64

<210> SEQ ID NO 1
<211> LENGTH: 1401
<212> TYPE: PRT
<213> ORGANISM: Triticum aestivum cv Chinese Spring

<400> SEQUENCE: 1
```

Met Glu Gly Leu Ala Arg Glu Thr Asn Pro Ser Ser His His Gln Asp
1               5                   10                  15

Phe Thr Ala Cys Ala Ser Asp Glu Arg Pro Asp Glu Ser Glu Leu Glu
            20                  25                  30

Leu Ala Ser Arg Gln Arg Gln Asn Gly Ala Ala Asn Thr Glu His Val
        35                  40                  45

Ser Glu Asn Met Leu Leu Asp Ser Ser Lys Leu Gly Ala Leu Lys Arg
    50                  55                  60

Arg Glu Phe Phe Asp Asn Leu Leu Lys Asn Leu Glu Asp Asp His Leu
65                  70                  75                  80

Arg Phe Leu Arg Gly Gln Lys Glu Arg Ile Asp Arg Val Asp Val Lys
                85                  90                  95

Leu Pro Ala Ile Glu Val Arg Tyr Asn Asn Leu Phe Val Glu Ala Glu
            100                 105                 110

Cys Arg Val Thr Lys Gly Asn His Leu Pro Ser Leu Trp Asn Ser Thr
        115                 120                 125

Lys Gly Ala Phe Ser Gly Leu Val Lys Leu Leu Gly Phe Glu Thr Glu
    130                 135                 140

Arg Ala Lys Thr Asn Val Leu Glu Asp Val Ser Gly Ile Ile Lys Pro
145                 150                 155                 160

Cys Arg Leu Thr Leu Leu Leu Gly Pro Pro Gly Cys Gly Lys Ser Thr
                165                 170                 175

Leu Leu Arg Ala Leu Ala Gly Lys Leu Asp Lys Ser Leu Lys Val Thr
            180                 185                 190

-continued

```
Gly Asp Ile Ser Tyr Asn Gly Tyr Glu Leu His Glu Phe Val Pro Glu
            195                 200                 205
Lys Thr Ala Val Tyr Ile Asn Gln His Asp Leu His Ile Ala Glu Met
            210                 215                 220
Thr Val Arg Glu Thr Leu Asp Phe Ser Ala Gln Cys Gln Gly Val Gly
225                 230                 235                 240
Arg Arg Pro Lys Ile Leu Lys Glu Val Asn Thr Arg Glu Ser Val Ala
                    245                 250                 255
Gly Ile Ile Pro Asp Ala Asp Ile Asp Leu Tyr Met Lys Val Val Ala
                260                 265                 270
Val Glu Ala Ser Glu Arg Ser Leu Gln Thr Asp Tyr Ile Leu Lys Ile
            275                 280                 285
Met Gly Leu Glu Ile Cys Ala Asp Thr Met Val Gly Asp Ala Met Arg
    290                 295                 300
Arg Gly Ile Ser Gly Gly Gln Lys Lys Arg Leu Thr Thr Ala Glu Met
305                 310                 315                 320
Ile Val Gly Pro Ala Ser Ala Tyr Phe Met Asp Glu Ile Ser Asn Gly
                    325                 330                 335
Leu Asp Ser Ser Thr Thr Phe Gln Ile Ile Asn Cys Phe Gln Gln Leu
                340                 345                 350
Thr Asn Ile Ser Glu Tyr Thr Met Val Ile Ser Leu Leu Gln Pro Thr
            355                 360                 365
Pro Glu Val Phe Asp Leu Phe Asp Asp Leu Ile Leu Met Ala Glu Gly
    370                 375                 380
Lys Ile Ile Tyr His Gly Pro Arg Asn Glu Ala Leu Asn Phe Phe Glu
385                 390                 395                 400
Glu Cys Gly Phe Ile Cys Pro Glu Arg Lys Ala Ala Ala Asp Phe Leu
                    405                 410                 415
Gln Glu Ile Leu Ser Trp Lys Asp Gln Gln Gln Tyr Trp Leu Gly Pro
                420                 425                 430
His Glu Ser Tyr Arg Tyr Ile Ser Pro His Glu Leu Ser Ser Met Phe
            435                 440                 445
Arg Glu Asn His Arg Gly Arg Lys Leu His Glu Gln Ser Val Pro Pro
    450                 455                 460
Lys Ser Gln Leu Gly Lys Glu Ala Leu Ala Phe Asn Lys Tyr Ser Leu
465                 470                 475                 480
Gln Lys Leu Glu Met Phe Lys Ala Cys Gly Ala Arg Glu Ala Leu Leu
                    485                 490                 495
Met Lys Arg Asn Met Phe Val Tyr Val Phe Lys Thr Gly Gln Leu Ala
                500                 505                 510
Ile Ile Ala Leu Val Thr Met Ser Val Phe Leu Arg Thr Arg Met Thr
            515                 520                 525
Ile Ser Phe Thr His Ala Asn Tyr Tyr Met Gly Ala Leu Phe Phe Ser
    530                 535                 540
Ile Met Ile Met Leu Asn Gly Ile Pro Glu Met Ser Met Gln Ile Gly
545                 550                 555                 560
Arg Leu Pro Ser Phe Tyr Lys Gln Lys Ser Tyr Tyr Phe Tyr Ser Ser
                    565                 570                 575
Trp Ala Tyr Ala Ile Pro Ala Ser Val Leu Lys Val Pro Ile Ser Ile
                580                 585                 590
Leu Asp Ser Leu Val Trp Ile Ser Ile Thr Tyr Tyr Gly Ile Gly Tyr
            595                 600                 605
Thr Pro Thr Val Ser Arg Phe Phe Cys Gln Phe Leu Ile Leu Cys Leu
```

```
                610                 615                 620
Leu His His Ser Val Thr Ser Gln His Arg Phe Ile Ala Ser Tyr Phe
625                 630                 635                 640

Gln Thr Pro Ile Val Ser Phe Phe Tyr Leu Phe Leu Ala Leu Thr Val
                645                 650                 655

Phe Leu Thr Phe Gly Gly Phe Ile Leu Pro Lys Thr Ser Met Pro Gly
                660                 665                 670

Trp Leu Asn Trp Gly Phe Trp Ile Ser Pro Met Thr Tyr Ala Glu Ile
                675                 680                 685

Ser Ile Val Ile Asn Glu Phe Leu Ala Pro Arg Trp Gln Lys Glu Ser
690                 695                 700

Ile Gln Asn Ile Thr Ile Gly Asn Gln Ile Leu Val Asn His Gly Leu
705                 710                 715                 720

Tyr Tyr Ser Trp His Tyr Tyr Trp Ile Ser Phe Gly Ala Leu Leu Gly
                725                 730                 735

Ser Ile Leu Leu Phe Tyr Ile Ala Phe Gly Leu Ala Leu Asp Tyr Arg
                740                 745                 750

Thr Pro Thr Glu Glu Tyr His Gly Ser Arg Pro Thr Lys Ser Leu Cys
                755                 760                 765

Gln Gln Gln Glu Lys Asp Tyr Thr Ile Gln Asn Glu Ser Asp Asp Gln
                770                 775                 780

Ser Asn Ile Ser Lys Ala Lys Val Thr Ile Pro Val Met His Leu Pro
785                 790                 795                 800

Ile Thr Phe His Asn Leu Asn Tyr Tyr Ile Asp Thr Pro Pro Glu Met
                805                 810                 815

Leu Lys Gln Gly Tyr Pro Thr Arg Arg Leu Arg Leu Leu Asn Asn Ile
                820                 825                 830

Thr Gly Ala Leu Arg Pro Gly Val Leu Ser Ala Leu Met Gly Val Ser
                835                 840                 845

Gly Ala Gly Lys Thr Thr Leu Leu Asp Val Leu Ala Gly Arg Lys Thr
                850                 855                 860

Gly Gly Tyr Ile Glu Gly Asp Ile Arg Ile Gly Gly Tyr Pro Lys Val
865                 870                 875                 880

Gln Glu Thr Phe Val Arg Ile Leu Gly Tyr Cys Glu Gln Val Asp Ile
                885                 890                 895

His Ser Pro Gln Leu Thr Val Glu Glu Ser Val Thr Tyr Ser Ala Trp
                900                 905                 910

Leu Arg Leu Pro Ser His Val Asp Glu Gln Thr Arg Ser Lys Phe Val
                915                 920                 925

Ala Glu Val Leu Glu Thr Val Glu Leu Asp Gln Ile Lys Asp Val Leu
930                 935                 940

Val Gly Ser Pro Gln Lys Asn Gly Leu Ser Met Glu Gln Arg Lys Arg
945                 950                 955                 960

Leu Thr Ile Ala Val Glu Leu Val Ser Asn Pro Ser Ile Ile Leu Met
                965                 970                 975

Asp Glu Pro Thr Thr Gly Leu Asp Thr Arg Ser Ala Ala Ile Val Ile
                980                 985                 990

Arg Ala Val Lys Asn Ile Cys Glu Thr Gly Arg Thr Val Val Cys Thr
                995                1000                1005

Ile His Gln Pro Ser Thr Glu Ile Phe Glu Ala Phe Asp Glu Leu
        1010                1015                1020

Ile Leu Met Lys Ser Gly Gly Lys Thr Ile Tyr Ser Gly Pro Ile
        1025                1030                1035
```

```
Gly Glu Arg Ser Cys Lys Val Ile Glu Tyr Phe Glu Lys Ile Ser
    1040            1045                1050

Gly Val Pro Lys Ile Lys Ser Asn Cys Asn Pro Ala Thr Trp Met
    1055            1060                1065

Met Asp Val Thr Ser Thr Ser Met Glu Val Gln His Asn Met Asp
    1070            1075                1080

Phe Ala Ile Leu Tyr Glu Glu Ser Ser Leu His Arg Glu Ala Glu
    1085            1090                1095

Asp Leu Val Glu Gln Leu Ser Ile Pro Leu Pro Asn Ser Glu Asn
    1100            1105                1110

Leu Cys Phe Ser His Ser Phe Ala Gln Asn Gly Trp Ile Gln Leu
    1115            1120                1125

Lys Ala Cys Leu Trp Lys Gln Asn Ile Thr Tyr Trp Arg Ser Pro
    1130            1135                1140

Gln Tyr Asn Leu Arg Arg Ile Met Met Thr Val Ile Ser Ala Leu
    1145            1150                1155

Ile Tyr Gly Ile Leu Phe Trp Lys His Ala Lys Val Leu Asn Asn
    1160            1165                1170

Glu Gln Asp Met Leu Ser Val Phe Gly Ala Met Tyr Leu Gly Phe
    1175            1180                1185

Thr Thr Ile Gly Ala Tyr Asn Asp Gln Thr Ile Ile Pro Phe Ser
    1190            1195                1200

Thr Thr Glu Arg Ile Val Met Tyr Arg Glu Arg Phe Ala Gly Met
    1205            1210                1215

Tyr Ser Ser Trp Ser Tyr Ser Phe Ala Gln Ala Phe Ile Glu Ile
    1220            1225                1230

Pro Tyr Val Phe Ile Gln Val Val Leu Tyr Thr Leu Ile Val Tyr
    1235            1240                1245

Pro Ser Thr Gly Tyr Tyr Trp Thr Ala His Lys Phe Leu Trp Phe
    1250            1255                1260

Phe Tyr Thr Thr Phe Cys Ser Ile Leu Ser Tyr Val Tyr Val Gly
    1265            1270                1275

Leu Leu Leu Val Ser Ile Thr Pro Asn Val Gln Val Ala Thr Ile
    1280            1285                1290

Leu Ala Ser Phe Phe Asn Thr Met Gln Thr Leu Phe Ser Gly Phe
    1295            1300                1305

Ile Leu Pro Ala Pro Gln Ile Pro Lys Trp Trp Thr Trp Leu Tyr
    1310            1315                1320

Tyr Leu Thr Pro Thr Ser Trp Ala Leu Asn Ala Leu Leu Thr Ser
    1325            1330                1335

Gln Tyr Gly Asn Ile Glu Lys Glu Val Lys Ala Phe Gly Glu Thr
    1340            1345                1350

Lys Ser Val Ser Ile Phe Leu Asn Asp Tyr Phe Gly Phe His Gln
    1355            1360                1365

Asp Lys Leu Ser Val Val Ala Ala Val Leu Val Ala Phe Pro Phe
    1370            1375                1380

Val Leu Ile Ile Leu Phe Ser Leu Ser Ile Glu Lys Leu Asn Phe
    1385            1390                1395

Gln Lys Arg
    1400

<210> SEQ ID NO 2
<211> LENGTH: 4206
```

<212> TYPE: DNA
<213> ORGANISM: Triticum aestivumn cv Chinese Spring

<400> SEQUENCE: 2

| | | | | | |
|---|---|---|---|---|---|
| atggagggcc | tcgcaagaga | gaccaaccca | tcatcccacc | atcaagattt | caccgcctgt | 60 |
| gcgagtgacg | agcgcccgga | tgagtccgag | ttagaattgg | catcgcgaca | gcgccagaat | 120 |
| ggtgctgcaa | acaccgagca | tgtgagtgag | aacatgctgc | ttgacagcag | caagttggga | 180 |
| gctctcaaga | ggcgcgagtt | cttcgacaac | ctgctaaaga | acctcgaaga | cgaccacctc | 240 |
| cgctttctgc | gcggacaaaa | ggaaagaatt | gacagggttg | atgtcaagtt | gccagcaata | 300 |
| gaggtgaggt | ataataatct | gtttgtggag | gcagagtgca | gagttactaa | aggaaatcac | 360 |
| ctgccatctc | tatggaatag | taccaaaggt | gccttctcgg | gcctcgtgaa | gttgctaggc | 420 |
| ttcgaaacgg | aaagagcaaa | aaccaacgtt | cttgaagatg | tcagtggaat | catcaaaccc | 480 |
| tgcagattga | ctcttctact | gggacctcct | ggatgtggca | aaagcactct | gttgcgagct | 540 |
| cttgccggga | aactagataa | atctctaaag | gtaacagggg | atatctctta | taatggttat | 600 |
| gaacttcatg | aatttgtacc | tgagaaaaca | gctgtgtata | tcaaccaaca | tgatctgcac | 660 |
| atagctgaga | tgactgtgag | ggaaacttta | gacttctcag | cccagtgcca | aggtgttgga | 720 |
| agaagaccaa | aaatactcaa | ggaggtgaac | acaagggaga | gtgtggctgg | gatcatacct | 780 |
| gatgcggaca | tcgatctata | catgaaggta | gtagcagttg | aagcttcaga | gcgaagccta | 840 |
| cagacagatt | atattttgaa | gatcatgggg | ctagagatat | gcgcagacac | gatggttggg | 900 |
| gatgcaatga | agaggaat | atcaggggg | cagaagaaaa | gattaaccac | agccgagatg | 960 |
| attgtgggcc | ccgcaagtgc | atactttatg | gatgaaatat | caaatggtct | ggatagctct | 1020 |
| accactttc | aaataatcaa | ttgtttccag | caactgacaa | acatcagcga | gtacacgatg | 1080 |
| gttatttcac | ttcttcaacc | aacacctgag | gtatttgatc | tttttgatga | cctcatacta | 1140 |
| atggcagaag | ggaagattat | ctaccatggc | cctcgaaatg | aagctctcaa | tttttttgag | 1200 |
| gagtgtgggt | tcatatgccc | agaaagaaaa | gcggcagctg | actttcttca | agagatcttg | 1260 |
| tcctggaagg | accaacaaca | gtactggttg | ggtccacatg | aatcatacag | atatatctca | 1320 |
| cctcatgaat | tatcaagcat | gttcaggag | aatcacaggg | ggagaaaact | acatgaacaa | 1380 |
| agtgtacctc | ccaaaagcca | gttgggcaag | gaagctttag | cattcaataa | gtattcgcta | 1440 |
| caaaaactgg | aaatgttcaa | agcctgtgga | gcaaggaag | cactcctaat | gaaaaggaat | 1500 |
| atgtttgttt | atgtcttcaa | aacaggccag | cttgccatta | ttgcactcgt | aacaatgtct | 1560 |
| gtattccttc | gaactcgcat | gacaataagt | ttcactcatg | caaattacta | tatgggagca | 1620 |
| ttatttttt | ccatcatgat | tatgttaaat | ggcataccag | agatgagcat | gcagattggg | 1680 |
| agactcccaa | gttttacaa | gcaaaagagc | tactatttct | attcatcatg | gcatatgca | 1740 |
| ataccagctt | cagtcctaaa | ggtccctatt | tccatactgg | attcgcttgt | atggatatct | 1800 |
| atcacatatt | atggtattgg | ttatacacct | actgtttcaa | ggttcttctg | ccagtttctg | 1860 |
| atactttgtc | ttctccatca | ttcagtcacc | tcgcagcatc | gatttattgc | ttcatacttc | 1920 |
| caaacaccta | ttgtgtcttt | cttctacctt | tttcttgctc | taacagtatt | ccttacattc | 1980 |
| ggaggcttca | ttcttcccaa | gacctccatg | ccaggatggt | aaaactgggg | attttggata | 2040 |
| tctccaatga | catatgcaga | aatcagcata | gttattaacg | aattcttggc | accaagatgg | 2100 |
| cagaaggaaa | gtattcaaaa | cataacaatt | gggaaccaaa | tcctggttaa | tcatggccta | 2160 |
| tattacagtt | ggcattatta | ttggatatcc | tttggagcct | tgcttggatc | tattctctta | 2220 |

| | | | | | |
|---|---|---|---|---|---|
| ttttatatcg | cttttggatt | ggcactagat | tacagaacac | ctacagaaga | atatcatgga | 2280 |
| agcaggccta | caaagagctt | atgtcaacag | caggaaaaag | attacactat | tcaaaatgaa | 2340 |
| tctgatgatc | aatcaaatat | ttccaaagca | aaggtgacta | taccagttat | gcatcttcca | 2400 |
| attacattcc | acaatctgaa | ctactacatt | gatacccccac | cggaaatgct | gaaacaaggc | 2460 |
| tatccaacaa | gaagacttcg | actgcttaat | aacataactg | gtgctttacg | tcccggtgtt | 2520 |
| ctttctgcac | taatgggtgt | tagtggagct | gggaagacaa | ctctactaga | tgtattagca | 2580 |
| ggaaggaaaa | caggaggtta | tattgaaggg | gacataagaa | taggtggata | tcccaaggtg | 2640 |
| caggaaacat | ttgtcagaat | cttgggttac | tgcgaacaag | tcgacataca | ttccccacag | 2700 |
| cttacagttg | aagagtctgt | aacttattct | gcgtggcttc | gtctgccttc | tcatgtcgac | 2760 |
| gaacaaacaa | gatctaaatt | tgttgctgaa | gtccttgaaa | ctgttgaact | agatcaaata | 2820 |
| aaagatgtct | tagtggggtc | accacagaaa | aatggattgt | ccatggagca | gagaaagagg | 2880 |
| ctaacgattg | cagtcgagct | tgtttcaaac | ccatcaatca | tactaatgga | tgaaccaaca | 2940 |
| acaggtttag | atacaaggtc | agcagccatt | gttattcgtg | cagtcaaaaa | tatttgtgaa | 3000 |
| acaggaagga | cagtagtctg | tacaatccat | cagccgagca | ctgaaatttt | tgaggcattt | 3060 |
| gatgagctca | tattaatgaa | aagcggtggg | aaaacaatct | acagtggacc | aataggagag | 3120 |
| cgctcctgca | aagtgatcga | gtactttgag | aaaatttctg | gagtcccaaa | ataaagagt | 3180 |
| aactgcaatc | cagctacttg | gatgatggat | gtaacatcga | catcaatgga | ggttcaacac | 3240 |
| aatatggact | ttgcaatttt | gtatgaagag | tcgtcactgc | atagagaagc | tgaagatcta | 3300 |
| gtggagcagc | taagtatccc | attaccaaat | tcagaaaatc | tatgtttctc | ccatagtttt | 3360 |
| gcacagaatg | gctggattca | acttaaagct | tgcttgtgga | aacaaaacat | aacttactgg | 3420 |
| agaagtcctc | agtataactt | gaggcgcatt | atgatgactg | tcatatctgc | cctgatctac | 3480 |
| ggaatattgt | tctggaagca | tgcaaaagta | ttaaacaacg | agcaggacat | gctcagtgtt | 3540 |
| tttggtgcaa | tgtatttggg | tttcaccacc | ataggcgctt | ataatgatca | gacaatcata | 3600 |
| ccattcagta | caactgagcg | tattgtaatg | tatcgtgaga | gatttgcagg | aatgtattca | 3660 |
| tcttggtcat | attcattcgc | acaggctttc | attgagatac | cctatgtatt | tatccaagtg | 3720 |
| gtactgtata | cgttaattgt | ctatccgtca | actggttatt | attggacagc | acacaaattc | 3780 |
| ctatggttct | tctacaccac | attttgttca | attctctcct | atgtttatgt | tgggttgctt | 3840 |
| cttgttttcca | taacccccaa | tgttcaagta | gctaccatac | tggcttcatt | tttcaacacc | 3900 |
| atgcaaacac | tattctcagg | atttatttta | cctgcacctc | aaatcccgaa | gtggtggact | 3960 |
| tggctctact | atctcactcc | tacatcttgg | gcactcaatg | ccctcttgac | atcacaatac | 4020 |
| ggaaacatag | aaaagaggt | gaaagcattt | ggagaaacta | atcagtttc | aatcttcttg | 4080 |
| aatgactatt | ttgggtttca | tcaagataag | ttgagcgtag | tagcagctgt | cctcgttgcc | 4140 |
| tttcctttg | tgttgataat | cttgttttcg | ttgtccattg | agaaacttaa | tttccagaag | 4200 |
| aggtaa | | | | | | 4206 |

<210> SEQ ID NO 3
<211> LENGTH: 18859
<212> TYPE: DNA
<213> ORGANISM: Triticum aestivum cv Chinese Spring
<220> FEATURE:
<221> NAME/KEY: misc_feature
<222> LOCATION: (11016)..(11069)
<223> OTHER INFORMATION: n = unknown number of nucleotides

<400> SEQUENCE: 3

-continued

```
agccggcggg gtcggcgagg ttgagaagca gaggccggtc atgtcgctac ggatcagaga      60
ggaggagcgg tgacgcgttc cagatgggtt tgggcaggcc gcggtggcta agggagaggc     120
agcaagactt ggcggcggcg gtttggattg aacggaaaaa caaggaaggt ctatggtggc     180
ggttgcggct ggatcaggga gcatcttgat ggaggaaatg ggtaggggaa gtggcggtgg     240
tgggatgact ttcaggggta tatctagggt tggtccaaaa tagggctagg gggctatata     300
tagggaaata ggtctagatt cgaagccttc gattagatcg gacggtcgag ataaaatgat     360
aagggaggcc aaataagaaa ccaaagatgt ttggggttga tccggaccca ccggtcacga     420
ccgggcggtt cgggttcggg gaagttttcg agctaggatg caagggggtc tatgcaatgt     480
gcagagagac aaggaagtcg tgcgcaagtg cggttggtct cgaaaccgtc aacgacaaca     540
acagggagaa cggcaactat gaacggatgc aagttttgga aaatgcaatg atgaatgcaa     600
caaacaaata attaacgcgg ccaactcgag atataactag aaggcatctg gagcgtcggt     660
ctcgagttgt tacacactcg ctcaccgggc ccctcccagc gccctcaaca acctttgacc     720 tccccccaa cggtggtacc agacgccccg gaactagccg cactccccc ccccctccga      780 atggggggcaa cgaaaacaag gggcacccag gcgccaagaa taagaagaga gggccggtgc     840
gctccgctag gtaccaacag gctcaccctc cctccgcggc cgttgttgcc tccatcgagc     900
cagccgccga ctccgaccac gatggccggc cttgcttcaa ctgtgtgatc cccggttact     960
tccaagtcgc atgccccaat cgtccgatgt gctacttgtg taaggatccc gggcatcccg    1020
ctctgttgtg cttgaaccgg tcggtttcgg aggagttgat gatgtacggg cacggcccag    1080
ggggcatgcg cttcttccac atcaaggtcc cggatgcccc acccctgcg aaaagatcag     1140 atctattata aagattcacc agaagtacaa aacacctcaa aacataataa aatttacatc    1200
aaggtccatg gaggaatgga ccaccgaacg gccattgcct cagccagaac cgagccgccg    1260
acacgccgct atcgacgctc ccataccgga gccggtctga ccttgtcgat gatagccgaa    1320
aagtcttcgt gtgcgtgccc ttaaggatca gcgtcccaga gccgcagtcg tcaccgttga    1380
atccttgaat cagtctaaag aatttgacac caaatatcgc cgttgcgtac gcacggcgag    1440
aaactctaac ctctccgccc tgaggagctg gcagaaatct acgccgaagc tccgtctaat    1500
ccgtcctaga ggacgaactt gaggaggatc ggaacccgaa agactgactc gaagaagaag    1560
cgccgccatc cgtccaaacg ccgccctgc gagaactaaa actctacctg tctactagcc     1620
ggagacaagg caccagaaat ccctcctg ccaccagccg ccggaacggc aggcggaggg     1680
aaggggaatc cacgggctcg ccgatgaaga tcaaggggag gaaggcttt cacgacaggg     1740 gaaagaaaag caatcttaat cttttatatc tttacaacca aaattccaaa ttgagttttg    1800
gttccatatt catgtttcta ttacaagggc ttttaaataa tatccatttt taatacgatt    1860
tgatgagttt ttaaaacttc attaagttgc agctgctgaa acttggtacc agcaagcgac    1920
aaaatcatga aacttgatgc gagcgaatgg caaaatcgta agtttcaaaa actgaaactt    1980
aaaacttgat gtgccgtcgt gcggaaccat cgagcagccg ggcaggtgcg tgccacgcgc    2040
ctgcgtgccc ctgcgagttt tccgcgcaag agcgcgaaca acggtactg cacatattgc      2100 agtttcaagt tgccgagtgc gactctgtgg tcaatgtcgt cgaaggctct ttcatcaagt    2160
aattacaata ccatttcaac tttcatgggt ccgtgcctgc caggttcaaa gttccaagat    2220
ggttatgtgc aaccgactgt gtgtcccaca tccacacatc gaagcagagg tctcgtgaag    2280
tctttccaaa cgagcaagag caacatcaag gacgaccagc tgagggggtc tttccaaacg    2340
```

```
agtggtttct atcctcccgt agaatgggtg atccacgaca agtctatgag tcgttctgag    2400
gttgagacta taaattaat tgtggctaat cgacactagt cgacaccgaa gttgctactc     2460
acagactagt cgacactgaa gtgtagtcgg ccccggagtt gtgacttcta gactagtcta    2520
tagacttgtc cttcgactca taatccatgc tcgtcatcca gcccccatta acccatcca    2580
tgtgactccc tgcgtaacat aacctgttcg gttactcccc ttctaatcca tgactaaaat    2640
tgcacttcaa tcttttttccg aagtcccgtt ttgcggtggc atatatccaa tttacaagct   2700
aaaaaaagt gcggtggggt tctttcccgt cacaaagaaa acccaaaata aggcaaatca     2760
ggtctccgaa tcaggagtac tgtgaagtct tcaccagtac cgtataatac atgacttatg    2820
gctgtcatct tccagaatgt gcgtttccat gctaatagtt agtttgaagt caacacatga    2880
ctggtctttc caactcttct gactgatgat gtccgtatgg gaaaaagcgt gcgtacatgc    2940
tcgccaaaac cttatatatg tactctaaag agaaggaaat gactgcttag agtacggcta    3000
ggcaatagca aagggcgtcg atttaactca cccatcttga gatggagggc ctcgcaagag    3060
agaccaaccc atcatcccac catcaagatt tcaccgcctg tgcgagtgac gagcgcccgg    3120
atgagtccga gttagaattg gcatcgcgac agcgccagaa tggtgctgca acaccgagc     3180
atgtgagtga aacatgctg cttgacagca gcaagttggg agctctcaag aggcgcgagt     3240
tcttcgacaa cctgctaaag aacctcgaag acgaccacct ccgctttctg cgcggacaaa    3300
aggaaagaat tgacaggcat gttttctttt tcagaacact gttctaagta actggatgaa    3360
gattagactc tgtttatgca actgtttatt tttcccctgt gatccatttc cacagggttg    3420
atgtcaagtt gccagcaata gaggtgaggt ataataatct gtttgtggag gcagagtgca    3480
gagttactaa aggaaatcac ctgccatctc tatggaatag taccaaaggt gccttctcgg    3540
taagaaacct ctgaaatgat tgattttttat tatgcaccaa atagcagcat ctgaagcaac   3600
tgttttttcg acgaatcata aatggaactg ataagacaca gatatatgtt ggatggtatt    3660
gactaactta cccgttttca tttgagttac agggcctcgt gaagttgcta ggcttcgaaa    3720
cggaaagagc aaaaaccaac gttcttgaag atgtcagtgg aatcatcaaa ccctgcaggt    3780
atgtgccatg tttcatgagt gtttagtata aaaatggaaa agaaaccata acatacaaa     3840
agaaaacgtg cgaaatttag tgcatcaagt gtctgtagtt cttgctttag agattaaggt    3900
tagttctgat tccatatgtt cccatctttg tagattgact cttctactgg gacctcctgg    3960
atgtggcaaa agcactctgt tgcgagctct tgccgggaaa ctagataaat ctctaaaggt    4020
acaaatactg tcttccttc ataattaaag aaaaaagcat gtccttgttt tcactgattg      4080
catctgctcc tataaagatc tcaagattac tcaatacttg gccaaatgaa agaacaaaaa    4140
aattaagatc tcaaccagct gcacaccgca gtaaactgct ctctgtcctc tggccgctac    4200
ataatagacc acatatgaag ccagtacaca aataaatgta taacctacaa tcttttctca    4260
aagtctacat cattcatgaa tagccaaaga gccaaactta agttttatc aatccccac      4320
aaacaataaa ctcgcgcctc ttgagagctc cgaacttgct gctgtcaagc agcaagttct    4380
cacgcacatg ctcaaatgtt tgcagcacca ttctggcgcc gtcgcactga caattctaac    4440
tcggactcgt cgggaccctc gtggtcatac gccagcgctc ccaaatcctg ataccagaac    4500
agataatgac gctgacgctg ccagaggaga cggcgcaatt gccttaatcc tcggcacata    4560
gtgtcgcaac acatacatgt gcccaactac tcctcggcac cacgcccgcc ggaggacaag    4620
ccggcgctcc tgtcccctaa ccatgacacc gacatcaaga acctccgcct agaactcttg    4680
cacaacctcc tccgacttct ggtgacagaa acgcgccacc ggtgacacaa agccaccgtc    4740
```

```
atccgcatat gacccaacct ccagcagcat cctgagattc aacacatgac acctccgctg    4800
ccctctcctc catggcatcc tcggcagcca ggaaagataa tctcaatccg ctggatcccc    4860
ctaaagtagg cgtctaggcg atcactgtgg cggcagggtg agtcaccttc agggcagcgc    4920
tctcatccaa ttcctatgta ggtttgctac tactgcacgg ggacctatca gatgtatctc    4980
acagaccaat tagataaatc gatggtcgaa tttggaagtt ataatgagat acactgttgt    5040
gattaaattt gatcacgcta tattgtagag gaaagtgtaa ttcccttgaa atgaacaaca    5100
tgcaacatag tagtatagaa tcgccgcaaa ttttccttgc gtttggatat aaaactcagg    5160
cccatgttcc atcttttttaa ctgtgtatat gccctagcag cgtgaacata ctactggtcc    5220
tgctagaaca agcggcgggt aaagatgggc gcctgcttca tacttgccag taaattagga    5280
tgattgcctt gcagaaaata tggccaatat taccattaag cctatttacc gaaatctaac    5340
acaaactttt gactgtagga aacaaagaat caattctact aacagatttt tcttttgttc    5400
gagaaaatgc ttatgcgtgt gtcgatgcat aaaaggaaa gagaataaca gccattcagg    5460
attacaagcc ctaagaagga ccatggaact cctgaaccaa ggttacacgc caggcaggag    5520
gagctggagt tttgccgcac gggcgaaacc cagcaagtcg cctccgtgct acgctaggtc    5580
tagccatact gaaggataca tcattgtgat gagcaccagg ccgtcatctg aatgagtgtc    5640
agacaactga cagaataaca ttactcacat caaaagcaaa agttgtccat cacctcagag    5700
tctatggttt tcattagttg cacatggtta acgacctctg acaaaggcag aaattcaaga    5760
atgccttgca ctgaacgacg gatatcagta tacttaagtt gcttttttac agcaccaact    5820
gatgctggag ttatcaaatt gaaatgtccc aactccccag caaagccacc tatattgtct    5880
ccaaaacata taattgttgg catggtttcc acctgtatga accggcact atttactggc     5940 tcaaatgagt agttcgtcat gaagctagta cttatactga ctgctgaata ctaataaata    6000
acagctttta attattttca gaccaagtac tttcagagaa aactattttc agatcagctt    6060
ctaattaata ctccctcagt tccaaaatat aaggtgtatt agttttttca agaggcattc    6120
atgtttgacc aagtttttag aaaaaaaata tcaatatcta caataccaaa tttgtatgat    6180
tagatttatc acgaaaagta ttttcatat tttatttatt ttatattgca gaatgttaat     6240
attttattct ataatcttgg tcaaacatac ataagtttga cttgcacgaa cactgatgca    6300
ccttatattc tggaacggag ggagcaaata atagcacaca atagattatg ggtacctgct    6360
gggtattcct gcttagagat acaaccacag aaaagcagag cagaacagca caaatgccct    6420
ttagccattg acactacaat tagtttcaaa gctacatttt gcaaaatca tgaacaaaag     6480 aagaaaaaaa atggcaaact gaatgtaacg atgcaagctt ttacaggtaa caggggatat    6540
ctcttataat ggttatgaac ttcatgaatt tgtacctgag aaaacagctg tgtatatcaa    6600
ccaacatgat ctgcacatag ctgagatgac tgtgagggaa actttagact tctcagccca    6660
gtgccaaggt gttggaagaa gaccaagtaa gtcattgga cagtcctcac aagaattcat     6720
gatcaaaaat aagttcttaa ataatcacaa catttgttgc tcactaaatt tgtttgccca    6780
aagaaatact caaggaggtg aacacaaggg agagtgtggc tgggatcata cctgatgcgg    6840
acatcgatct atacatgaag gtaaaaaatc gtgtctccta tgtactggct ggcattatcc    6900
tttctcactt tacaattaaa aaaaaaacag acctgcttat ctgagttaca agaaaaggt     6960 aattcaacgt cgaatgaata ttggaactgc tctagcagaa taatatttgg ttgtattaaa    7020
gctaagctag ctttttcaatt tttcattagt caacacttct gtttctgttt ctacaaatta   7080
```

```
aacgtaactg tttttcaaaa gtaaagcggc taatgcaggt agtagcagtt gaagcttcag    7140
agcgaagcct acagacagat tatattttga aggtacccct tgccaaaaca tctaagttta    7200
tgcataactt ggtgctgaag gcagatagga acaagatact aacagaatca caatactgat    7260
ttatttgtag atcatggggc tagagatatg cgcagacacg atggttgggg atgcaatgag    7320
aagaggaata tcagggggc agaagaaaag attaaccaca ggtatagtaa acccaatggg     7380
aaatacatta accaacaagg gatcaccttg tatataatct ttcacctact tgtaccagcc    7440
gagatgattg tgggccccgc aagtgcatac tttatggatg aaatatcaaa tggtctggat    7500
agctctacca cttttcaaat aatcaattgt ttccagcaac tgacaaacat cagcgagtac    7560
acgatggtta tttcacttct tcaaccaaca cctgaggtat ttgatctttt tgatgacctc    7620
atactaatgg cagaagggaa gattatctac catggccctc gaaatgaagc tctcaatttt    7680
tttgaggagt gtgggttcat atgcccagaa agaaaagcgg cagctgactt tcttcaagag    7740
gtaattgttc tcaatcacaa aaataactgc agcaactgag atgatttgca cgttgatgaa    7800
accagttttt tttctaattt tgaaatcatt agatcttgtc ctggaaggac caacaacagt    7860
actggttggg tccacatgaa tcatacagat atatctcacc tcatgaatta tcaagcatgt    7920
tcagggagaa tcacaggggg agaaaactac atgaacaaag tgtacctccc aaaagccagt    7980
tgggcaagga agctttagca ttcaataagt attcgctaca aaaactggaa atgttcaaag    8040 cctgtgagc aagggaagca ctcctaatga aaggaatat gtttgtttat gtcttcaaaa     8100
caggccaggt taaacttcat tctgaggcac tctttcctgt acaaagtaaa ttatgagtcc    8160
aaactgagat ttactccttg atgcagcttg ccattattgc actcgtaaca atgtctgtat    8220
tccttcgaac tcgcatgaca ataagtttca ctcatgcaaa ttactatatg ggagcattat    8280
ttttttccat catgattatg ttaaatggca taccagagat gagcatgcag attgggagac    8340
tcccaagttt ttacaagcaa aagagctact atttctattc atcatgggca tatgcaatac    8400
cagcttcagt cctaaaggtc cctatttcca tactggattc gcttgtatgg atatctatca    8460
catattatgg tattggttat acacctactg tttcaaggta aatatggaaa tttctcaacc    8520
ttacaatgat aagaacaaac attgagaaac tcttaacata ttttatttat attcatttct    8580
aggttcttct gccagtttct gatactttgt cttctccatc attcagtcac ctcgcagcat    8640
cgatttattg cttcatactt ccaaacacct attgtgtctt tcttctacct ttttcttgct    8700
ctaacagtat tccttacatt cggaggcttc attcttccca agagtaagat aaccattgct    8760
cattgaatgc atataactta taagcctagc aaatctgaac aaatttgtta ctttattgtc    8820
ccagcctcca tgccaggatg gttaaactgg ggattttgga tatctccaat gacatatgca    8880
gaaatcagca tagttattaa cgaattcttg gcaccaagat ggcagaaggt gaaatgattt    8940
ttttttcaaa taaatattg agtgataagc tgatgtcaag catctaacat cattgctgct     9000
tgtattattt tcaggaaagt attcaaaaca taacaattgg gaaccaaatc ctggttaatc    9060
atggcctata ttacagttgg cattattatt ggatatcctt tggagccttg cttggatcta    9120
ttctcttatt ttatatcgct tttggattgg cactagatta cagaacacgt aagtttgcta    9180
ctaatgaaca aagtgcatat atattgggct tgggctccat ggtgcccagg caacatgatt    9240
tgaaatacag caaatttggg taatgcattt aggaaattcc tattttggat gatataactg    9300
gttgtcattg ctgggtataa tttcgaaata cctactcgat cccaaatatt tttggtaaac    9360
tcatccatat agcagtttta tatacataca ggtacctaga attcaagcaa taacaaaaca    9420
aagtacagac tgaaaagatc aaacttgttt ggaataaatt agacttcaca aattttcatg    9480
```

```
caatatatct agatggatct ggatatagga atatagtgct gaggcactat ggagcaccag    9540
ttaattagac tttatacacg aatgttactt actttagaat cctactataa ttttgccaat    9600
ttcagctaca gaagaatatc atggaagcag gcctacaaag agcttatgtc aacagcagga    9660
aaaagattac actattcaaa atgaatctga tgatcaatca aatatttcca aaggtaaaga    9720
cataaacatc tcaatacgaa ttaatagtaa aaaatatgaa ggtcccataa aagtgcatgc    9780
ttcttcaatg cattcatctt attgcagcaa aggtgactat accagttatg catcttccaa    9840
ttacattcca caatctgaac tactacattg atacccccacc ggtaattaag caagcccct    9900 atgcatttgt tttgtagttt tttatatttc ttgcctggtt cgtatttgat gatgaaggta    9960
tgtaagaaat gtactctctt gtaggaaatg ctgaaacaag gctatccaac aagaagactt   10020
cgactgctta ataacataac tggtgcttta cgtcccggtg ttctttctgc actaatgggt   10080
gttagtggag ctgggaagac aactctacta gatgtattag caggaaggaa acaggaggt   10140 tatattgaag gggacataag aataggtgga tatcccaagg tgcaggaaac atttgtcaga   10200
atcttgggtt actgcgaaca agtcgacata cattccccac agcttacagt tgaagagtct   10260
gtaacttatt ctgcgtggct tcgtctgcct tctcatgtcg acgaacaaac aagatctgta   10320
tgtcatcagt ctcagagata tatcgaattt aataagcata gcactagatg gataaataag   10380
aggcttacct aagaaactaa caatattctt cttgttcctc tcgtagaaat ttgttgctga   10440
agtccttgaa actgttgaac tagatcaaat aaaagatgtc ttagtggggt caccacagaa   10500
aaatggattg tccatggagc agagaaagag gctaacgatt gcagtcgagc ttgtttcaaa   10560
cccatcaatc atactaatgg atgaaccaac aacaggttta gatacaaggt cagcagccat   10620
tgttattcgt gcagtcaaaa atatttgtga acaggaagg acagtagtct gtacaatcca   10680
tcagccgagc actgaaattt tgaggcatt tgatgaggta atttaacttt ctaaatatat   10740
tagtatatta aacacaatca acacaaatac atttttatta tatatatcaa gcacgatcaa   10800
cacaattttt tttctggaaa aatcaatatg tttagtttca aaactattag gattaattaa   10860
agcccttgcc ttcaacagag cagggctaat cttaatatgc actacctctg taactaaata   10920
taagacgttt ttgcagttca cctgcaaaaa cgtcttatat taagttacag aggtacctcc   10980
gtcccataat gtaagacgtt ttttgacact agtgtnnnnn nnnnnnnnnn nnnnnnnnnn   11040
nnnnnnnnnn nnnnnnnnnn nnnnnnnntt atgggacgga gggagtagta cattattagt   11100
tatttaaaat ttaaaacatg tcctttgtgt ttgcctttct agtaaataat aatgatagga   11160
aataatagta tggaaatttg caatataagc gtgtcaacca tttcactttg cgcaacctag   11220
acctcaaatt gcacttttgt cccctcaaat gatcaattat gtgcaacaaa accttcaac   11280 ttaaactttg cttatctgaa accttctatt atttggtttg ttagatcaag cattttctac   11340
tgaagatacc tgatcagacc cctttgaata atatatctat gaataaacat tgatttgagc   11400
taagtaggat tggcatctaa attatagtaa gacgcttaac aactatttac tactccctgt   11460
ctcaaaatgt aagacatttt ttgacccttt gaataatata tctatgatat aaacattggt   11520
ttgagctaag taggattggt atctaaatta tagtaagatg cttaacaact atttactact   11580
ccctctgtct caaaatgtaa gacattttt gacacatgta agacgttttt tgacattatc   11640
agtgtcaaaa aatgtcttac attttgagat agagggagca tctagcatcc tttttctgtt   11700
tcgggagaac atttcttacc ttaaatattt ggcatatact ttttgtacaa aaacaacccc   11760
attatatcag tccgcatgaa gaataaagta taaacatgca atgacatgtt ttgatctctt   11820
```

```
aattatttga acatctatgt gttcgatgtc agttaatttt tatctcttat ttgaactaag    11880
tgtccacact gacacaaatt tgtcatcgca caaaatttgg actttctggg cttgattaca    11940
aaattaaaac aattttgagg gcttatactg gaaagtcacc gaatagaata ttttttggtt    12000
ttctgaacta tatgtttatc acaaatcgac gtgactacgg acagtttata tttgctactt    12060
ctctgtttat aataacaaaa agggtataga ttttctttat tacagggcta gttgtagtcg    12120
aaagttgcct ataatgcatg tagtaaattt tgttgcagct catattaatg aaaagcggtg    12180
ggaaaacaat ctacagtgga ccaataggag agcgctcctg caaagtgatc gagtactttg    12240
aggcaagttt cttgaacata tttccacaaa tgtatttgcc ttttcttga ttattcgttt     12300 tcactgtttt tttctggaat tggaacaata aacgtgagag ttccaaagga acgaacccca    12360
aaaccagtgc tcaaatgttc aacatgccat agcaaaaaca cttaagtcaa ctctagcagt    12420
catttgtgtt caatatgtaa cttggctaac aattcacatg aaatatatag gttaatcaaa    12480
attttgatgt gatcatatgt attttacatg ttgaacttaa aagcaaatgt gacaataaac    12540
gtacagattg gcaatggaaa ctaaaaacat actgaagaac tttgtttgca tatctatgta    12600
tgtgtttcgg tgttttcaga gaggaagcac ggttgtggca tggcactgcc atatttgtga    12660
catgtgtcct ttggttctaa tagattgaat ttttcttgtc cacttgatag aaaatttctg    12720
gagtcccaaa aataaagagt aactgcaatc cagctacttg gatgatggat gtaacatcga    12780
catcaatgga ggttcaacac aatatggact ttgcaatttt gtatgaagag tcgtcactgc    12840
ataggtacat atcttgtgga tttagttagg atatcgagca aaaggcaaca tatatgaata    12900
gcttaagcaa aataaaattc atctagcaaa aaaatttagc caaacaaaat acctccattt    12960
gaagtttgga agaattaaag ttacttttct gcagagaagc tgaagatcta gtggagcagc    13020
taagtatccc attaccaaat tcagaaaatc tatgtttctc ccatagtttt gcacagaatg    13080
gctggattca acttaaagct tgcttgtgga aacaaaacat aacttactgg aggagtcctc    13140
agtataactt gaggcgcatt atgatgactg tcatatctgc cctgatctac ggaatatttgt   13200 tctggaagca tgcaaaagta ttgtaagttc actcctttgt tatccacaac attgcacatc    13260
agttgacttc acagactcat tgcaaaatta ttctaacttt ctcttatctc ttctaagaaa    13320
caacgagcag gacatgctca gtgttttttgg tgcaatgtat ttgggtttca ccaccatagg   13380
cgcttataat gatcagacaa tcataccatt cagtacaact gagcgtattg taatgtatcg    13440
tgagagattt gcaggaatgt attcatcttg gtcatattca ttcgcacagg tcagataatg    13500
atcacaagct tgtaagagaa gtaaaatata cattgacact gatgctcata tttattcacc    13560
ttctacaggc tttcattgag atacctatg tatttatcca agtggtactg tatacgttaa     13620
ttgtctatcc gtcaactggt tattattgga cagcacacaa attcctatgg ttcttctaca    13680
ccacattttg ttcaattctc tcctatgttt atgttgggtt gcttcttgtt tccataaccc    13740
ccaatgttca gtagctacc atactggctt catttttcaa caccatgcaa acactattct      13800 caggattat tttacctgca cctgtaagtc tttatctcct cccaatatcg taaactttag      13860
ctctccaaga tgtaactggc acttcttttt gttagcaaaa atatggctgc ccaccttgaa    13920
tatataccaa ctaagaaaat aacaacctac atgagaaatt gtaattgacg agattttgta    13980
gtgtaattat gtaataatat tatggaacta ataaaggtct aataggggcat tatgggcttt   14040 actttattcc agagttcatg ttcgtgcaga agtctcctat tgtactacat ctaggttacc    14100
cttataggca tccttattaat gcattctgcc ttacaaaggt atcaaattag gttttagggt   14160
ttttatcctg gtaaactttt ctttatcttt ttttgtcaat attcacctttt gcaacttccc   14220
```

```
caccatgaca ccttttttt ccttctgccc cagatcctca attttactga ttgcttaatt    14280
tttgtgatcg atcaactgat ctatcctcct gatagatctt agttttggga atatttaagt    14340
agtaatatgt caacaataca aggaccaacc gcaactataa ggcatcactg gatgacgata    14400
cacagaacca ctccaatgtt agtttaacat cataatagtt atagacatac catcttcagt    14460
ttcatcatta atacttccat ttctattttc taggttggaa attgataatt attccagcgt    14520
tgctcaatag aataatcatg ttctgttcaa ttgttaggga agaatcatga atagaggaaa    14580
gcactaatat gcattttcaa ttcacgttgc agcaaatccc gaagtggtgg acttggctct    14640
actatctcac tcctacatct tgggcactca atgccctctt gacatcacaa tacggaaaca    14700
tagaaaaaga ggtgaaagca tttggagaaa ctaaatcagt ttcaatcttc ttgaatgact    14760
attttgggtt tcatcaagat aagttgagcg tagtagcagc tgtcctcgtt gcctttcctt    14820
ttgtgttgat aatcttgttt tcgttgtcca ttgagaaact taatttccag aagaggtaag    14880
caagttctga cattccaaca gacatgaatc tgtacatgtt acagatatag ctacttgcct    14940
tttttccaac tgcgaaatgc agaatcagag ctgattgggt ggctattttt ctcaaatctg    15000
atgggtaaac ctcatgaata agtaattgtg tacaataact tgattgtgct aagtacgatt    15060
gtgagttgta atcttttgt ttcaccgttc agaagaattt gatggttaca aatcatgtaa    15120
cctgctttga agaggatttt gcaattgtgt tatgccttag attactgaat gcatcaagag    15180
gaaaatgagc acctaactga atgaacctac gatttaaagc gagcttaagc acagataaca    15240
aaaagctaac ttggattccc gcaccgtcat catcatgcct taatatccgt gcaaggtgtg    15300
tgagtggtgg gtggtttctg aagagaaacg tggccacacg tcacggcatg cggggcgccg    15360
tttggatttc ctttgagcta tataaaacgg gaacggcagc atggaatggt acacttctct    15420
cactttcacc catcttcatc ttgctcatgt gctcactccg ccgttgcaaa caaagcttct    15480
cgcatcaagc ttttctcccc ttcctctatt agacaagttg aagccagaca cacccgatga    15540
gcgcagaggt gcaagccgaa ggagaggatg cagcgcaacc actagggtg ctaccagcaa    15600 gaagggtgcc actagcaagg gtgccgccaa cgacacaaaa gggaaatggg tcacttcgtc    15660
ggcgacacaa catcgtcgac acaagatcaa ctgacaaagc tcgccaactg ttgcttcttc    15720
cccaatattg ttcttcccga agcaaatgga agttcactgg cgcgcaccgc cgcgggagca    15780
gatcgtgcca gcgccatgcc cggacgaacg ggtattccta gcccctttct tgatgtgagg    15840
cttctctttg cctctccatg agtttcttcg tgggtagctt ttcttgtacg aggccaataa    15900
tatgtcacat cacgtgagac tggtcgcaaa tcaaactagc gagaggagtc gataccacga    15960
aaatcccatg taggagacgc tccagcaatc ccatgccttc gatgcaagtg attgccatta    16020
gtaaatctgg gaatggctaa tggccccac aagacactag ttgtcactac acagccaggg    16080
ccgcaataag ccgccacaaa ctccggtgaa catgatccgc aacctagcat cgtcggcact    16140
gcaaccgtgc accaccaccg ccatgccgca atgtagcgat gatcaccgct acccgccagc    16200
acgcaagcaa ccagcgaaat cacaaccaac cacggactcg ccaaccaggc caagctccaa    16260
tataatgccc cgaaggagga acacagacgc cgagcaccgc catcattcga tctgggcaaa    16320
ccggaaccta gggtttccgc taaagcatta tgagagaata gtcaaggact gcatctagac    16380
accttaagca agggaacgac atccgcaggc gccaccgtca ttggcttcga ccgagcgaag    16440
cctagctttc accgacagtc ccatccctcc ttccccaaat cgaacctagc cactctacca    16500
tgcccaccac cgccgccaac atgaccacta gtgaaggaga ccaccaagtc cacagaccct    16560
```

```
aggccaagat tcatggctaa ggtgccgcat gccttgttgc aagagaagag catgccatgc    16620
ccccacatcg tcgggatccg ctatcgagga agagtcatcg ttccactaat ccacaacaat    16680
ctactgcacc gcaaagaagg tggtcgcgac cacgacgatg tgtcacatgg acctctgtac    16740
cgagaggtgc cgtcattgtc gggagaaaag gtcgtcctgc caatgaacct gatggaaaaa    16800
cgtcatgcga ggagccctgt cggtgcctcc gacaacggtg agaaggtatg ggacgtggag    16860
ggctgctggc ggcgagtcta ggtggtttcg cccatgacgc ctggaagatc atgcgagggt    16920
tagggatggc tggaaggcaa tgcaggggac aatacaatta taacacatta gttcgaagaa    16980
tcggctatga gttgattggc acaaaagaga tggttcttgg catcgagtct catggtggat    17040
gtgttgttag gcatatcagc atgagttgtc gatagtacgt cagtacgtcc cctagagctt    17100
tgtgcactac taggtggagc catgctaaga gcatctccaa cagatgacat ataatagggc    17160
actaaagagt aggttttaag gcaccaaaaa agattctgcc atagcagacg atgtaaaata    17220
ggtcaccgga aaaatttctg ccgtagtagg gcaatattat tgcatatttc gacatttttca    17280 aacttctaat tgttcaaagt taaactaaca gtactaagat agatacacta ctcatcatca    17340
ctactacgat agaggtctca agtcaatatc gtcggctttg tcatcgtcca actcaagctt    17400
gatcacctgt gaggggccag cctcatcctc ctccttgaga accttcttgt gttgcacgtc    17460
cctactggca aagaattcgt attccacctg cacaaggtaa ggactttccg ctgcgaacct    17520
tgccatagcc accgcatcgc tctcatgggc ggtgtgttgc tccacgatga ggcaaccatc    17580
ttctcctcgt gaaacacaat ccccaattca ggagcgagga actccgccac ctctcgctca    17640
tgacgtcagg aaagtgtgct ctgacttggg ccagcggcca cggcatcata cgcgcatgta    17700
gcgagctctg ttgtcttgaa ggtcctgagc cagacttgca tcccatcgca caagatatcg    17760
acagcatagc cgtgggacta caatgccaaa cacagtggaa gaccgtgctc ctcctcgcct    17820
tagcgttgtg gcgcaacatc ttcagctcgg cgatggcggt ggtcgacggc tgagacgaat    17880
gagagcggtg gatctggcgg cagtggcggc caaatgcgt ggtgtggcag acaatttggt    17940
caacgtggtg gtgcagaggc cgattcgaca aaaggggcgg ctgttccgat ggcggtggtg    18000
gccgtattgg gcatcgtcgt cggcaaggca gaggaagcga ctaggggggt tcacgcggcg    18060
gtcgagcaaa gcgcggctga ggttttttgtt ttgcggcaac tacgcggctg ttgtatattt    18120
ggagaacaaa agggctgccc caaaaatatt ctagcacgat ataggggatag ggcatctgct    18180 ggagcaccat tttgggtcca aatgccataa aacggttttt taggcagctg cccatttttgc    18240 atcatctggt agagatgctc taagagtttt tagccttttta tgggcttctc ttgttctatg    18300
ttttacgaac atgcttttta cctatgttta tgttcataac gtggttaggt ctatttaagc    18360
cccctaaact atacagtaat aaatattttt tcccgaatct tttgttcgga caatcaacac    18420
ccctacaggc ttatacgtga aacggtttgg ttgagtccct aactacgcca catgggcttg    18480
ttttgttgat gtagaaatga ttaaagacaa gactcaaatt gtacatctct ccttttctttt    18540 catgatgttg cccaatgatt taatatacgg tcacacgatg ataagcgacc gcctatacta    18600
aaaagaaatg gattgtgcta tttctcccaa tcgcccaaac cctcgatgaa aggttttcct    18660
tctccaaatc atcaacttgg ccatagtaaa cacaaactca agctctttcg ctagggatat    18720
aaatggccca aataatgtgt cccttttctac actagataat ggcctaatgc cccatttatc    18780
aatgcaagtg ttattcataa catggtatca acaacatctt ttgagttttt ctaaggtttc    18840
tttttggatc atcaaacat                                                  18859
```

<210> SEQ ID NO 4
<211> LENGTH: 1402
<212> TYPE: PRT
<213> ORGANISM: Triticum aestivum cv Renan

<400> SEQUENCE: 4

```
Met Glu Gly Leu Ala Arg Glu Thr Asn Pro Ser Ser His His Gln Asp
1               5                   10                  15

Phe Thr Ala Cys Ala Ser Asp Glu Arg Pro Asp Glu Ser Glu Leu Glu
            20                  25                  30

Leu Ala Ser Arg Gln Arg Gln Asn Gly Ala Ala Asn Thr Glu His Val
        35                  40                  45

Ser Glu Asn Met Leu Leu Asp Ser Ser Lys Leu Gly Ala Leu Lys Arg
    50                  55                  60

Arg Glu Phe Phe Asp Asn Leu Leu Lys Asn Leu Glu Asp Asp His Leu
65                  70                  75                  80

Arg Phe Leu Arg Gly Gln Lys Glu Arg Ile Asp Arg Val Asp Val Lys
                85                  90                  95

Leu Pro Ala Ile Glu Val Arg Tyr Asn Asn Leu Phe Val Glu Ala Glu
            100                 105                 110

Cys Arg Val Thr Lys Gly Asn His Leu Pro Ser Leu Trp Asn Ser Thr
        115                 120                 125

Lys Gly Ala Phe Ser Gly Leu Val Lys Leu Leu Gly Phe Glu Thr Glu
    130                 135                 140

Arg Ala Lys Thr Asn Val Leu Glu Asp Val Ser Gly Ile Ile Lys Pro
145                 150                 155                 160

Cys Arg Leu Thr Leu Leu Gly Pro Pro Gly Cys Gly Lys Ser Thr
                165                 170                 175

Leu Leu Arg Ala Leu Ala Gly Lys Leu Asp Lys Ser Leu Lys Val Thr
            180                 185                 190

Gly Asp Ile Ser Tyr Asn Gly Tyr Glu Leu His Glu Phe Val Pro Glu
        195                 200                 205

Lys Thr Ala Val Tyr Ile Asn Gln His Asp Leu His Ile Ala Glu Met
    210                 215                 220

Thr Val Arg Glu Thr Leu Asp Phe Ser Ala Gln Cys Gln Gly Val Gly
225                 230                 235                 240

Arg Arg Pro Lys Ile Leu Lys Glu Val Asn Thr Arg Glu Ser Val Ala
                245                 250                 255

Gly Ile Ile Pro Asp Ala Asp Ile Asp Leu Tyr Met Lys Val Val Ala
            260                 265                 270

Val Glu Ala Ser Glu Arg Ser Leu Gln Thr Asp Tyr Ile Leu Lys Ile
        275                 280                 285

Met Gly Leu Glu Ile Cys Ala Asp Thr Met Val Gly Asp Ala Met Arg
    290                 295                 300

Arg Gly Ile Ser Gly Gly Gln Lys Lys Arg Leu Thr Thr Ala Glu Met
305                 310                 315                 320

Ile Val Gly Pro Ala Ser Ala Tyr Phe Met Asp Glu Ile Ser Asn Gly
                325                 330                 335

Leu Asp Ser Ser Thr Thr Phe Gln Ile Ile Asn Cys Phe Gln Gln Leu
            340                 345                 350

Thr Asn Ile Ser Glu Tyr Thr Met Val Ile Ser Leu Leu Gln Pro Thr
        355                 360                 365

Pro Glu Val Phe Asp Leu Phe Asp Asp Leu Ile Leu Met Ala Glu Gly
    370                 375                 380
```

```
Lys Ile Ile Tyr His Gly Pro Arg Asn Glu Ala Leu Asn Phe Phe Glu
385                 390                 395                 400

Glu Cys Gly Phe Ile Cys Pro Glu Arg Lys Ala Ala Ala Asp Phe Leu
        405                 410                 415

Gln Glu Ile Leu Ser Trp Lys Asp Gln Gln Gln Tyr Trp Leu Gly Pro
            420                 425                 430

His Glu Ser Tyr Arg Tyr Ile Ser Pro His Glu Leu Ser Ser Met Phe
        435                 440                 445

Arg Glu Asn His Arg Gly Arg Lys Leu His Glu Gln Ser Val Pro Pro
    450                 455                 460

Lys Ser Gln Leu Gly Lys Glu Ala Leu Ala Phe Asn Lys Tyr Ser Leu
465                 470                 475                 480

Gln Lys Leu Glu Met Phe Lys Ala Cys Gly Ala Arg Glu Ala Leu Leu
            485                 490                 495

Met Lys Arg Asn Met Phe Val Tyr Val Phe Lys Thr Gly Gln Leu Ala
        500                 505                 510

Ile Ile Ala Leu Val Thr Met Ser Val Phe Leu Arg Thr Arg Met Thr
    515                 520                 525

Ile Ser Phe Thr His Ala Asn Tyr Tyr Met Gly Ala Leu Phe Phe Ser
    530                 535                 540

Ile Phe Met Ile Met Leu Asn Gly Ile Pro Glu Met Ser Met Gln Ile
545                 550                 555                 560

Gly Arg Leu Pro Ser Phe Tyr Lys Gln Lys Ser Tyr Tyr Phe Tyr Ser
            565                 570                 575

Ser Trp Ala Tyr Ala Ile Pro Ala Ser Val Leu Lys Val Pro Ile Ser
        580                 585                 590

Ile Leu Asp Ser Leu Val Trp Ile Ser Ile Thr Tyr Tyr Gly Ile Gly
    595                 600                 605

Tyr Thr Pro Thr Val Ser Arg Phe Phe Cys Gln Phe Leu Ile Leu Cys
    610                 615                 620

Leu Leu His His Ser Val Thr Ser Gln Tyr Arg Phe Ile Ala Ser Tyr
625                 630                 635                 640

Phe Gln Thr Pro Ile Val Ser Phe Phe Tyr Leu Phe Leu Ala Leu Thr
            645                 650                 655

Val Phe Leu Thr Phe Gly Gly Phe Ile Leu Pro Lys Thr Ser Met Pro
        660                 665                 670

Gly Trp Leu Asn Trp Gly Phe Trp Ile Ser Pro Met Thr Tyr Ala Glu
    675                 680                 685

Ile Ser Ile Val Ile Asn Glu Phe Leu Ala Pro Arg Trp Gln Lys Glu
    690                 695                 700

Ser Ile Gln Asn Ile Thr Ile Gly Asn Gln Ile Leu Val Asn His Gly
705                 710                 715                 720

Leu Tyr Tyr Ser Trp His Tyr Tyr Trp Ile Ser Phe Gly Ala Leu Leu
            725                 730                 735

Gly Ser Ile Leu Leu Phe Tyr Ile Ala Phe Gly Leu Ala Leu Asp Tyr
        740                 745                 750

Arg Thr Pro Thr Glu Glu Tyr His Gly Ser Arg Pro Thr Lys Ser Leu
    755                 760                 765

Cys Gln Gln Glu Lys Asp Tyr Thr Ile Gln Asn Glu Ser Asp Asp
    770                 775                 780

Gln Ser Asn Ile Ser Lys Ala Lys Val Thr Ile Pro Val Met His Leu
785                 790                 795                 800

Pro Ile Thr Phe His Asn Leu Asn Tyr Tyr Ile Asp Thr Pro Pro Glu
```

```
            805                 810                 815
Met Leu Lys Gln Gly Tyr Pro Thr Arg Arg Leu Arg Leu Leu Asn Asn
            820                 825                 830

Ile Thr Gly Ala Leu Arg Pro Gly Val Leu Ser Ala Leu Met Gly Val
            835                 840                 845

Ser Gly Ala Gly Lys Thr Thr Leu Leu Asp Val Leu Ala Gly Arg Lys
            850                 855                 860

Thr Gly Gly Tyr Ile Glu Gly Asp Ile Arg Ile Gly Gly Tyr Pro Lys
865                 870                 875                 880

Val Gln Glu Thr Phe Val Arg Ile Leu Gly Tyr Cys Glu Gln Val Asp
                    885                 890                 895

Ile His Ser Pro Gln Leu Thr Val Glu Glu Ser Val Thr Tyr Ser Ala
            900                 905                 910

Trp Leu Arg Leu Pro Ser His Val Asp Glu Gln Thr Arg Ser Lys Phe
            915                 920                 925

Val Ala Glu Val Leu Glu Thr Val Glu Leu Asp Gln Ile Lys Asp Val
            930                 935                 940

Leu Val Gly Ser Pro Gln Lys Asn Gly Leu Ser Met Glu Gln Arg Lys
945                 950                 955                 960

Arg Leu Thr Ile Ala Val Glu Leu Val Ser Asn Pro Ser Ile Ile Leu
                    965                 970                 975

Met Asp Glu Pro Thr Thr Gly Leu Asp Thr Arg Ser Ala Ala Ile Val
            980                 985                 990

Ile Arg Ala Val Lys Asn Ile Cys Glu Thr Gly Arg Thr Val Val Cys
            995                 1000                1005

Thr Ile His Gln Pro Ser Thr Glu Ile Phe Glu Ala Phe Asp Glu
        1010                1015                1020

Leu Ile Leu Met Lys Ser Gly Gly Lys Thr Ile Tyr Ser Gly Pro
        1025                1030                1035

Ile Gly Glu Arg Ser Cys Lys Val Ile Glu Tyr Phe Glu Lys Ile
        1040                1045                1050

Ser Gly Val Pro Lys Ile Lys Ser Asn Cys Asn Pro Ala Thr Trp
        1055                1060                1065

Met Met Asp Val Thr Ser Thr Ser Met Glu Val Gln His Asn Met
        1070                1075                1080

Asp Phe Ala Ile Leu Tyr Glu Glu Ser Ser Leu His Arg Glu Ala
        1085                1090                1095

Glu Asp Leu Val Glu Gln Leu Ser Ile Pro Leu Pro Asn Ser Glu
        1100                1105                1110

Asn Leu Cys Phe Ser His Ser Phe Ala Gln Asn Gly Trp Ile Gln
        1115                1120                1125

Leu Lys Ala Cys Leu Trp Lys Gln Asn Ile Thr Tyr Trp Arg Ser
        1130                1135                1140

Pro Gln Tyr Asn Leu Arg Arg Ile Met Met Thr Val Ile Ser Ala
        1145                1150                1155

Leu Ile Tyr Gly Ile Leu Phe Trp Lys His Ala Lys Val Leu Asn
        1160                1165                1170

Asn Glu Gln Asp Met Leu Ser Val Phe Gly Ala Met Tyr Leu Gly
        1175                1180                1185

Phe Thr Thr Ile Gly Ala Tyr Asn Asp Gln Thr Ile Ile Pro Phe
        1190                1195                1200

Ser Thr Thr Glu Arg Ile Val Met Tyr Arg Glu Arg Phe Ala Gly
        1205                1210                1215
```

```
Met Tyr Ser Ser Trp Ser Tyr Ser Phe Ala Gln Ala Phe Ile Glu
    1220            1225                1230
Ile Pro Tyr Val Phe Ile Gln Val Val Leu Tyr Thr Leu Ile Val
    1235            1240                1245
Tyr Pro Ser Thr Gly Tyr Tyr Trp Thr Ala His Lys Phe Leu Trp
    1250            1255                1260
Phe Phe Tyr Thr Thr Phe Cys Ser Ile Leu Ser Tyr Val Tyr Val
    1265            1270                1275
Gly Leu Leu Leu Val Ser Ile Thr Pro Asn Val Gln Val Ala Thr
    1280            1285                1290
Ile Leu Ala Ser Phe Phe Asn Thr Met Gln Thr Leu Phe Ser Gly
    1295            1300                1305
Phe Ile Leu Pro Ala Pro Gln Ile Pro Lys Trp Trp Thr Trp Leu
    1310            1315                1320
Tyr Tyr Leu Thr Pro Thr Ser Trp Ala Leu Asn Ala Leu Leu Thr
    1325            1330                1335
Ser Gln Tyr Gly Asn Ile Glu Lys Glu Val Lys Ala Phe Gly Glu
    1340            1345                1350
Thr Lys Ser Val Ser Ile Phe Leu Asn Asp Tyr Phe Gly Phe His
    1355            1360                1365
Gln Asp Lys Leu Ser Val Val Ala Ala Val Leu Val Ala Phe Pro
    1370            1375                1380
Phe Val Leu Ile Ile Leu Phe Ser Leu Ser Ile Glu Lys Leu Asn
    1385            1390                1395
Phe Gln Lys Arg
    1400

<210> SEQ ID NO 5
<211> LENGTH: 4209
<212> TYPE: DNA
<213> ORGANISM: Triticum aestivum cv Renan

<400> SEQUENCE: 5
atggagggcc tcgcaagaga gaccaaccca tcatcccacc atcaagattt caccgcctgt     60
gcgagtgacg agcgcccgga tgagtccgag ttagaattgg catcgcgaca cgccagaat    120
ggtgctgcaa acaccgagca tgtgagtgag aacatgctgc ttgacagcag caagttggga    180
gctctcaaga ggcgcgagtt cttcgacaac ctgctaaaga acctcgaaga cgaccacctc    240
cgctttctgc gcggacaaaa ggaaagaatt gacagggttg atgtcaagtt gccagcaata    300
gaggtgaggt ataataatct gtttgtggag gcagagtgca gagttactaa aggaaatcac    360
ctgccatctc tatggaatag taccaaaggt gccttctcgg gcctcgtgaa gttgctaggc    420
ttcgaaacgg aaagagcaaa aaccaacgtt cttgaagatg tcagtggaat catcaaaccc    480
tgcagattga ctcttctact gggacctcct ggatgtggca aaagcactct gttgcgagct    540
cttgccggga aactagataa atctctaaag gtaacagggg atatctctta taatggttat    600
gaacttcatg aatttgtacc tgagaaaaca gctgtgtata tcaaccaaca tgatctgcac    660
atagctgaga tgactgtgag ggaaacttta gacttctcag cccagtgcca aggtgttgga    720
agaagaccaa aaatactcaa ggaggtgaac acaagggaga gtgtggctgg gatcatacct    780
gatgcggaca tcgatctata catgaaggta gtagcagttg aagcttcaga gcgaagccta    840
cagacagatt atattttgaa gatcatgggg ctagagatat gcgcagacac gatggttggg    900
gatgcaatga agaggaat atcagggggg cagaagaaaa gattaaccac agccgagatg    960
```

```
attgtgggcc ccgcaagtgc atactttatg gatgaaatat caaatggtct ggatagctct    1020 accactttc aaataatcaa ttgtttccag caactgacaa acatcagcga gtacacgatg    1080
gttatttcac ttcttcaacc aacacctgag gtatttgatc tttttgatga cctcatacta    1140
atggcagaag ggaagattat ctaccatggc cctcgaaatg aagctctcaa ttttttttgag    1200 gagtgtgggt tcatatgccc agaaagaaaa gcggcagctg actttcttca agagatcttg    1260
tcctggaagg accaacaaca gtactggttg ggtccacatg aatcatacag atatatctca    1320
cctcatgaat tatcaagcat gttcaggag aatcacaggg ggagaaaact acatgaacaa    1380
agtgtacctc ccaaaagcca gttgggcaag gaagctttag cattcaataa gtattcgcta    1440
caaaaactgg aaatgttcaa agcctgtgga gcaagggaag cactcctaat gaaaaggaat    1500
atgtttgttt atgtcttcaa aacaggccag cttgccatta ttgcactcgt aacaatgtct    1560
gtattccttc gaactcgcat gacaataagt ttcactcatg caaattacta tatgggagca    1620 ttatttttt ccatcttcat gattatgtta aatggcatac cagagatgag catgcagatt    1680
gggagactcc caagttttta caagcaaaag agctactatt tctattcatc atgggcatat    1740
gcaataccag cttcagtcct aaaggtccct atttccatac tggattcgct tgtatggata    1800
tctatcacat attatggtat tggttataca cctactgttt caaggttctt ctgccagttt    1860
ctgatacttt gtcttctcca tcattcagtc acctcgcagt atcgatttat tgcttcatac    1920
ttccaaacac ctattgtgtc tttcttctac ctttttcttg ctctaacagt attccttaca    1980
ttcggaggct tcattcttcc caagacctcc atgccaggat ggttaaactg gggattttgg    2040
atatctccaa tgacatatgc agaaatcagc atagttatta acgaattctt ggcaccaaga    2100
tggcagaagg aaagtattca aaacataaca attgggaacc aaatcctggt taatcatggc    2160
ctatattaca gttggcatta ttattggata tcctttggag ccttgcttgg atctattctc    2220 ttatttttata tcgcttttgg attggcacta gattacagaa cacctacaga agaatatcat    2280
ggaagcaggc ctacaaagag cttatgtcaa cagcaggaaa aagattacac tattcaaaat    2340
gaatctgatg atcaatcaaa tatttccaaa gcaaaggtga ctataccagt tatgcatctt    2400
ccaattacat tccacaatct gaactactac attgataccc caccggaaat gctgaaacaa    2460
ggctatccaa caagaagact tcgactgctt aataacataa ctggtgcttt acgtcccggt    2520 gttcttctg cactaatggg tgttagtgga gctgggaaga caactctact agatgtatta    2580
gcaggaagga aaacaggagg ttatattgaa ggggacataa aataggtgg atatcccaag    2640 gtgcaggaaa catttgtcag aatcttgggt tactgcgaac aagtcgacat acattcccca    2700
cagcttacag ttgaagagtc tgtaacttat tctgcgtggc ttcgtctgcc ttctcatgtc    2760
gacgaacaaa caagatctaa atttgttgct gaagtccttg aaactgttga actagatcaa    2820
ataaaagatg tcttagtggg gtcaccacag aaaaatggat tgtccatgga gcagagaaag    2880
aggctaacga ttgcagtcga gcttgtttca aacccatcaa tcatactaat ggatgaacca    2940
acaacaggtt tagatacaag gtcagcagcc attgttattc gtgcagtcaa aaatatttgt    3000
gaaacaggaa ggacagtagt ctgtacaatc catcagccga gcactgaaat ttttgaggca    3060
tttgatgagc tcatattaat gaaagcggt gggaaaacaa tctacagtgg accaatagga    3120
gagcgctcct gcaaagtgat cgagtacttt gagaaaattt ctggagtccc aaaaataaag    3180
agtaactgca atccagctac ttggatgatg gatgtaacat cgacatcaat ggaggttcaa    3240
cacaatatgg actttgcaat tttgtatgaa gagtcgtcac tgcatagaga agctgaagat    3300
```

| ctagtggagc agctaagtat cccattacca aattcagaaa atctatgttt ctcccatagt | 3360 |
| tttgcacaga atggctggat tcaacttaaa gcttgcttgt ggaaacaaaa cataacttac | 3420 |
| tggagaagtc ctcagtataa cttgaggcgc attatgatga ctgtcatatc tgccctgatc | 3480 |
| tacggaatat tgttctggaa gcatgcaaaa gtattaaaca acgagcagga catgctcagt | 3540 |
| gttttggtg caatgtattt gggtttcacc accataggcg cttataatga tcagacaatc | 3600 |
| ataccattca gtacaactga gcgtattgta atgtatcgtg agagatttgc aggaatgtat | 3660 |
| tcatcttggt catattcatt cgcacaggct ttcattgaga tacectatgt atttatccaa | 3720 |
| gtggtactgt atacgttaat tgtctatccg tcaactggtt attattggac agcacacaaa | 3780 |
| ttcctatggt tcttctacac cacattttgt tcaattctct cctatgttta tgttgggttg | 3840 |
| cttcttgttt ccataaccec caatgttcaa gtagctacca tactggcttc atttttcaac | 3900 |
| accatgcaaa cactattctc aggatttatt ttacctgcac ctcaaatccc gaagtggtgg | 3960 |
| acttggctct actatctcac tcctacatct tgggcactca atgccctctt gacatcacaa | 4020 |
| tacgaaaaca tagaaaaaga ggtgaaagca tttggagaaa ctaaatcagt ttcaatcttc | 4080 |
| ttgaatgact attttgggtt tcatcaagat aagttgagcg tagtagcagc tgtcctcgtt | 4140 |
| gcctttcctt ttgtgttgat aatcttgttt tcgttgtcca ttgagaaact taattccag | 4200 |
| aagaggtaa | 4209 |

<210> SEQ ID NO 6
<211> LENGTH: 15120
<212> TYPE: DNA
<213> ORGANISM: Aegilops tauschii

<400> SEQUENCE: 6

| gcagccaact cgagatataa ctagaaggca tctggagcgt cggtctcgag ctgttacaca | 60 |
| ctcgctcacc gggcccctcc tagcgccctc aacaacctt gacctccccc ccaacggtgg | 120 |
| taccagacgc cccggaacta gccgcactcc cccccccccc tccgaatggg ggcaacgaaa | 180 |
| acaaggggca cccaggcgcc aagaataaga agagagggcc ggtgcgctcc gctaggtacc | 240 |
| aacaggctca ccctccctcc gcggccgttg ttgcctccat cgagccagcc gccgactccg | 300 |
| accacgatgg ccggccttgc ttcaactgtg tgatccccgg ttacttccaa gtcgcatgcc | 360 |
| ccaatcgtcc gatgtgctac ttgtgtaagg atcccgggca tcccgctctg ttgtgcttga | 420 |
| accggtcggt tcggaggag ttgatgatgt acgggcacgg cccaggggc atgcgcttct | 480 |
| tccacatcaa ggtcccggat gccccacccc ctgcgaaaag atcagatcta ttataaagat | 540 |
| tcaccagaag tacaaaacac ctcaaaacat aataaaattt acatcaaggt ccatggagga | 600 |
| atggaccacc gaacgccat tgcctcagcc agaaccgagc cgccgacacg ccgctatcga | 660 |
| cgctcccata ccggagccgg tctgaccttg tcgatgatag ccgaaaagtc ttcgtgtgcg | 720 |
| tgcccttaag gatcagcgtc ccagagccgc agtcgtcacc gttgaatcct tgaatcagtc | 780 |
| taaagaattt gacaccaaat atcgccgttg cgtacgcacg gcgagaaact ctaacctctc | 840 |
| cgccccgagg agctggcaga atctacgcc gaagctccgt ctaatccgtc ctagaggacg | 900 |
| aacttgagga ggatcggaac ccgaaagact gactcgaaga agaagcgccg ccatccgtcc | 960 |
| aaacgccgcc cctgcgagaa ctaaaactct acctgtctac tagccggaga caaggcacca | 1020 |
| gaaatcccct ccctgccacc agccgccgga acgcaggcg gagggaaggg gaatccacgg | 1080 |
| gctcgccgat gaagatcaag gggaggaagg ctttcacga caggggaaag aaaagcaatc | 1140 |
| ttaatctttt atatctttac aaccaaaatt ccaaattgag ttttggttcc atattcatgt | 1200 |

```
ttctattaca agggctttaa ataatatcca tttttaatac gatttgatga gttttttaaaa    1260
cttcattaag ttgcagctgc tgaaacttgg taccagcaag cgacaaaatc atgaaacttg    1320
atgcgagcga atggcaaaat cgtaagtttc aaaaactgaa acttaaaact tgatgtgccg    1380
tcgtgcggaa ccatcgagca gccgggcagg tgcgtgccac gcgcctgcgt gcccctgcga    1440
gttttccgcg caagagcgcg aacaaacggt actgcacata ttgcagtttc aagttgccga    1500
gtgcgactct gtggtcaatg tcgtcgaagg ctctttcatc aagtaattac aataccattt    1560
caactttcat gggtccgtgc ctgccaggtt caaagttcca agatggttat gtgcaaccga    1620
ctgtgtgtcc cacatccaca catcgaagca gaggtctcgt gaagtctttc caaacgagca    1680
agagcaacat caaggacgac cagcggaggg ggtctttcca aacgagtggt ttctatcctc    1740
ccgtagaatg ggtgatccac gacaagtcta tgagtcgttc tgaggttgag actaataaat    1800
taattgtggc taatcgacac tagtcgacac cgaagttgct actcacagac tagtcgacac    1860
tgaagtgtag tcggccccgg agttgtgact tctagactag tctatagact tgtccttcga    1920
ctcataatcc atgctcgtca tccagccccc attaacccca tccatgtgac tccctgcgta    1980
acataacctg ttcggttact cccctttctaa tccatgacta aaattgcact tcaatctttt    2040
tccgaagtcc cgttttgcgg tggcatatat ccaatttaca agctaaaaaa aagtgcggtg    2100
gggttctttc ccgtcacaaa gaaaacccaa aataaggcaa atcaggtctc cgaatcagga    2160
gtactgtgaa gtcttcacca gtaccatata atacatgact tatggctgtc atcttccaga    2220
atgtgcgttt ccatgctaat agttagtttg aagtcaacac atgactggtc tttccaactc    2280
ttctgactga tgatgtccgt atgggaaaaa gcgtgcgtac atgctcgcca aaaccttata    2340
tatgtactct aaagagaagg aaatgactgc ttagagtacg gctaggcaat agcaaagggc    2400
gtcgatttaa ctcacccatc ttgagatgga gggcctcgca agagagacca acccatcatc    2460
ccaccatcaa gatttcaccg cctgtgcgag tgacgagcgc ccggatgagt ccgagttaga    2520
attggcatcg cgacagcgcc agaatggtgc tgcaaacacc gagcatgtga gtgagaacat    2580
gctgcttgac agcagcaagt tgggagctct caagaggcgc gagttcttcg acaacctgct    2640
aaagaacctc gaagacgacc acctccgctt tctgcgcgga caaaaggaaa gaattgacag    2700
gcatgttttc ttttttcagaa cactgttcta agtaactgga tgaagattag actctgttta    2760
tgcaactgtt tattttttccc ctgtgatcca tttccacagg gttgatgtca agttgccagc    2820
aatagaggtg aggtataata atctgtttgt ggaggcagag tgcagagtta ctaaaggaaa    2880
tcacctgcca tctctatgga atagtaccaa aggtgccttc tcggtaagaa acctctgaaa    2940
tgattgattt ttattatgca ccaaatagca gcatctgaag caactgtttt ttcgacgaat    3000
cataaatgga actgataaga cacagatata tgttggatgg tattgactaa cttacccgtt    3060
ttcatttgag ttacagggcc tcgtgaagtt gctaggcttc gaaacggaaa gagcaaaaac    3120
caacgttctt gaagatgtca gtggaatcat caaaccctgc aggtatgtgc catgtttcat    3180
gagtgtttag tataaaaatg gaaagaaac cataaacata caaagaaaa cgtgcgaaat     3240
ttagtgcatc aagtgtctgt agttcttgct ttagagatta aggttagttc tgattccata    3300
tgttcccatc tttgtagatt gactcttcta ctgggacctc ctggatgtgg caaaagcact    3360
ctgttgcgag ctcttgccgg gaaactagat aaatctctaa aggtacaaat actgtcttcc    3420
tttcataatt aaagaaaaaa gcatgtcctt gttttcactg attgcatctg ctcctataaa    3480
gatctcaaga ttactcaata cttggccaaa tgaaagaaca aaaaaattaa gatctcaacc    3540
```

```
agctgcacac cgcagtaaac tgctctctgt cctctggccg ctacataata gaccacatat   3600
gaagccagta cacaaataaa tgtataacct acaatctttt ctcaaagtct acatcattca   3660
tgaatagcca aagagccaaa cttaagtttt tatcaatacc ccacaaacaa taaactcgcg   3720
cctcttgaga gctccgaact tgctgctgtc aagcagcaag ttctcacgca catgctcaaa   3780
tgtttgcagc accattctgg cgccgtcgca ctgacaattc taactcggac tcgtcgggac   3840
cctcgtggtc atacgccagc gctcccaaat cctgatacca aacagataa tgacgctgac    3900 gctgccagag gagacggcgc aattgcctta atcctcggca catagtgtcg caacacatac   3960
atgtgcccaa ctactcctcg gcaccacgcc cgcggagga caagccggcg ctcctgtccc    4020
ctaaccatga caccgacatc aagaacctcc gcctagaact cttgcacaac ctcctccgtc   4080
ttctggtgac agaaacgcgc caccggtgac acaaagccac cgtcatccgc atatgaccca   4140
acctccagca gcatcctgag attcaacaca tgacacctcc gctgccctct cctccatggc   4200
atcctcggca gccaggaaag ataatctcaa tccgctggat ccccctaaag taggcgtcta   4260
ggcgatcact gtggcggcag ggtgagtcac cttcagggca gcgctctcat ccaattccta   4320
tgtaggtttg ctactactgc acggggacct atcagatgta tctcacagac caattagata   4380
aatcgatggt cgaatttgga agttataatg agatacactg ttgtgattaa atttgatcac   4440
gctatattgt agaggaaagt gtaattccct tgaaatgaac aacatgcaac atagtagtat   4500
agaatcgccg caaattttcc ttgcgtttgg atataaaact caggcccatg ttccatcttt   4560
ttaactgtgt atatgcccta gcagcgtgaa catactactg gtcctgctag aacaagcggc   4620
gggtaaagat gggcgcctgc ttcatacttg ccagtaaatt aggatgattg ccttgcagaa   4680
aatatggcca atattaccat taagcctatt taccgaaatc taacacaaac ttttgactgt   4740
aggaaacaaa gaatcaattc tactaacaga ttttttctttt gttcgagaaa atgcttatgc   4800
gtgtgtcgat gcattaaaag gaaagagaat aacagccatt caggattaca agccctaaga   4860
aggaccatgg aactcctgaa ccaaggttac acgccaggca ggaggagctg gagttttgcc   4920
gcacgggcga aacccagcaa gtcgcctccg tgctacgcta ggtctagcca tactgaagga   4980
tacatcattg tgatgagcac caggccgtca tctgaatgag tgtcagacaa ctgacagaat   5040
aacattactc acatcaaaag caaaagttgt ccatcacctc agagtctatg gttttcatta   5100
gttgcacatg gttaacgacc tctgacaaag gcagaaattc aagaatgcct tgcactgaac   5160
gacggatatc agtatactta agttgctttt ttacagcacc aactgatgct ggagttatca   5220
aattgaaatg tcccaactcc ccagcaaagc cacctatatt gtctccaaaa catataattg   5280
ttggcatggt ttccacctgt atgaaaccgg cactatttac tggctcaaat gagtagttcg   5340
tcatgaagct agtacttata ctgactgctg aatactaata ataacagct  tttaattatt   5400 ttcagaccaa gtactttcag agaaaactat tttcagatca gcttctaatt aatactccct   5460
cagttccaaa atataaggtg tattagtttt tcaagaggc attcatgttt gaccaagttt    5520
ttagaaaaaa aatatcaata tctacaatac caaatttgta tgattagatt tatcacgaaa   5580
agtatttttc atattttatt tattttatat tgcagaatgt taatattta ttctataatc     5640 ttggtcaaac atacataagt ttgacttgca cgaaacactga tgcaccttat attctggaac  5700
ggagggagca aataacagca cacaatagat tatgggtacc tgctgggtat tcctgcttag   5760
agatacaacc acagaaaagc agagcagaac agcacaaatg cccttttagcc attgacacta  5820 caattagttt caaagctaca attttgcaaa atcatgaaca aagaagaaa  aaaaatggca   5880 aactgaatgt aacgatgcaa gcttttacag gtaacagggg atatctctta taatggttat   5940
```

```
gaacttcatg aatttgtacc tgagaaaaca gctgtgtata tcaaccaaca tgatctgcac    6000
atagctgaga tgactgtgag ggaaacttta gacttctcag cccagtgcca aggtgttgga    6060
agaagaccaa gtaagtctat tggacagtcc tcacaagaat tcatgatcaa aaataagttc    6120
ttaaataatc acaacatttg ttgctcacta aatttgtttg cccaaagaaa tactcaagga    6180
ggtgaacaca agggagagtg tggctgggat catacctgat gcggacatcg atctatacat    6240
gaaggtaaaa aatcgtgtct cctatgtact ggctggcatt atcctttctc actttacaat    6300
taaaaaaaaa acagacctgc ttatctgagt tacaagaaaa aggtaattca acgtcgaatg    6360
aatattggaa ctgctctagc agaataatat ttggttgtat taaagctaag ctagcttttc    6420 aattttttcat tagtcaacac ttctgtttct gtttctacaa attaaacgta actgtttttc    6480
aaaagtaaag cggctaatgc aggtagtagc agttgaagct tcagagcgaa gcctacagac    6540
agattatatt ttgaaggtac cccttgccaa acatctaag tttatgcata acttggtgct    6600
gaaggcagat aggaacaaga tactaacaga atcacaatac tgatttattt gtagatcatg    6660
gggctagaga tatgcgcaga cacgatggtt ggggatgcaa tgagaagagg aatatcaggg    6720
gggcagaaga aaagattaac cacaggtata gtaaacccaa tgggaaatac attaaccaac    6780
aagggatcac cttgtatata atctttcacc tacttgtacc agccgagatg attgtgggcc    6840
ccgcaagtgc atactttatg gatgaaatat caaatggtct ggatagctct accactttc    6900 aaataatcaa ttgtttccag caactgacaa acatcagcga gtacacgatg gttatttcac    6960
ttcttcaacc aacacctgag gtatttgatc ttttttgatga cctcatacta atggcagaag    7020
ggaagattat ctaccatggc cctcgaaatg aagctctcaa ttttttttgag gagtgtgggt    7080 tcatatgccc agaaagaaaa gcggcagctg actttcttca agaggtaatt gttctcaatc    7140
acaaaaataa ctgcagcaac tgagatgatt tgcacgttga tgaaaccagt ttttttttct    7200
aattttgaaa tcattagatc ttgtcctgga aggaccaaca acagtactgg ttgggtccac    7260
atgaatcata cagatatatc tcacctcatg aattatcaag catgttcagg gagaatcaca    7320
gggggagaaa actacatgaa caaagtgtac ctcccaaaag ccagttgggc aaggaagctt    7380
tagcattcaa taagtattcg ctacaaaaac tggaaatgtt caaagcctgt ggagcaaggg    7440
aagcactcct aatgaaaagg aatatgtttg tttatgtctt caaaacaggc caggttaaac    7500
ttcattctga ggcactcttt cctgtacaaa gtaaattatg agtccaaact gagatttact    7560
ccttgatgca gcttgccatt attgcactcg taacaatgtc tgtattcctt cgaactcgca    7620
tgacaataag tttcactcat gcaaattact atatgggagc attattttt tccatcttca    7680 tgattatgtt aaatggcata ccagagatga gcatgcagat tgggagactc ccaagttttt    7740
acaagcaaaa gagctactat ttctattcat catgggcata tgcaatacca gcttcagtcc    7800
taaaggtccc tatttccata ctggattcgc ttgtatggat atctatcaca tattatggta    7860
ttggttatac acctactgtt tcaaggtaaa tatggaaatt tctcaacctt acaatgataa    7920
gaacaaacat tgagaaactc ttaacatatt ttatttatat tcatttctag gttcttctgc    7980
cagtttctga tactttgtct ctccatcat tcagtcacct cgcagtatcg atttattgct    8040
tcatacttcc aaacacctat tgtgtctttc ttctaccttt ttcttgctct aacagtattc    8100
cttacattcg gaggcttcat tcttcccaag agtaagataa ccattgctca ttgaatgcat    8160
ataacttata agcctagcaa atctgaacaa atttgttact ttattgtccc agcctccatg    8220
ccaggatggt taaactgggg attttggata tctccaatga catatgcaga aatcagcata    8280
```

```
gttattaacg aattcttggc accaagatgg cagaaggtga aatgattttt ttttcaaata   8340
aaatattgag tgataagctg atgtcaagca tctaacatca ttgctgcttg tattattttc   8400
aggaaagtat tcaaaacata acaattggga accaaatcct ggttaatcat ggcctatatt   8460
acagttggca ttattattgg atatcctttg gagccttgct tggatctatt ctcttatttt   8520
atatcgcttt tggattggca ctagattaca gaacacgtaa gtttgctact aatgaacaaa   8580
gtgcatatat attgggcttg ggctccatgg tgcccaggca acatgatttg aaatacagca   8640
aatttgggta atgcatttag gaaattccta ttttggatga tataactggt tgtcattgct   8700
gggtataatt tcgaaatacc tactcgatcc caaatatttt tggtaaactc atccatatag   8760
cagttttata tacatacagg tacctagaat tcaagcaata acaaaacaaa gtacagactg   8820
aaaagatcaa acttgtttgg aataaattag acttcacaaa ttttcatgca atatatctag   8880
atggatctgg atataggaat atagtgctga ggcactatgg agcaccagtt aattagactt   8940
tatacacgaa tgttacttac tttagaatcc tactataatt ttgccaattt cagctacaga   9000
agaatatcat ggaagcaggc ctacaaagag cttatgtcaa cagcaggaaa aagattacac   9060
tattcaaaat gaatctgatg atcaatcaaa tatttccaaa ggtaaagaca taaacatctc   9120
aatacgaatt aatagtaaaa aatatgaagg tcccataaaa gtgcatgctt cttcaatgca   9180
ttcatcttat tgcagcaaag gtgactatac cagttatgca tcttccaatt acattccaca   9240
atctgaacta ctacattgat accccaccgg taattaagca agcccccctat gcatttgttt   9300 tgtagttttt tatatttctt gcctggttcg tatttgatga tgaaggtatg taagaaatgt   9360
actctcttgt aggaaatgct gaaacaaggc tatccaacaa gaagacttcg actgcttaat   9420
aacataactg gtgctttacg tcccggtgtt cttctgcac taatgggtgt tagtggagct   9480
gggaagacaa ctctactaga tgtattagca ggaaggaaaa caggaggtta tattgaaggg   9540
gacataagaa taggtggata tcccaaggtg caggaaacat ttgtcagaat cttgggttac   9600
tgcgaacaag tcgacataca ttccccacag cttacagttg aagagtctgt aacttattct   9660
gcgtggcttc gtctgccttc tcatgtcgac gaacaaacaa gatctgtatg tcatcagtct   9720
cagagatata tcgaatttaa taagcatagc actagatgga taaataagag gcttacctaa   9780
gaaactaaca atattcttct tgttcctctc gtagaaattt gttgctgaag tccttgaaac   9840
tgttgaacta gatcaaataa aagatgtctt agtggggtca ccacagaaaa atggattgtc   9900
catggagcag agaaagaggc taacgattgc agtcgagctt gtttcaaacc catcaatcat   9960
actaatggat gaaccaacaa caggtttaga tacaaggtca gcagccattg ttattcgtgc  10020
agtcaaaaat atttgtgaaa caggaaggac agtagtctgt acaatccatc agccgagcac  10080
tgaaattttt gaggcatttg atgaggtaat ttaactttct aaatatatta gtatattaaa  10140
cacaatcaac acaaatacat tttattata tatcaagc acgatcaaca caattttttt  10200
tctggaaaaa tcaatatgtt tagtttcaaa actattagga ttaattaaag cccttgcctt  10260
caacagagca gggctaatct taatatgcac tacctctgta actaactccc accgtcccat  10320
aacactcgcg tccaaaaacg tcttatatta agttacagag gtacctccgt cccataatgt  10380
aagacgtttt ttgacactag tgttatggga cggagggagt agtacattat tagttattta  10440
aaatttaaaa catgtccttt gtgtttgcct ttctagtaaa taataatgat aggaaataat  10500
agtatggaaa tttgcaatat aagcgtgtca accatttcac tttgcgcaac ctagacctca  10560
aattgcactt ttgtcccctc aaatgatcaa ttatgtgcaa caaaacccctt caacttaaac  10620 tttgcttatc tgaaaccttc tattatttgg tttgttagat caagcatttt ctactgaaga  10680
```

```
tacctgatca gaccccttttg aataatatat ctatgaataa acattgatttt gagctaagta    10740 ggattggcat ctaaattata gtaagacgct taacaactat ttactactcc ctgtctcaaa    10800
atgtaagaca tttttttgacc ctttgaataa tatatctatg atataaacat tggtttgagc    10860
taagtaggat tggtatctaa attatagtaa gatgcttaac aactatttac tactccctct    10920
gtctcaaaat gtaagacatt ttttgacaca tgtaagacgt tttttgacat tatcagtgtc    10980
aaaaaatgtc ttacattttg agatagaggg agcatctagc atccttttttc tgtttcggga    11040 gaacatttct taccttaaat atttggcata tactttttgt acaaaaacaa ccccattata    11100
tcagtccgca tgaagaataa agtataaaca tgcaatgaca tgttttgatc tcttaattat    11160
ttgaacatct atgtgttcga tgtcagttaa ttttttatctc ttatttgaac taagtgtcca    11220
cactgacaca aatttgtcat cgcacaaaat ttggactttc tgggcttgat tacaaaatta    11280 aaacaattttt gagggcttat actggaaagt caccgaatag aatatttttt ggttttctga    11340
actatatgtt tatcacaaat cgacgtgact acggacagtt tatatttgct acttctctgt    11400
ttataataac aaaaagggta tagatttttct ttattacagg gctagttgta gtcgaaagtt    11460
gcctataatg catgtagtaa attttgttgc agctcatatt aatgaaaagc ggtgggaaaa    11520
caatctacag tggaccaata ggagagcgct cctgcaaagt gatcgagtac tttgaggcaa    11580
gtttcttgaa catattttcca caaatgtatt tgcctttttc ttgattattc gttttcactg    11640
tttttttctg gaattggaac aataaacgtg agagttccaa aggaacgaac cccaaaacca    11700
gtgctcaaat gttcaacatg ccatagcaaa aacacttaag tcaactctag cagtcatttg    11760
tgttcaatat gtaacttggc taacaattca catgaaatat ataggttaat caaaattttg    11820
atgtgatcat atgtattttta catgttgaac ttaaaagcaa atgtgacaat aaacgtacag    11880
attggcaatg gaaactaaaa acatactgaa gaactttgtt tgcatatcta tgtatgtgtt    11940
tcggtgtttt cagagaggaa gcacggttgt ggcatggcac tgccatattt gtgacatgtg    12000
tcctttggtt ctaatagatt gaattttttct tgtccacttg atagaaaatt tctggagtcc    12060
caaaaataaa gagtaactgc aatccagcta cttggatgat ggatgtaaca tcgacatcaa    12120
tggaggttca acacaatatg gactttgcaa ttttgtatga agagtcgtca ctgcataggt    12180
acatatcttg tggatttagt taggatatcg agcaaaaggc aacatatatg aatagcttaa    12240
gcaaataaaa attcatctag caaaaaaatt tagccaaaca aaataccctcc atttgaagttt    12300 tggaagaatt aaagttactt ttctgcagag aagctgaaga tctagtggag cagctaagta    12360
tcccattacc aaaattcagaa aatctatgtt tctccccatag ttttgcacag aatggctgga    12420
ttcaacttaa agcttgcttg tggaaacaaa acataactta ctggagaagt cctcagtata    12480
acttgaggcg cattatgatg actgtcatat ctgccctgat ctacggaata ttgttctgga    12540
agcatgcaaa agtattgtaa gttcactcct ttgttatcca caacattgca catcagttga    12600
cttcacagac tcattgcaaa attattctaa ctttctcttta tctcttctaa gaaacaacga    12660
gcaggacatg ctcagtgttt tggtgcaat gtatttgggt ttcaccacca taggcgctta    12720
taatgatcag acaatcatac cattcagtac aactgagcgt attgtaatgt atcgtgagag    12780
atttgcagga atgtattcat cttggtcata ttcattcgca caggtcagat aatgatcaca    12840
agcttgtaag agaagtaaaa tatacattga cactgatgct catatttatt caccttctac    12900
aggctttcat tgagataccc tatgtatttta tccaagtggt actgtatacg ttaattgtct    12960
atccgtcaac tggttattat tggacagcac acaaattcct atggttcttc tacaccacat    13020
```

```
tttgttcaat tctctcctat gtttatgttg ggttgcttct tgtttccata acccccaatg    13080
ttcaagtagc taccatactg gcttcatttt tcaacaccat gcaaacacta ttctcaggat    13140
ttattttacc tgcacctgta agtctttatc tcctcccaat atcgtaaact ttagctctcc    13200
aagatgtaac tggcacttct ttttgttagc aaaaatatgg ctgcccacct tgaatatata    13260
ccaactaaga aaataacaac ctacatgaga aattgtaatt gacgagattt tgtagtgtaa    13320
ttatgtaata atattatgga actaataaag gtctaatagg gcattatggg ctttacttta    13380
ttccagagtt catgttcgtg cagaagtctc ctattgtact acatctaggt taccettata    13440 ggcatcctat taatgcattc tgccttacaa aggtatcaaa ttaggtttta gggttttat    13500 cctggtaaac ttttctttat ctttttttgt caatattcac ctttgcaact tccccaccat    13560
gacacctttt tttccttctg ccccagatcc tcaattttac tgattgctta attttgtga    13620 tcgatcaact gatctatcct cctgatagat cttagttttg ggaatattta agtagtaata    13680
tgtcaacaat acaaggacca accgcaacta taaggcatca ctggatgacg atacacagaa    13740
ccactccaat gttagtttaa catcataata gttatagaca taccatcttc agtttcatca    13800
ttaatacttc catttctatt ttctaggttg gaaattgata attattccag cgttgctcaa    13860
tagaataatc atgttctgtt caattgttag ggaagaatca tgaatagagg aaagcactaa    13920
tatgcatttt caattcacgt tgcagcaaat cccgaagtgg tggacttggc tctactatct    13980
cactcctaca tcttgggcac tcaatgccct cttgacatca caatacggaa acatagaaaa    14040
agaggtgaaa gcatttggag aaactaaatc agtttcaatc ttcttgaatg actattttgg    14100
gtttcatcaa gataagttga gcgtagtagc agctgtcctc gttgccttc cttttgtgtt    14160 gataatcttg ttttcgttgt ccattgagaa acttaatttc cagaagaggt aagcaagttc    14220
tgacattcca acagacatga atctgtacat gttacagata tagctacttg cctttttcc    14280 aactgcgaaa tgcagaatca gagctgattg ggtggctatt tttctcaaat ctgatgggta    14340
aacctcatga ataagtaatt gtgtacaata acttgattgt gctaagtacg attgtgagtt    14400
gtaatctttt tgtttcaccg ttcagaagaa tttgatggtt acaaatcatg taacctgctt    14460
tgaagaggat tttgcaattg tgttatgcct tagattactg aatgcatcaa gaggaaaatg    14520
agcacctaac tgaatgaacc tacgatttaa agcgagctta agcacagata acaaaaagct    14580
aacttggatt cccgcaccgt catcatcatg ccttaatatc cgtgcaaggt gtgtgagtgg    14640
tgggtggttt ctgaagagaa acgtggccac acgtcacggc atgcggggcg ccgtttggat    14700
ttcctttgag ctatataaaa cgggaacggc agcatggaat ggtacacttc tctcactttc    14760
acccatcttc atcttgctca tgtgctcact ccgccgttgc aaacaaagct tctcgcatca    14820
agcttttctc cccttcctct attagacaag ttgaagccag acacacccga tgagcgcaga    14880
ggtgcaagcc gaaggagagg atgcagcgca accactaggg gtgctaccag caagaagggt    14940
gccactagca agggtgccgc caacgacaca aagggaaat gggtcacttc gtcggcgaca    15000
caacatcgtc gacacaagat caactgacaa agctcgccaa ctgttgcttc ttccccaata    15060
ttgttcttcc cgaagcaaat ggaagttcac tggcgcgcac cgccgcggga gcagatcgtg    15120
```

<210> SEQ ID NO 7
<211> LENGTH: 841
<212> TYPE: DNA
<213> ORGANISM: Triticum aestivum

<400> SEQUENCE: 7

```
ggaatatgtt tgtttatgtc ttcaaaacag gccagcttgc cattattgca ctcgtaacaa        60
```

```
tgtctgtatt ccttcgaact cgcatgacaa taagtttcac tcatgcaaat tactatatgg    120
gagcattatt tttttccatc ttcatgatta tgttaaatgg cataccagag atgagcatgc    180
agattgggag actcccaagt ttttacaagc aaaagagcta ctatttctat tcatcatggg    240
catatgcaat accagcttca gtcctaaagg tccctatttc catactggat tcgcttgtat    300
ggatatctat cacatattat ggtattggtt atacacctac tgtttcaagg ttcttctgcc    360
agtttctgat actttgtctt ctccatcatt cagtcacctc gcagtatcga tttattgctt    420
catacttcca aacacctatt gtgtctttct tctacctttt tcttgctcta acagtattcc    480
ttacattcgg aggcttcatt cttcccaaga cctccatgcc aggatggtta aactggggat    540
tttggatatc tccaatgaca tatgcagaaa tcagcatagt tattaacgaa ttcttggcac    600
caagatggca gaaggaaagt attcaaaaca taacaattgg gaaccaaatc ctggttaatc    660
atggcctata ttacagttgg cattattatt ggatatcctt tggagccttg cttggatcta    720
ttctcttatt ttatatcgct tttggattgg cactagatta cagaacacct acagaagaat    780
atcatggaag caggcctaca aagagcttat gtcaacagca ggaaaaagat tacactattc    840
a                                                                    841

<210> SEQ ID NO 8
<211> LENGTH: 821
<212> TYPE: DNA
<213> ORGANISM: Triticum aestivum

<400> SEQUENCE: 8
acgctatgac cttaggccta tttaggtgac actccagaac aagtttgtac aaaaaagcag     60
gctcgtaccg gtccggaatt cccgggatat cgtcgaccca cgcgtccgga gaacaatcta    120
ccgcggacca ataagagagc gctcctgcaa agtgatccag tactttgaga gaattgcggg    180
agtcccaaaa ataaagagta actgcaatcc acctacttgg atgatggatg taacatccac    240
atcaatggag gttcaacaca atatggactt tgcaattttg tatgaagagt cgtcactgca    300
tatagaagct gaagatctag tggagcagct aagtatccca ttaccaaatt cagaaaatct    360
atgtttctcc cataatgtta cacagaatgg ctggattcaa cttaaagctt gcttgtggaa    420
acaagacata acttactgga ggagtcctca gtataacttg aggcgcatta tgatgactgt    480
catatctgcc ctgatctacg gaatattggt ctggaagcat gcaaagtat taaacaacga    540 gcacgacatg ctcagtgttt ttggcgcaat gtatttggga ttcaccacca taggcgctta    600
taatgatcag acaatcatac cattcagtac aactgatcgt attgtaatgt atcgtgagag    660
atttgcagga atgtattcat cttggtcata ttcattcgca caggctttgg ttgacatacc    720
ctatgtattt atccaagtgg tactgtatac gttaattgtc tatcggtcaa ctggttatta    780
ttggacagca cccaaattcc tatggttctt ctacaccaca t                        821

<210> SEQ ID NO 9
<211> LENGTH: 865
<212> TYPE: DNA
<213> ORGANISM: Triticum aestivum

<400> SEQUENCE: 9
attcttctga acggtgaaac aaaaagatta caactcacaa tcgtacttag cacaatcaag     60
ttattgtaca caattactta ttcatgaggt ttacccatca gatttgagaa aaatagccac    120
ccaatcagct ctgattctgc atttcgcagt tggaaaaaag gcaagtagct atatctgtaa    180
```

```
catgtacaga ttcatgtctg ttggaatgtc agaacttgct tacctcttct ggaaattaag    240
tttctcaatg gacaacgaaa acaagattat caacacaaaa ggaaaggcaa cgaggacagc    300
tgctactacg ctcaacttat cttgatgaaa cccaaaatag tcattcaaga agattgaaac    360
tgatttagtt tctccaaatg cttttcacctc tttttctatg tttccgtatt gtgatgtcaa    420
gagggcattg agtgcccaag atgtaggagt gagatagtag agccaagtcc accacttcgg    480
gatttgaggt gcaggtaaaa taaatcctga gaatagtgtt tgcatggtgt tgaaaaatga    540
agccagtatg gtagctactt gaacattggg ggttatggaa acaagaagca acccaacata    600
aacataggag agaattgaac aaaatgtggt gtagaagaac cataggaatt tgtgtgctgt    660
ccaataataa ccagttgacg gatagacaat taacgtatac agtaccactt ggataaatac    720
atagggtatc tcaatgaaag cctgtgcgaa tgaatatgac caagatgaat acattcctgc    780
aaatctctca cgatacatta caatacgctc agttgtactg aatggtatga ttgtctgatc    840
attataagcg cctatggggg tgaaa                                          865
```

<210> SEQ ID NO 10
<211> LENGTH: 810
<212> TYPE: DNA
<213> ORGANISM: Triticum aestivum

<400> SEQUENCE: 10

```
gacattaggc ctatttaggt gatctataga acaagtttgt acaaaaaagc aggctggtac     60
cggtccggaa ttcccgggat atcgtcgacc cacgcgtccg gttaattgtc tatccgtcaa    120
ctggttatta ttggacagca cacaaattcc tatggttctt ctacaccaca ttttgttcaa    180
ttctctccta tgtttatgtt gggttgcttc ttgtttccat aaccccccaat gttcaagtag    240 ctaccatact ggcttcattt ttcaacacca tgcaaacact attctcagga tttatttttac    300 ctgcacctca atcccgaag tggtggactt ggctctacta tctcactcct acatcttggg    360
cactcaatgc cctcttgaca tcacaatacg gaaacataga aaaagaggtg aaagcatttg    420
gagaaactaa atcagtttca atcttcttga tgactatttt gggtttcat caagataagt    480 tgagcgtagc agcagctgtc ctcgttgcct ttccttttgt gttgataatc ttgttttcgt    540
tgtccattga gaaacttaat ttccagaaga ggtaagcaag ttctgacatt ccaacagaca    600
tgaatctgta catgttacag atatagctac ttgccttttt tcaactgcga aatgcagaat    660
cagagctgat tgggtggcta ttttctcaa atctgatggg taaacctcat gaataagtaa    720
ttgtgtacaa taacttgatt gtgctaagta cgattgtgag ttgtaatctt tttgtttcac    780
cgttcagaag aatttgatgg ttacaaatca                                     810
```

<210> SEQ ID NO 11
<211> LENGTH: 571
<212> TYPE: DNA
<213> ORGANISM: Hordeum vulgare

<400> SEQUENCE: 11

```
cccctgcgga aatgagggag cacggttaca tggaaaagaa actcagctac tcccaatatc     60
acgggagcat tccagccagg ggttctctcg gcactcatgg gggttactgg agcgaaaaaa    120
caacactcct tgatgttctt gctggaagga aaactggcgg tgttattgaa ggggatataa    180
gaataggagg gtatcctaaa attcagcaga cttttgctag gatatcaggc tactgtgaac    240 aaaactgatgt ccattcccca caaatcacag tgggtgaatc ggttgcatat tcagcctggt    300
tacgccttcc accagaagtt gatgcaaaaa taagaaccga atttgtcaac gaagttcttg    360
```

```
aaacaattga gttggacgaa attagagatt ctttggtcgg aatacctggg gtaaatgggc    420
tatcaacaga gcaaaggaaa cggctcacga ttgcagtcga gctcgtgtct aacccctcaa    480
tcatatttat ggacgagcca acgtcaggct tggatgcaag ggccgctgct attgtcatgc    540
gtgcagtgaa gaatgttgca gacacaggcc g                                   571
```

<210> SEQ ID NO 12
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 12

```
catcaagatt tcaccgcctg tgc                                             23
```

<210> SEQ ID NO 13
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 13

```
gaagcctagc aacttcacga ggc                                             23
```

<210> SEQ ID NO 14
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 14

```
gcggggccca caatcatctc ggc                                             23
```

<210> SEQ ID NO 15
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 15

```
catctttcgt atacatgaga aac                                             23
```

<210> SEQ ID NO 16
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 16

```
gtgtcgattc atgtgagatg c                                               21
```

<210> SEQ ID NO 17
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 17
cattatgtta gcagcttagc g                                              21

<210> SEQ ID NO 18
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 18
ccaaccatca ttttggagca tg                                             22

<210> SEQ ID NO 19
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 19
gtagatcgtg tcgtgttcaa c                                              21

<210> SEQ ID NO 20
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 20
ctgctaatcc taagtaacgc tc                                             22

<210> SEQ ID NO 21
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 21
cgtgagcaag acatgggcg                                                 19

<210> SEQ ID NO 22
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 22
gctacagctc tgaaactaca c                                              21

<210> SEQ ID NO 23
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 23
gatttgcacg ttgatgaaac cag                                            23

<210> SEQ ID NO 24
<211> LENGTH: 24
<212> TYPE: DNA
<213> ORGANISM: Artificial Sequence

```
<220> FEATURE:
<223> OTHER INFORMATION: Oligonucleotide primer

<400> SEQUENCE: 24
cagaatgaag tttaacctgg cctg                                      24

<210> SEQ ID NO 25
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 25
ggctggctac tacgacgacg                                           20

<210> SEQ ID NO 26
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 26
atggtctttt tccttcagc c                                          21

<210> SEQ ID NO 27
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 27
gcctactttg acggcatatg g                                         21

<210> SEQ ID NO 28
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 28
ccatcttgac atactttggc cttcc                                     25

<210> SEQ ID NO 29
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 29
ctccctcccg tgagtatatt c                                         21

<210> SEQ ID NO 30
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 30
atcaaaatcc cattgcctga c                                         21
```

<210> SEQ ID NO 31
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 31
gttggttaag actggtgatg g                                              21

<210> SEQ ID NO 32
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 32
tgcttgctat tgctgaatag t                                              21

<210> SEQ ID NO 33
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 33
catctttcgt atacatgaga aac                                            23

<210> SEQ ID NO 34
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 34
gtgtcgattc atgtgagatg c                                              21

<210> SEQ ID NO 35
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 35
cattatgtta gcagcttagc g                                              21

<210> SEQ ID NO 36
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 36
ccaaccatca ttttggagca tg                                             22

<210> SEQ ID NO 37
<211> LENGTH: 21
<212> TYPE: DNA
<213> ORGANISM: Artificial Sequence
<220> FEATURE:
<223> OTHER INFORMATION: Oligonucleotide primer

```
<400> SEQUENCE: 37
gtagatcgtg tcgtgttcaa c                                              21

<210> SEQ ID NO 38
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 38
ctgctaatcc taagtaacgc tc                                             22

<210> SEQ ID NO 39
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 39
cgtgagcaag acatgggcg                                                 19

<210> SEQ ID NO 40
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 40
gctacagctc tgaaactaca c                                              21

<210> SEQ ID NO 41
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 41
gatttgcacg ttgatgaaac cag                                            23

<210> SEQ ID NO 42
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 42
cagaatgaag tttaacctgg cctg                                           24

<210> SEQ ID NO 43
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 43
ggctggctac tacgacgacg                                                20

<210> SEQ ID NO 44
```

<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 44
atggtctttt tccttcagc c                                              21

<210> SEQ ID NO 45
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 45
gcctactttg acggcatatg g                                             21

<210> SEQ ID NO 46
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 46
ccatcttgac atactttggc cttcc                                         25

<210> SEQ ID NO 47
<211> LENGTH: 1406
<212> TYPE: PRT
<213> ORGANISM: Oryza sativa

<400> SEQUENCE: 47

Met Ser Ser Ser Ser His His Pro Glu Phe Ala Ser Cys Thr Ala
1               5                   10                  15

Asn Asp Asp Glu His His Leu Asp Glu Phe Glu Leu Glu Leu Val Val
                20                  25                  30

Gln Asp Val Gln Arg Gln Gln Asn Asn Gly Ser Ala Asn Thr Asp Gln
        35                  40                  45

His Glu Arg Glu Asn Leu Leu Leu Asp Asp Ser Ser Lys Ser Gly
    50                  55                  60

Ala Leu Lys Glu Arg Leu Phe Phe Asp Asn Leu Leu Lys Asn Val Gln
65                  70                  75                  80

Asp Asp His Ile Arg Phe Leu His Arg Gln Lys Glu Arg Ile Asp Arg
                85                  90                  95

Val Asp Val Lys Leu Pro Ala Ile Glu Val Arg Tyr Asn Asn Leu Ser
            100                 105                 110

Val Glu Ala Glu Cys Arg Thr Ala Asn Gly Asp His Leu Pro Ser Leu
        115                 120                 125

Trp Asn Ser Thr Lys Gly Ala Phe Ser Gly Leu Val Lys Leu Leu Gly
    130                 135                 140

Leu Glu Thr Glu Arg Ala Lys Ile Asn Val Leu Glu Asp Val Ser Gly
145                 150                 155                 160

Ile Ile Lys Pro Cys Arg Leu Thr Leu Leu Gly Pro Pro Gly Cys
                165                 170                 175

Gly Lys Ser Thr Leu Leu Arg Ala Leu Ser Gly Lys Leu Asp Lys Ser
            180                 185                 190

Leu Lys Val Thr Gly Asp Ile Ser Tyr Asn Gly Tyr Gln Leu Asp Glu

```
                195                 200                 205
Phe Val Pro Glu Lys Thr Ala Ala Tyr Ile Ser Gln Tyr Asp Leu His
210                 215                 220
Ile Pro Glu Met Thr Val Arg Glu Thr Leu Asp Phe Ser Ser Arg Cys
225                 230                 235                 240
Gln Gly Val Gly Arg Pro Lys Ile Leu Lys Glu Val Ser Ala Arg
                    245                 250                 255
Glu Ser Ala Ala Gly Ile Ile Pro Asp Ala Asp Ile Asp Ile Tyr Met
            260                 265                 270
Lys Ala Ile Ser Val Glu Ala Ser Lys Arg Ser Leu Gln Thr Asp Tyr
                275                 280                 285
Ile Leu Lys Ile Met Gly Leu Glu Ile Cys Ala Asp Thr Met Val Gly
290                 295                 300
Asp Ala Met Ile Arg Gly Leu Ser Gly Gly Gln Lys Lys Arg Leu Thr
305                 310                 315                 320
Thr Ala Glu Met Ile Val Gly Pro Ala Arg Ala Tyr Phe Met Asp Glu
                325                 330                 335
Ile Ser Asn Gly Leu Asp Ser Ser Thr Thr Phe Gln Ile Ile Ser Cys
            340                 345                 350
Phe Gln Gln Leu Thr Asn Ile Ser Glu Tyr Thr Met Val Ile Ser Leu
                355                 360                 365
Leu Gln Pro Thr Pro Glu Val Phe Asp Leu Phe Asp Asp Leu Ile Leu
370                 375                 380
Met Ala Glu Gly Lys Ile Ile Tyr His Gly Pro Arg Asn Glu Ala Leu
385                 390                 395                 400
Asn Phe Phe Glu Glu Cys Gly Phe Ile Cys Pro Glu Arg Lys Glu Val
                405                 410                 415
Ala Asp Phe Leu Gln Glu Ile Leu Ser Cys Lys Asp Gln Gln Gln Tyr
                420                 425                 430
Trp Ser Gly Pro Asn Glu Ser Tyr Arg Tyr Ile Ser Pro His Glu Leu
            435                 440                 445
Ser Ser Met Phe Lys Glu Asn His Arg Gly Arg Lys Leu Glu Glu Pro
450                 455                 460
Ile Val Ser Pro Lys Ser Glu Leu Gly Lys Glu Ala Leu Ala Phe Asn
465                 470                 475                 480
Lys Tyr Ser Leu Gln Lys Leu Glu Met Phe Lys Ala Cys Gly Ala Arg
                485                 490                 495
Glu Ala Leu Leu Met Lys Arg Ser Met Phe Val Tyr Val Phe Lys Thr
                500                 505                 510
Gly Gln Leu Ala Ile Ile Ala Leu Val Thr Met Ser Val Phe Leu Arg
            515                 520                 525
Thr Arg Met Thr Thr Asp Phe Thr His Ala Thr Tyr Tyr Met Gly Ala
530                 535                 540
Leu Phe Phe Ser Ile Leu Met Ile Met Leu Asn Gly Thr Pro Glu Ile
545                 550                 555                 560
Ser Met Gln Ile Arg Arg Leu Pro Ser Phe Tyr Lys Gln Lys Ser Tyr
                565                 570                 575
Tyr Phe Tyr Ser Ser Trp Ala Tyr Ala Ile Pro Ala Ser Val Leu Lys
            580                 585                 590
Val Pro Val Ser Ile Leu Asp Ser Leu Val Trp Ile Cys Ile Thr Tyr
                595                 600                 605
Tyr Gly Ile Gly Tyr Thr Ala Ser Val Ser Arg Phe Phe Cys Gln Phe
            610                 615                 620
```

-continued

Leu Met Leu Cys Phe Val His Gln Ser Val Thr Ser Leu Tyr Arg Phe
625                 630                 635                 640

Ile Ala Ser Tyr Phe Gln Thr Pro Thr Ala Ser Phe Phe Tyr Leu Phe
                645                 650                 655

Leu Ala Leu Thr Phe Phe Leu Met Phe Gly Gly Phe Thr Leu Pro Lys
            660                 665                 670

Pro Ser Met Pro Gly Trp Leu Asn Trp Gly Phe Trp Ile Ser Pro Met
        675                 680                 685

Thr Tyr Ala Glu Ile Gly Thr Val Ile Asn Glu Phe Gln Ala Pro Arg
    690                 695                 700

Trp Gln Lys Glu Thr Ile Gln Asn Ile Thr Ile Gly Asn Arg Ile Leu
705                 710                 715                 720

Ile Asn His Gly Leu Tyr Tyr Ser Trp His Phe Tyr Trp Ile Ser Ile
                725                 730                 735

Gly Ala Leu Phe Gly Ser Ile Ile Leu Phe Tyr Ile Ala Phe Gly Leu
            740                 745                 750

Ala Leu Asp Tyr Ile Thr Ser Ile Glu Glu Tyr His Gly Ser Arg Pro
        755                 760                 765

Ile Lys Arg Leu Cys Gln Glu Gln Lys Asp Ser Asn Ile Arg Lys
    770                 775                 780

Glu Ser Asp Gly His Ser Asn Ile Ser Arg Ala Lys Met Thr Ile Pro
785                 790                 795                 800

Val Met Glu Leu Pro Ile Thr Phe His Asn Leu Asn Tyr Tyr Ile Asp
                805                 810                 815

Thr Pro Pro Glu Met Leu Lys Gln Gly Tyr Pro Thr Lys Arg Leu Gln
            820                 825                 830

Leu Leu Asn Asn Ile Thr Gly Ala Leu Arg Pro Gly Val Leu Ser Ala
        835                 840                 845

Leu Met Gly Val Ser Gly Ala Gly Lys Thr Thr Leu Leu Asp Val Leu
    850                 855                 860

Ala Gly Arg Lys Thr Gly Gly Tyr Ile Glu Gly Asp Ile Arg Ile Gly
865                 870                 875                 880

Gly Tyr Pro Lys Val Gln Glu Thr Phe Val Arg Ile Leu Gly Tyr Cys
                885                 890                 895

Glu Gln Ala Asp Ile His Ser Pro Gln Leu Thr Val Glu Glu Ser Val
            900                 905                 910

Thr Tyr Ser Ala Trp Leu Arg Leu Pro Ser His Val Asp Lys Lys Thr
        915                 920                 925

Arg Ser Glu Phe Val Ala Glu Val Leu Glu Thr Val Glu Leu Asp Gln
    930                 935                 940

Ile Lys Asp Val Leu Val Gly Thr Pro Gln Lys Asn Gly Leu Ser Met
945                 950                 955                 960

Glu Gln Arg Lys Arg Leu Thr Ile Ala Val Glu Leu Val Ser Asn Pro
                965                 970                 975

Ser Val Ile Leu Met Asp Glu Pro Thr Thr Gly Leu Asp Thr Arg Ser
            980                 985                 990

Ala Ala Ile Val Ile Arg Ala Val Lys Asn Ile Cys Lys Thr Gly Arg
        995                 1000                1005

Thr Val Val Cys Thr Ile His Gln Pro Ser Thr Lys Ile Phe Glu
    1010                1015                1020

Ala Phe Asp Glu Leu Ile Leu Met Lys Asn Gly Gly Lys Ile Ile
    1025                1030                1035

-continued

```
Tyr Asn Gly Pro Ile Gly Glu Arg Ser Ser Lys Val Ile Glu Tyr
1040                1045                1050

Phe Glu Lys Ile Ser Gly Val Leu Lys Val Lys Ser Asn Cys Asn
    1055                1060                1065

Pro Ala Ala Trp Met Met Asp Val Thr Ser Thr Ser Met Glu Val
    1070                1075                1080

Gln His Asn Met Asp Phe Ala Ile Leu Tyr Asp Glu Ser Ser Gln
    1085                1090                1095

His Arg Asp Ile Val Glu Leu Val Glu Lys Leu Ser Ile Pro Ile
    1100                1105                1110

Pro Asn Ser Glu Ile Leu Ser Phe Ser His Arg Phe Pro Arg Asn
    1115                1120                1125

Gly Trp Ile Gln Leu Lys Ala Cys Leu Trp Lys Gln Asn Leu Thr
    1130                1135                1140

Tyr Trp Arg Ser Pro Glu Tyr Asn Leu Arg Arg Ile Met Leu Thr
    1145                1150                1155

Val Ile Ser Ala Leu Val Tyr Gly Val Leu Phe Trp Lys Arg Ala
    1160                1165                1170

Lys Ile Leu Asn Asp Glu Gln Asp Leu Phe Asn Val Phe Gly Ala
    1175                1180                1185

Met Tyr Leu Gly Ser Thr Thr Ile Gly Ser Tyr Asn His Gln Ser
    1190                1195                1200

Ile Ile Pro Phe Ser Thr Thr Glu Arg Ile Val Met Tyr Arg Glu
    1205                1210                1215

Lys Phe Ala Gly Met Tyr Ser Ser Trp Ser Tyr Ser Phe Ala Gln
    1220                1225                1230

Ala Ala Ile Glu Ile Pro Tyr Val Phe Ile Gln Val Val Leu Tyr
    1235                1240                1245

Thr Leu Ile Ile Tyr Pro Ser Ile Gly Tyr Tyr Trp Thr Thr His
    1250                1255                1260

Lys Phe Ile Trp Phe Phe Tyr Thr Thr Phe Cys Ser Ser Leu Ser
    1265                1270                1275

Tyr Ile Tyr Val Gly Leu Leu Leu Val Ser Leu Thr Pro Asn Val
    1280                1285                1290

Gln Val Ala Thr Ile Leu Ala Ser Phe Phe Asn Thr Met Gln Thr
    1295                1300                1305

Leu Phe Ser Gly Phe Ile Leu Pro Ala Pro Gln Ile Pro Lys Trp
    1310                1315                1320

Trp Val Trp Leu Tyr Tyr Leu Thr Pro Thr Ser Trp Thr Leu Asp
    1325                1330                1335

Ala Leu Leu Thr Ser Gln Tyr Gly Asn Ile Glu Lys Glu Val Arg
    1340                1345                1350

Ala Phe Gly Glu Thr Lys Ser Val Ser Ile Phe Leu Asn Asp Tyr
    1355                1360                1365

Phe Gly Phe His Lys Asp Lys Leu Ser Leu Val Ala Ala Val Leu
    1370                1375                1380

Ile Ala Phe Pro Val Leu Ile Ile Leu Phe Ser Phe Ser Ile
    1385                1390                1395

Glu Lys Phe Asn Phe Gln Lys Arg
    1400                1405
```

<210> SEQ ID NO 48
<211> LENGTH: 1413
<212> TYPE: PRT

<213> ORGANISM: Arabidopsis thaliana

<400> SEQUENCE: 48

```
Met Gly Ser Ser Phe Arg Ser Ser Ser Arg Asn Glu His Glu Asp
1               5                   10                  15
Gly Gly Asp Glu Ala Glu His Ala Leu Gln Trp Ala Glu Ile Gln Arg
            20                  25                  30
Leu Pro Thr Phe Lys Arg Leu Arg Ser Ser Leu Val Asp Lys Tyr Gly
                35                  40                  45
Glu Gly Thr Glu Lys Gly Lys Lys Val Val Asp Val Thr Lys Leu Gly
        50                  55                  60
Ala Met Glu Arg His Leu Met Ile Glu Lys Leu Ile Lys His Ile Glu
65                  70                  75                  80
Asn Asp Asn Leu Lys Leu Leu Lys Lys Ile Arg Arg Arg Met Glu Arg
                85                  90                  95
Val Gly Val Glu Phe Pro Ser Ile Glu Val Arg Tyr Glu His Leu Gly
            100                 105                 110
Val Glu Ala Ala Cys Glu Val Glu Gly Lys Ala Leu Pro Thr Leu
        115                 120                 125
Trp Asn Ser Leu Lys His Val Phe Leu Asp Leu Leu Lys Leu Ser Gly
    130                 135                 140
Val Arg Thr Asn Glu Ala Asn Ile Lys Ile Leu Thr Asp Val Ser Gly
145                 150                 155                 160
Ile Ile Ser Pro Gly Arg Leu Thr Leu Leu Leu Gly Pro Pro Gly Cys
                165                 170                 175
Gly Lys Thr Thr Leu Leu Lys Ala Leu Ser Gly Asn Leu Glu Asn Asn
            180                 185                 190
Leu Lys Cys Tyr Gly Glu Ile Ser Tyr Asn Gly His Gly Leu Asn Glu
        195                 200                 205
Val Val Pro Gln Lys Thr Ser Ala Tyr Ile Ser Gln His Asp Leu His
    210                 215                 220
Ile Ala Glu Met Thr Thr Arg Glu Thr Ile Asp Phe Ser Ala Arg Cys
225                 230                 235                 240
Gln Gly Val Gly Ser Arg Thr Asp Ile Met Met Glu Val Ser Lys Arg
                245                 250                 255
Glu Lys Asp Gly Gly Ile Ile Pro Asp Pro Glu Ile Asp Ala Tyr Met
            260                 265                 270
Lys Ala Ile Ser Val Lys Gly Leu Lys Arg Ser Leu Gln Thr Asp Tyr
        275                 280                 285
Ile Leu Lys Ile Leu Gly Leu Asp Ile Cys Ala Glu Thr Leu Val Gly
    290                 295                 300
Asn Ala Met Lys Arg Gly Ile Ser Gly Gly Gln Lys Lys Arg Leu Thr
305                 310                 315                 320
Thr Ala Glu Met Ile Val Gly Pro Thr Lys Ala Leu Phe Met Asp Glu
                325                 330                 335
Ile Thr Asn Gly Leu Asp Ser Ser Thr Ala Phe Gln Ile Ile Lys Ser
            340                 345                 350
Leu Gln Gln Val Ala His Ile Thr Asn Ala Thr Val Phe Val Ser Leu
        355                 360                 365
Leu Gln Pro Ala Pro Glu Ser Tyr Asp Leu Phe Asp Asp Ile Val Leu
    370                 375                 380
Met Ala Glu Gly Lys Ile Val Tyr His Gly Pro Arg Asp Asp Val Leu
385                 390                 395                 400
```

```
Lys Phe Phe Glu Glu Cys Gly Phe Gln Cys Pro Glu Arg Lys Gly Val
                405                 410                 415

Ala Asp Phe Leu Gln Glu Val Ile Ser Lys Lys Asp Gln Gly Gln Tyr
            420                 425                 430

Trp Leu His Gln Asn Leu Pro His Ser Phe Val Ser Val Asp Thr Leu
        435                 440                 445

Ser Lys Arg Phe Lys Asp Leu Glu Ile Gly Arg Lys Ile Glu Glu Ala
450                 455                 460

Leu Ser Lys Pro Tyr Asp Ile Ser Lys Thr His Lys Asp Ala Leu Ser
465                 470                 475                 480

Phe Asn Val Tyr Ser Leu Pro Lys Trp Glu Leu Phe Arg Ala Cys Ile
                485                 490                 495

Ser Arg Glu Phe Leu Leu Met Lys Arg Asn Tyr Phe Val Tyr Leu Phe
            500                 505                 510

Lys Thr Phe Gln Leu Val Leu Ala Ala Ile Ile Thr Met Thr Val Phe
        515                 520                 525

Ile Arg Thr Arg Met Asp Ile Asp Ile Ile His Gly Asn Ser Tyr Met
530                 535                 540

Ser Cys Leu Phe Phe Ala Thr Val Val Leu Leu Val Asp Gly Ile Pro
545                 550                 555                 560

Glu Leu Ser Met Thr Val Gln Arg Leu Ser Val Phe Tyr Lys Gln Lys
                565                 570                 575

Gln Leu Cys Phe Tyr Pro Ala Trp Ala Tyr Ala Ile Pro Ala Thr Val
            580                 585                 590

Leu Lys Ile Pro Leu Ser Phe Phe Glu Ser Leu Val Trp Thr Cys Leu
        595                 600                 605

Thr Tyr Tyr Val Ile Gly Tyr Thr Pro Glu Pro Tyr Arg Phe Phe Arg
610                 615                 620

Gln Phe Met Ile Leu Phe Ala Val His Phe Thr Ser Ile Ser Met Phe
625                 630                 635                 640

Arg Cys Ile Ala Ala Ile Phe Gln Thr Gly Val Ala Ala Met Thr Ala
                645                 650                 655

Gly Ser Phe Val Met Leu Ile Thr Phe Val Phe Ala Gly Phe Ala Ile
            660                 665                 670

Pro Tyr Thr Asp Met Pro Gly Trp Leu Lys Trp Gly Phe Trp Val Asn
        675                 680                 685

Pro Ile Ser Tyr Ala Glu Ile Gly Leu Ser Val Asn Glu Phe Leu Ala
690                 695                 700

Pro Arg Trp Gln Lys Met Gln Pro Thr Asn Val Thr Leu Gly Arg Thr
705                 710                 715                 720

Ile Leu Glu Ser Arg Gly Leu Asn Tyr Asp Asp Tyr Met Tyr Trp Val
                725                 730                 735

Ser Leu Ser Ala Leu Leu Gly Leu Thr Ile Ile Phe Asn Thr Ile Phe
            740                 745                 750

Thr Leu Ala Leu Ser Phe Leu Lys Ser Pro Thr Ser Ser Arg Pro Met
        755                 760                 765

Ile Ser Gln Asp Lys Leu Ser Glu Leu Gln Gly Thr Lys Asp Ser Ser
770                 775                 780

Val Lys Lys Asn Lys Pro Leu Asp Ser Ser Ile Lys Thr Asn Glu Asp
785                 790                 795                 800

Pro Gly Lys Met Ile Leu Pro Phe Lys Pro Leu Thr Ile Thr Phe Gln
                805                 810                 815

Asp Leu Asn Tyr Tyr Val Asp Val Pro Val Glu Met Lys Gly Gln Gly
```

```
                820                 825                 830
Tyr Asn Glu Lys Lys Leu Gln Leu Leu Ser Glu Ile Thr Gly Ala Phe
                835                 840                 845

Arg Pro Gly Val Leu Thr Ala Leu Met Gly Ile Ser Gly Ala Gly Lys
                850                 855                 860

Thr Thr Leu Leu Asp Val Leu Ala Gly Arg Lys Thr Ser Gly Tyr Ile
865                 870                 875                 880

Glu Gly Glu Ile Arg Ile Ser Gly Phe Leu Lys Val Gln Glu Thr Phe
                885                 890                 895

Ala Arg Val Ser Gly Tyr Cys Glu Gln Thr Asp Ile His Ser Pro Ser
                900                 905                 910

Ile Thr Val Glu Glu Ser Leu Ile Tyr Ser Ala Trp Leu Arg Leu Val
                915                 920                 925

Pro Glu Ile Asn Pro Gln Thr Lys Ile Arg Phe Val Lys Gln Val Leu
                930                 935                 940

Glu Thr Ile Glu Leu Glu Glu Ile Lys Asp Ala Leu Val Gly Val Ala
945                 950                 955                 960

Gly Val Ser Gly Leu Ser Thr Glu Gln Arg Lys Arg Leu Thr Val Ala
                965                 970                 975

Val Glu Leu Val Ala Asn Pro Ser Ile Ile Phe Met Asp Glu Pro Thr
                980                 985                 990

Thr Gly Leu Asp Ala Arg Ala Ala Ala Ile Val Met Arg Ala Val Lys
                995                1000                1005

Asn Val Ala Glu Thr Gly Arg Thr Ile Val Cys Thr Ile His Gln
                1010                1015               1020

Pro Ser Ile His Ile Phe Glu Ala Phe Asp Glu Leu Val Leu Leu
                1025                1030               1035

Lys Arg Gly Gly Arg Met Ile Tyr Ser Gly Pro Leu Gly Gln His
                1040                1045               1050

Ser Ser Cys Val Ile Glu Tyr Phe Gln Asn Ile Pro Gly Val Ala
                1055                1060               1065

Lys Ile Arg Asp Lys Tyr Asn Pro Ala Thr Trp Met Leu Glu Val
                1070                1075               1080

Thr Ser Glu Ser Val Glu Thr Glu Leu Asp Met Asp Phe Ala Lys
                1085                1090               1095

Ile Tyr Asn Glu Ser Asp Leu Tyr Lys Asn Asn Ser Glu Leu Val
                1100                1105               1110

Lys Glu Leu Ser Lys Pro Asp His Gly Ser Ser Asp Leu His Phe
                1115                1120               1125

Lys Arg Thr Phe Ala Gln Asn Trp Trp Glu Gln Phe Lys Ser Cys
                1130                1135               1140

Leu Trp Lys Met Ser Leu Ser Tyr Trp Arg Ser Pro Ser Tyr Asn
                1145                1150               1155

Leu Met Arg Ile Gly His Thr Phe Ile Ser Ser Phe Ile Phe Gly
                1160                1165               1170

Leu Leu Phe Trp Asn Gln Gly Lys Lys Ile Asp Thr Gln Gln Asn
                1175                1180               1185

Leu Phe Thr Val Leu Gly Ala Ile Tyr Gly Leu Val Leu Phe Val
                1190                1195               1200

Gly Ile Asn Asn Cys Thr Ser Ala Leu Gln Tyr Phe Glu Thr Glu
                1205                1210               1215

Arg Asn Val Met Tyr Arg Glu Arg Phe Ala Gly Met Tyr Ser Ala
                1220                1225               1230
```

```
Phe Ala Tyr Ala Leu Ala Gln Val Val Thr Glu Ile Pro Tyr Ile
    1235            1240                1245

Phe Ile Gln Ser Ala Glu Phe Val Ile Val Ile Tyr Pro Met Ile
    1250            1255                1260

Gly Phe Tyr Ala Ser Phe Ser Lys Val Phe Trp Ser Leu Tyr Ala
    1265            1270                1275

Met Phe Cys Asn Leu Leu Cys Phe Asn Tyr Leu Ala Met Phe Leu
    1280            1285                1290

Ile Ser Ile Thr Pro Asn Phe Met Val Ala Ala Ile Leu Gln Ser
    1295            1300                1305

Leu Phe Phe Thr Thr Phe Asn Ile Phe Ala Gly Phe Leu Ile Pro
    1310            1315                1320

Lys Pro Gln Ile Pro Lys Trp Trp Val Trp Phe Tyr Tyr Ile Thr
    1325            1330                1335

Pro Thr Ser Trp Thr Leu Asn Leu Phe Phe Ser Ser Gln Tyr Gly
    1340            1345                1350

Asp Ile His Gln Lys Ile Asn Ala Phe Gly Glu Thr Lys Thr Val
    1355            1360                1365

Ala Ser Phe Leu Glu Asp Tyr Phe Gly Phe His His Asp Arg Leu
    1370            1375                1380

Met Ile Thr Ala Ile Ile Leu Ile Ala Phe Pro Ile Ala Leu Ala
    1385            1390                1395

Thr Met Tyr Ala Phe Phe Val Ala Lys Leu Asn Phe Gln Lys Arg
    1400            1405                1410

<210> SEQ ID NO 49
<211> LENGTH: 1450
<212> TYPE: PRT
<213> ORGANISM: Arabidopsis thaliana

<400> SEQUENCE: 49

Met Ala His Met Val Gly Ala Asp Asp Ile Glu Ser Leu Arg Val Glu
1               5                   10                  15

Leu Ala Glu Ile Gly Arg Ser Ile Arg Ser Ser Phe Arg Arg His Thr
                20                  25                  30

Ser Ser Phe Arg Ser Ser Ser Ile Tyr Glu Val Glu Asn Asp Gly
        35                  40                  45

Asp Val Asn Asp His Asp Ala Glu Tyr Ala Leu Gln Trp Ala Glu Ile
    50                  55                  60

Glu Arg Leu Pro Thr Val Lys Arg Met Arg Ser Thr Leu Leu Asp Asp
65                  70                  75                  80

Gly Asp Glu Ser Met Thr Glu Lys Gly Arg Arg Val Val Asp Val Thr
                85                  90                  95

Lys Leu Gly Ala Val Glu Arg His Leu Met Ile Glu Lys Leu Ile Lys
            100                 105                 110

His Ile Glu Asn Asp Asn Leu Lys Leu Leu Lys Lys Ile Arg Arg Arg
        115                 120                 125

Ile Asp Arg Val Gly Met Glu Leu Pro Thr Ile Glu Val Arg Tyr Glu
    130                 135                 140

Ser Leu Lys Val Val Ala Glu Cys Glu Val Val Glu Gly Lys Ala Leu
145                 150                 155                 160

Pro Thr Leu Trp Asn Thr Ala Lys Arg Val Leu Ser Glu Leu Val Lys
                165                 170                 175

Leu Thr Gly Ala Lys Thr His Glu Ala Lys Ile Asn Ile Ile Asn Asp
```

-continued

```
                180                 185                 190
Val Asn Gly Ile Ile Lys Pro Gly Arg Leu Thr Leu Leu Gly Pro
            195                 200                 205
Pro Ser Cys Gly Lys Thr Thr Leu Leu Lys Ala Leu Ser Gly Asn Leu
210                 215                 220
Glu Asn Asn Leu Lys Cys Ser Gly Glu Ile Ser Tyr Asn Gly His Arg
225                 230                 235                 240
Leu Asp Glu Phe Val Pro Gln Lys Thr Ser Ala Tyr Ile Ser Gln Tyr
                245                 250                 255
Asp Leu His Ile Ala Glu Met Thr Val Arg Glu Thr Val Asp Phe Ser
            260                 265                 270
Ala Arg Cys Gln Gly Val Gly Ser Arg Thr Asp Ile Met Met Glu Val
        275                 280                 285
Ser Lys Arg Glu Lys Glu Lys Gly Ile Ile Pro Asp Thr Glu Val Asp
    290                 295                 300
Ala Tyr Met Lys Ala Ile Ser Val Glu Gly Leu Gln Arg Ser Leu Gln
305                 310                 315                 320
Thr Asp Tyr Ile Leu Lys Ile Leu Gly Leu Asp Ile Cys Ala Glu Ile
                325                 330                 335
Leu Ile Gly Asp Val Met Arg Arg Gly Ile Ser Gly Gly Gln Lys Lys
            340                 345                 350
Arg Leu Thr Thr Ala Glu Met Ile Val Gly Pro Thr Lys Ala Leu Phe
        355                 360                 365
Met Asp Glu Ile Thr Asn Gly Leu Asp Ser Ser Thr Ala Phe Gln Ile
    370                 375                 380
Val Lys Ser Leu Gln Gln Phe Ala His Ile Ser Ser Ala Thr Val Leu
385                 390                 395                 400
Val Ser Leu Leu Gln Pro Ala Pro Glu Ser Tyr Asp Leu Phe Asp Asp
                405                 410                 415
Ile Met Leu Met Ala Lys Gly Arg Ile Val Tyr His Gly Pro Arg Gly
            420                 425                 430
Glu Val Leu Asn Phe Phe Glu Asp Cys Gly Phe Arg Cys Pro Glu Arg
        435                 440                 445
Lys Gly Val Ala Asp Phe Leu Gln Glu Val Ile Ser Lys Lys Asp Gln
    450                 455                 460
Ala Gln Tyr Trp Trp His Glu Asp Leu Pro Tyr Ser Phe Val Ser Val
465                 470                 475                 480
Glu Met Leu Ser Lys Lys Phe Lys Asp Leu Ser Ile Gly Lys Lys Ile
                485                 490                 495
Glu Asp Thr Leu Ser Lys Pro Tyr Asp Arg Ser Lys Ser His Lys Asp
            500                 505                 510
Ala Leu Ser Phe Ser Val Tyr Ser Leu Pro Asn Trp Glu Leu Phe Ile
        515                 520                 525
Ala Cys Ile Ser Arg Glu Tyr Leu Leu Met Lys Arg Asn Tyr Phe Val
    530                 535                 540
Tyr Ile Phe Lys Thr Ala Gln Leu Val Met Ala Ala Phe Ile Thr Met
545                 550                 555                 560
Thr Val Phe Ile Arg Thr Arg Met Gly Ile Asp Ile Ile His Gly Asn
                565                 570                 575
Ser Tyr Met Ser Ala Leu Phe Phe Ala Leu Ile Ile Leu Leu Val Asp
            580                 585                 590
Gly Phe Pro Glu Leu Ser Met Thr Ala Gln Arg Leu Ala Val Phe Tyr
        595                 600                 605
```

```
Lys Gln Lys Gln Leu Cys Phe Tyr Pro Ala Trp Ala Tyr Ala Ile Pro
610                 615                 620

Ala Thr Val Leu Lys Val Pro Leu Ser Phe Phe Glu Ser Leu Val Trp
625                 630                 635                 640

Thr Cys Leu Ser Tyr Tyr Val Ile Gly Tyr Thr Pro Glu Ala Ser Arg
                645                 650                 655

Phe Phe Lys Gln Phe Ile Leu Leu Phe Ala Val His Phe Thr Ser Ile
            660                 665                 670

Ser Met Phe Arg Cys Leu Ala Ala Ile Phe Gln Thr Val Val Ala Ser
        675                 680                 685

Ile Thr Ala Gly Ser Phe Gly Ile Leu Phe Thr Phe Val Phe Ala Gly
690                 695                 700

Phe Val Ile Pro Pro Ser Met Pro Ala Trp Leu Lys Trp Gly Phe
705                 710                 715                 720

Trp Ala Asn Pro Leu Ser Tyr Gly Glu Ile Gly Leu Ser Val Asn Glu
                725                 730                 735

Phe Leu Ala Pro Arg Trp Asn Gln Met Gln Pro Asn Asn Phe Thr Leu
                740                 745                 750

Gly Arg Thr Ile Leu Gln Thr Arg Gly Met Asp Tyr Asn Gly Tyr Met
            755                 760                 765

Tyr Trp Val Ser Leu Cys Ala Leu Leu Gly Phe Thr Val Leu Phe Asn
770                 775                 780

Ile Ile Phe Thr Leu Ala Leu Thr Phe Leu Lys Ser Pro Thr Ser Ser
785                 790                 795                 800

Arg Ala Met Ile Ser Gln Asp Lys Leu Ser Glu Leu Gln Gly Thr Glu
                805                 810                 815

Lys Ser Thr Glu Asp Ser Ser Val Arg Lys Lys Thr Thr Asp Ser Pro
                820                 825                 830

Val Lys Thr Glu Glu Glu Asp Lys Met Val Leu Pro Phe Lys Pro Leu
            835                 840                 845

Thr Val Thr Phe Gln Asp Leu Asn Tyr Phe Val Asp Met Pro Val Glu
850                 855                 860

Met Arg Asp Gln Gly Tyr Asp Gln Lys Lys Leu Gln Leu Leu Ser Asp
865                 870                 875                 880

Ile Thr Gly Ala Phe Arg Pro Gly Ile Leu Thr Ala Leu Met Gly Val
                885                 890                 895

Ser Gly Ala Gly Lys Thr Thr Leu Leu Asp Val Leu Ala Gly Arg Lys
            900                 905                 910

Thr Ser Gly Tyr Ile Glu Gly Asp Ile Arg Ile Ser Gly Phe Pro Lys
            915                 920                 925

Val Gln Glu Thr Phe Ala Arg Val Ser Gly Tyr Cys Glu Gln Thr Asp
930                 935                 940

Ile His Ser Pro Asn Ile Thr Val Glu Glu Ser Val Ile Tyr Ser Ala
945                 950                 955                 960

Trp Leu Arg Leu Ala Pro Glu Ile Asp Ala Thr Thr Lys Thr Lys Phe
                965                 970                 975

Val Lys Gln Val Leu Glu Thr Ile Glu Leu Asp Glu Ile Lys Asp Ser
            980                 985                 990

Leu Val Gly Val Thr Gly Val Ser  Gly Leu Ser Thr Glu  Gln Arg Lys
                995                 1000                1005

Arg Leu  Thr Ile Ala Val Glu  Leu Val Ala Asn Pro  Ser Ile Ile
    1010                1015                1020
```

```
Phe Met Asp Glu Pro Thr Thr Gly Leu Asp Ala Arg Ala Ala Ala
1025                1030                1035

Ile Val Met Arg Ala Val Lys Asn Val Ala Asp Thr Gly Arg Thr
1040                1045                1050

Ile Val Cys Thr Ile His Gln Pro Ser Ile Asp Ile Phe Glu Ala
1055                1060                1065

Phe Asp Glu Leu Val Leu Leu Lys Arg Gly Arg Met Ile Tyr
1070                1075                1080

Thr Gly Pro Leu Gly Gln His Ser Arg His Ile Ile Glu Tyr Phe
1085                1090                1095

Glu Ser Val Pro Glu Ile Pro Lys Ile Lys Asp Asn His Asn Pro
1100                1105                1110

Ala Thr Trp Met Leu Asp Val Ser Ser Gln Ser Val Glu Ile Glu
1115                1120                1125

Leu Gly Val Asp Phe Ala Lys Ile Tyr His Asp Ser Ala Leu Tyr
1130                1135                1140

Lys Arg Asn Ser Glu Leu Val Lys Gln Leu Ser Gln Pro Asp Ser
1145                1150                1155

Gly Ser Ser Asp Ile Gln Phe Lys Arg Thr Phe Ala Gln Ser Trp
1160                1165                1170

Trp Gly Gln Phe Lys Ser Ile Leu Trp Lys Met Asn Leu Ser Tyr
1175                1180                1185

Trp Arg Ser Pro Ser Tyr Asn Leu Met Arg Met Met His Thr Leu
1190                1195                1200

Val Ser Ser Leu Ile Phe Gly Ala Leu Phe Trp Lys Gln Gly Gln
1205                1210                1215

Asn Leu Asp Thr Gln Gln Ser Met Phe Thr Val Phe Gly Ala Ile
1220                1225                1230

Tyr Gly Leu Val Leu Phe Leu Gly Ile Asn Asn Cys Ala Ser Ala
1235                1240                1245

Leu Gln Tyr Phe Glu Thr Glu Arg Asn Val Met Tyr Arg Glu Arg
1250                1255                1260

Phe Ala Gly Met Tyr Ser Ala Thr Ala Tyr Ala Leu Gly Gln Val
1265                1270                1275

Val Thr Glu Ile Pro Tyr Ile Phe Ile Gln Ala Ala Glu Phe Val
1280                1285                1290

Ile Val Thr Tyr Pro Met Ile Gly Phe Tyr Pro Ser Ala Tyr Lys
1295                1300                1305

Val Phe Trp Ser Leu Tyr Ser Met Phe Cys Ser Leu Leu Thr Phe
1310                1315                1320

Asn Tyr Leu Ala Met Phe Leu Val Ser Ile Thr Pro Asn Phe Met
1325                1330                1335

Val Ala Ala Ile Leu Gln Ser Leu Phe Tyr Val Gly Phe Asn Leu
1340                1345                1350

Phe Ser Gly Phe Leu Ile Pro Gln Thr Gln Val Pro Gly Trp Trp
1355                1360                1365

Ile Trp Leu Tyr Tyr Leu Thr Pro Thr Ser Trp Thr Leu Asn Gly
1370                1375                1380

Phe Ile Ser Ser Gln Tyr Gly Asp Ile His Glu Glu Ile Asn Val
1385                1390                1395

Phe Gly Gln Ser Thr Thr Val Ala Arg Phe Leu Lys Asp Tyr Phe
1400                1405                1410

Gly Phe His His Asp Leu Leu Ala Val Thr Ala Val Val Gln Ile
```

-continued

```
        1415                1420                1425

Ala Phe Pro Ile Ala Leu Ala Ser Met Phe Ala Phe Phe Val Gly
        1430                1435                1440

Lys Leu Asn Phe Gln Arg Arg
        1445                1450

<210> SEQ ID NO 50
<211> LENGTH: 8
<212> TYPE: PRT
<213> ORGANISM: Artificial Sequence
<220> FEATURE:
<223> OTHER INFORMATION: Conserved domain of PDR ABC transporters
      present in Lr34

<400> SEQUENCE: 50

Gly Pro Pro Gly Cys Gly Lys Ser
1               5

<210> SEQ ID NO 51
<211> LENGTH: 8
<212> TYPE: PRT
<213> ORGANISM: Artificial Sequence
<220> FEATURE:
<223> OTHER INFORMATION: Conserved domain of PDR ABC transporters
      present in Lr34

<400> SEQUENCE: 51

Gly Val Ser Gly Ala Gly Lys Thr
1               5

<210> SEQ ID NO 52
<211> LENGTH: 12
<212> TYPE: PRT
<213> ORGANISM: Artificial Sequence
<220> FEATURE:
<223> OTHER INFORMATION: Conserved domain of PDR ABC transporters
      present in Lr34

<400> SEQUENCE: 52

Ile Ser Gly Gly Gln Lys Lys Arg Leu Thr Thr Ala
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Conserved domain of PDR ABC transporters
      present in Lr34

<400> SEQUENCE: 53

Leu Ser Met Glu Gln Arg Lys Arg Leu Thr Ile Ala
1               5                   10

<210> SEQ ID NO 54
<211> LENGTH: 5
<212> TYPE: PRT
<213> ORGANISM: Artificial Sequence
<220> FEATURE:
<223> OTHER INFORMATION: Conserved domain of PDR ABC transporters
      present in Lr34

<400> SEQUENCE: 54

Ala Tyr Phe Met Asp
1               5
```

```
-continued

<210> SEQ ID NO 55
<211> LENGTH: 5
<212> TYPE: PRT
<213> ORGANISM: Artificial Sequence
<220> FEATURE:
<223> OTHER INFORMATION: Conserved domain of PDR ABC transporters
      present in Lr34

<400> SEQUENCE: 55

Ile Ile Leu Met Asp
1               5

<210> SEQ ID NO 56
<211> LENGTH: 8
<212> TYPE: PRT
<213> ORGANISM: Artificial Sequence
<220> FEATURE:
<223> OTHER INFORMATION: Walker A consensus sequence
<220> FEATURE:
<221> NAME/KEY: MISC_FEATURE
<222> LOCATION: (2)..(2)
<223> OTHER INFORMATION: Xaa = Any amino acid
<220> FEATURE:
<221> NAME/KEY: MISC_FEATURE
<222> LOCATION: (3)..(3)
<223> OTHER INFORMATION: Xaa = Any amino acid
<220> FEATURE:
<221> NAME/KEY: MISC_FEATURE
<222> LOCATION: (4)..(4)
<223> OTHER INFORMATION: Xaa = Any amino acid
<220> FEATURE:
<221> NAME/KEY: MISC_FEATURE
<222> LOCATION: (5)..(5)
<223> OTHER INFORMATION: Xaa = Any amino acid
<220> FEATURE:
<221> NAME/KEY: MISC_FEATURE
<222> LOCATION: (8)..(8)
<223> OTHER INFORMATION: Xaa = Ser or Thr

<400> SEQUENCE: 56

Gly Xaa Xaa Xaa Xaa Gly Lys Xaa
1               5

<210> SEQ ID NO 57
<211> LENGTH: 5
<212> TYPE: PRT
<213> ORGANISM: Artificial Sequence
<220> FEATURE:
<223> OTHER INFORMATION: Walker B consensus sequence
<220> FEATURE:
<221> NAME/KEY: MISC_FEATURE
<222> LOCATION: (1)..(1)
<223> OTHER INFORMATION: Xaa = Phe, Ile, Trp, Leu, Val, Met, Tyr or Ala
<220> FEATURE:
<221> NAME/KEY: MISC_FEATURE
<222> LOCATION: (2)..(2)
<223> OTHER INFORMATION: Xaa = Phe, Ile, Trp, Leu, Val, Met, Tyr or Ala
<220> FEATURE:
<221> NAME/KEY: MISC_FEATURE
<222> LOCATION: (3)..(3)
<223> OTHER INFORMATION: Xaa = Phe, Ile, Trp, Leu, Val, Met, Tyr or Ala
<220> FEATURE:
<221> NAME/KEY: MISC_FEATURE
<222> LOCATION: (4)..(4)
<223> OTHER INFORMATION: Xaa = Phe, Ile, Trp, Leu, Val, Met, Tyr or Ala
<220> FEATURE:
<221> NAME/KEY: MISC_FEATURE
<222> LOCATION: (5)..(5)
<223> OTHER INFORMATION: Xaa = Asp or Glu

<400> SEQUENCE: 57

Xaa Xaa Xaa Xaa Xaa
1               5
```

```
<210> SEQ ID NO 58
<211> LENGTH: 12
<212> TYPE: PRT
<213> ORGANISM: Artificial Sequence
<220> FEATURE:
<223> OTHER INFORMATION: ABC signature consensus sequence
<220> FEATURE:
<221> NAME/KEY: MISC_FEATURE
<222> LOCATION: (1)..(1)
<223> OTHER INFORMATION: Xaa = Leu, Ile, Val, Met, Phe or Tyr
<220> FEATURE:
<221> NAME/KEY: MISC_FEATURE
<222> LOCATION: (3)..(3)
<223> OTHER INFORMATION: Xaa = Ser, Gly or Met
<220> FEATURE:
<221> NAME/KEY: MISC_FEATURE
<222> LOCATION: (4)..(4)
<223> OTHER INFORMATION: Xaa = Gly or Glu
<220> FEATURE:
<221> NAME/KEY: MISC_FEATURE
<222> LOCATION: (5)..(5)
<223> OTHER INFORMATION: Xaa = Any amino acid
<220> FEATURE:
<221> NAME/KEY: MISC_FEATURE
<222> LOCATION: (6)..(6)
<223> OTHER INFORMATION: Xaa = Any amino acid
<220> FEATURE:
<221> NAME/KEY: MISC_FEATURE
<222> LOCATION: (7)..(7)
<223> OTHER INFORMATION: Xaa = Any amino acid
<220> FEATURE:
<221> NAME/KEY: MISC_FEATURE
<222> LOCATION: (8)..(8)
<223> OTHER INFORMATION: Xaa = Arg, Lys or Ala
<220> FEATURE:
<221> NAME/KEY: MISC_FEATURE
<222> LOCATION: (9)..(9)
<223> OTHER INFORMATION: Xaa = Leu, Ile, Val, Met, Tyr or Ala
<220> FEATURE:
<221> NAME/KEY: MISC_FEATURE
<222> LOCATION: (10)..(10)
<223> OTHER INFORMATION: Xaa = Any amino acid
<220> FEATURE:
<221> NAME/KEY: MISC_FEATURE
<222> LOCATION: (11)..(11)
<223> OTHER INFORMATION: Xaa = Leu, Ile, Val, Met, Phe or Thr
<220> FEATURE:
<221> NAME/KEY: MISC_FEATURE
<222> LOCATION: (12)..(12)
<223> OTHER INFORMATION: Xaa = Ala or Gly

<400> SEQUENCE: 58

Xaa Ser Xaa Xaa Xaa Xaa Xaa Xaa Xaa Xaa Xaa Xaa
1               5                   10

<210> SEQ ID NO 59
<211> LENGTH: 6
<212> TYPE: PRT
<213> ORGANISM: Artificial Sequence
<220> FEATURE:
<223> OTHER INFORMATION: PDR signature 1

<400> SEQUENCE: 59

Leu Leu Leu Gly Pro Pro
1               5

<210> SEQ ID NO 60
<211> LENGTH: 6
<212> TYPE: PRT
<213> ORGANISM: Artificial Sequence
<220> FEATURE:
<223> OTHER INFORMATION: PDR signature 2

<400> SEQUENCE: 60
```

```
Gly Leu Asp Ser Ser Thr
1               5

<210> SEQ ID NO 61
<211> LENGTH: 12
<212> TYPE: PRT
<213> ORGANISM: Artificial Sequence
<220> FEATURE:
<223> OTHER INFORMATION: PDR signature 3
<220> FEATURE:
<221> NAME/KEY: MISC_FEATURE
<222> LOCATION: (4)..(4)
<223> OTHER INFORMATION: Xaa = Ala or Thr
<220> FEATURE:
<221> NAME/KEY: MISC_FEATURE
<222> LOCATION: (6)..(6)
<223> OTHER INFORMATION: Xaa = Ala or Ser
<220> FEATURE:
<221> NAME/KEY: MISC_FEATURE
<222> LOCATION: (11)..(11)
<223> OTHER INFORMATION: Xaa = Met or Ile

<400> SEQUENCE: 61

Gly Leu Asp Xaa Arg Xaa Ala Ala Ile Val Xaa Arg
1               5                   10

<210> SEQ ID NO 62
<211> LENGTH: 8
<212> TYPE: PRT
<213> ORGANISM: Artificial Sequence
<220> FEATURE:
<223> OTHER INFORMATION: PDR signature 4

<400> SEQUENCE: 62

Val Cys Thr Ile His Gln Pro Ser
1               5

<210> SEQ ID NO 63
<211> LENGTH: 1405
<212> TYPE: PRT
<213> ORGANISM: Triticum aestivum

<400> SEQUENCE: 63

Met Glu Gly Leu Ala Arg Glu Thr Asn Pro Ser Ser His His Gln Asp
1               5                   10                  15

Phe Ala Ser Cys Ala Ser Asp Glu Arg Pro Asp Glu Pro Glu Leu Glu
                20                  25                  30

Leu Ala Ser Arg Arg Gln Asn Gly Ala Gly Asn Asn Glu His Val
            35                  40                  45

Ser Glu Asn Met Leu Leu Asp Ser Ser Lys Phe Gly Ala Leu Lys Arg
    50                  55                  60

Arg Glu Phe Phe Asn Asn Leu Leu Lys Asn Leu Glu Asp Asp His Pro
65                  70                  75                  80

Arg Phe Leu Arg Arg Gln Lys Glu Arg Ile Asp Arg Val Asp Val Lys
                85                  90                  95

Leu Pro Ala Ile Glu Val Arg Tyr Asn Asn Leu Phe Val Glu Ala Glu
                100                 105                 110

Cys Arg Val Thr Lys Gly Asn His Leu Pro Ser Leu Trp Asn Ser Thr
            115                 120                 125

Lys Gly Ala Phe Ser Gly Leu Val Lys Leu Gly Phe Glu Thr Glu
    130                 135                 140

Arg Ala Lys Thr Asn Val Leu Glu Asp Val Ser Gly Ile Ile Lys Pro
145                 150                 155                 160
```

```
Cys Arg Leu Thr Leu Leu Leu Gly Pro Pro Gly Cys Gly Lys Ser Thr
                165                 170                 175
Leu Leu Arg Ala Leu Ala Gly Lys Leu Asp Lys Ser Leu Lys Val Thr
            180                 185                 190
Gly Asp Ile Ser Tyr Asn Cys Tyr Glu Leu His Glu Phe Val Pro Glu
        195                 200                 205
Lys Thr Ala Val Tyr Ile Asn Gln His Asp Leu His Ile Ala Glu Met
    210                 215                 220
Thr Val Arg Glu Thr Leu Asp Phe Ser Ala Gln Cys Gln Gly Val Gly
225                 230                 235                 240
Arg Arg Pro Lys Ile Leu Lys Glu Val Asn Thr Arg Glu Ser Val Ala
                245                 250                 255
Gly Ile Ile Pro Asp Ala Asp Ile Asp Leu Tyr Met Lys Val Val Ala
            260                 265                 270
Val Glu Ala Ser Glu Arg Ser Leu Gln Thr Asp Tyr Ile Leu Lys Ile
        275                 280                 285
Met Gly Leu Glu Thr Cys Ala Asp Thr Met Val Gly Asp Ala Met Arg
    290                 295                 300
Arg Gly Ile Ser Gly Gln Lys Lys Arg Leu Thr Thr Ala Glu Met
305                 310                 315                 320
Ile Val Gly Pro Ala Lys Ala Tyr Phe Met Asp Glu Ile Ser Asn Gly
                325                 330                 335
Leu Asp Ser Ser Thr Thr Phe Gln Ile Ile Asn Cys Phe Gln Gln Leu
            340                 345                 350
Thr Asn Ile Ser Glu Tyr Thr Met Val Ile Ser Leu Leu Gln Pro Thr
        355                 360                 365
Pro Glu Val Phe Asp Leu Phe Asp Asp Leu Ile Leu Met Ala Glu Gly
    370                 375                 380
Lys Ile Ile Tyr His Gly Pro Arg Asn Glu Ala Leu Asn Phe Phe Glu
385                 390                 395                 400
Glu Cys Gly Phe Lys Cys Pro Glu Arg Lys Ala Ala Ala Asp Phe Leu
                405                 410                 415
Gln Glu Ile Leu Ser Arg Lys Asp Gln Glu Gln Tyr Trp Leu Gly Pro
            420                 425                 430
His Glu Ser Tyr Arg Tyr Ile Ser Pro His Glu Leu Ser Ser Met Phe
        435                 440                 445
Lys Glu Asn His Arg Gly Arg Lys Leu His Glu Gln Ser Val Pro Pro
    450                 455                 460
Lys Ser Gln Phe Gly Lys Glu Ala Leu Ala Phe Asn Lys Tyr Ser Leu
465                 470                 475                 480
Arg Lys Leu Glu Met Phe Lys Ala Cys Gly Ala Arg Glu Ala Leu Leu
                485                 490                 495
Met Lys Arg Asn Met Phe Val Tyr Val Phe Lys Thr Gly Gln Leu Ala
            500                 505                 510
Ile Ile Ala Leu Val Thr Met Ser Val Phe Leu Arg Thr Arg Met Thr
        515                 520                 525
Ile Ser Phe Thr His Ala Asn Tyr Tyr Met Gly Ala Leu Phe Phe Ser
    530                 535                 540
Ile Phe Met Ile Met Leu Asn Gly Ile Pro Glu Met Ser Met Gln Ile
545                 550                 555                 560
Gly Arg Leu Pro Ser Phe Tyr Lys Gln Lys Ser Tyr Tyr Phe Tyr Ser
                565                 570                 575
```

```
Ser Trp Ala Tyr Ala Ile Pro Ala Ser Val Leu Lys Val Pro Val Ser
            580                 585                 590

Ile Leu Asp Ser Leu Val Trp Ile Ser Ile Thr Tyr Tyr Gly Ile Gly
        595                 600                 605

Tyr Thr Pro Thr Val Ser Arg Phe Phe Cys Gln Phe Leu Ile Leu Cys
    610                 615                 620

Leu Leu His His Ser Val Thr Ser Gln Tyr Arg Phe Ile Ala Ser Tyr
625                 630                 635                 640

Phe Gln Thr Pro Ile Val Ser Phe Phe Tyr Leu Phe Leu Ala Leu Thr
                645                 650                 655

Val Phe Leu Thr Phe Gly Gly Phe Ile Leu Pro Lys Thr Ser Met Pro
            660                 665                 670

Glu Trp Leu Asn Trp Gly Phe Trp Ile Ser Pro Met Ala Tyr Ala Glu
        675                 680                 685

Ile Ser Ile Val Ile Asn Glu Phe Leu Ala Pro Arg Trp Gln Lys Glu
    690                 695                 700

Ser Ile Gln Asn Ile Thr Ile Gly Asn Gln Ile Leu Val Asn His Gly
705                 710                 715                 720

Leu Tyr Tyr Ser Trp His Phe Tyr Trp Ile Ser Phe Gly Ala Leu Leu
                725                 730                 735

Gly Ser Ile Leu Leu Phe Tyr Ile Ala Phe Gly Leu Ala Leu Asp Tyr
            740                 745                 750

Arg Thr Pro Thr Glu Glu Tyr His Gly Ser Arg Pro Thr Lys Ser Leu
        755                 760                 765

Cys Gln Gln Gln Glu Lys Asp Ser Thr Ile Gln Asn Glu Ser Asp Asp
    770                 775                 780

Gln Ser Asn Ile Ser Lys Ala Lys Met Thr Ile Pro Thr Met His Leu
785                 790                 795                 800

Pro Ile Thr Phe His Asn Leu Asn Tyr Tyr Ile Asp Thr Pro Pro Glu
                805                 810                 815

Met Leu Lys Gln Gly Tyr Pro Thr Arg Arg Leu Arg Leu Leu Asn Asn
            820                 825                 830

Ile Thr Gly Ala Leu Arg Pro Gly Val Leu Ser Ala Leu Met Gly Val
        835                 840                 845

Ser Gly Ala Gly Lys Thr Thr Leu Leu Asp Val Leu Ala Gly Arg Lys
    850                 855                 860

Thr Gly Gly Tyr Ile Glu Gly Asp Ile Arg Ile Gly Gly Tyr Pro Lys
865                 870                 875                 880

Val Gln Glu Thr Phe Val Arg Ile Leu Gly Tyr Cys Glu Gln Val Asp
                885                 890                 895

Ile His Ser Pro Gln Leu Thr Val Glu Glu Ser Val Thr Tyr Ser Ala
            900                 905                 910

Trp Leu Arg Leu Pro Ser His Val Asp Lys Gln Thr Arg Ser Lys Phe
        915                 920                 925

Val Ala Glu Val Leu Glu Thr Val Glu Leu Asp Gln Ile Lys Asp Val
    930                 935                 940

Leu Val Gly Ser Pro Gln Lys Asn Gly Leu Ser Met Glu Gln Arg Lys
945                 950                 955                 960

Arg Leu Thr Ile Ala Val Glu Leu Val Ser Asn Pro Ser Ile Ile Leu
                965                 970                 975

Met Asp Glu Pro Thr Thr Gly Leu Asp Thr Arg Ser Ala Ala Ile Val
            980                 985                 990

Ile Arg Ala Val Lys Asn Ile Cys  Glu Thr Gly Arg Thr  Val Val Cys
```

```
            995                 1000                1005
Thr  Ile  His  Gln  Pro  Ser  Thr  Glu  Ile  Phe  Glu  Ala  Phe  Asp  Glu
          1010                 1015                1020

Leu  Ile  Leu  Met  Lys  Thr  Gly  Gly  Lys  Thr  Ile  Tyr  Asn  Gly  Pro
          1025                 1030                1035

Ile  Gly  Glu  Arg  Ser  Cys  Lys  Val  Ile  Glu  Tyr  Phe  Glu  Lys  Ile
          1040                 1045                1050

Ser  Gly  Val  Pro  Lys  Ile  Lys  Ser  Asn  Cys  Asn  Pro  Ala  Thr  Trp
          1055                 1060                1065

Met  Met  Asp  Val  Thr  Ser  Thr  Ser  Met  Glu  Val  Gln  His  Asn  Met
          1070                 1075                1080

Asp  Phe  Ala  Ile  Leu  Tyr  Glu  Glu  Ser  Ser  Leu  His  Arg  Glu  Ala
          1085                 1090                1095

Glu  Asp  Leu  Val  Glu  Gln  Leu  Ser  Ile  Pro  Leu  Pro  Asn  Ser  Glu
          1100                 1105                1110

Asn  Leu  Arg  Phe  Ser  His  Ser  Phe  Ala  Gln  Asn  Gly  Trp  Ile  Gln
          1115                 1120                1125

Leu  Lys  Ala  Cys  Leu  Trp  Lys  Gln  Asn  Ile  Thr  Tyr  Trp  Arg  Ser
          1130                 1135                1140

Pro  Gln  Tyr  Asn  Leu  Arg  Arg  Ile  Met  Met  Thr  Val  Ile  Ser  Ala
          1145                 1150                1155

Leu  Ile  Tyr  Gly  Val  Leu  Phe  Trp  Lys  His  Ala  Lys  Val  Leu  Asn
          1160                 1165                1170

Asn  Glu  Gln  Asp  Met  Leu  Ser  Val  Phe  Gly  Ala  Met  Tyr  Leu  Gly
          1175                 1180                1185

Phe  Thr  Thr  Ile  Gly  Ala  Tyr  Asn  Asp  Gln  Thr  Ile  Ile  Pro  Phe
          1190                 1195                1200

Ser  Thr  Thr  Glu  Arg  Ile  Val  Met  Tyr  Arg  Glu  Lys  Phe  Ala  Gly
          1205                 1210                1215

Met  Tyr  Ser  Ser  Trp  Ser  Tyr  Ser  Phe  Ala  Gln  Ala  Phe  Ile  Glu
          1220                 1225                1230

Ile  Pro  Tyr  Val  Phe  Ile  Gln  Val  Val  Leu  Tyr  Thr  Leu  Ile  Val
          1235                 1240                1245

Tyr  Pro  Ser  Thr  Gly  Tyr  Tyr  Trp  Thr  Ala  His  Lys  Phe  Leu  Trp
          1250                 1255                1260

Phe  Phe  Tyr  Thr  Thr  Phe  Cys  Ser  Ile  Leu  Ser  Tyr  Val  Tyr  Val
          1265                 1270                1275

Gly  Leu  Leu  Leu  Val  Ser  Ile  Thr  Pro  Asn  Val  Gln  Val  Ala  Thr
          1280                 1285                1290

Ile  Leu  Ala  Ser  Phe  Phe  Asn  Thr  Met  Gln  Thr  Leu  Phe  Ser  Gly
          1295                 1300                1305

Phe  Ile  Leu  Pro  Ala  Pro  Thr  Leu  Gln  Gln  Ile  Pro  Lys  Trp  Trp
          1310                 1315                1320

Thr  Trp  Leu  Tyr  Tyr  Leu  Thr  Pro  Thr  Ser  Trp  Ala  Leu  Asn  Ala
          1325                 1330                1335

Leu  Leu  Thr  Ser  Gln  Tyr  Gly  Asn  Ile  Glu  Lys  Glu  Val  Lys  Ala
          1340                 1345                1350

Phe  Gly  Glu  Thr  Lys  Ser  Val  Ser  Ile  Phe  Leu  Asn  Asp  Tyr  Phe
          1355                 1360                1365

Gly  Phe  His  Gln  Asp  Lys  Leu  Ser  Ile  Val  Ala  Thr  Val  Leu  Val
          1370                 1375                1380
```

```
Ala Phe Pro Phe Val Leu Ile Ile Leu Phe Ser Leu Ser Ile Glu
    1385               1390               1395

Lys Leu Asn Phe Gln Lys Arg
    1400               1405

<210> SEQ ID NO 64
<211> LENGTH: 4218
<212> TYPE: DNA
<213> ORGANISM: Triticum aestivum

<400> SEQUENCE: 64
atggagggcc tcgcgagaga gaccaaccca tcatcccacc atcaagattt cgcctcctgc      60
gcgagtgacg agcgcccgga tgagcccgag ttggaattgg catcgcgacg gcgccagaat     120
ggtgctggaa caacgagca tgtgagtgag aacatgctgc ttgacagcag caagtttgga     180
gctctcaaga ggcgtgagtt cttcaacaac ctgctaaaga acctcgaaga cgaccacccc     240
cgctttctgc gcagacaaaa ggaaagaatt gacagggttg atgtcaagtt gccagcaata     300
gaggtgaggt ataataatct gtttgtggaa gcagagtgca gagttactaa aggaaatcac     360
ctgccgtctc tatggaatag taccaaaggt gccttctcgg gcctcgtgaa gttgctaggc     420
ttcgaaacgg aaagagcaaa accaacgtt ctagaagatg tcagtggaat catcaaaccc     480
tgcagattga ctcttctact gggacctcct ggatgtggca aaagcactct gttgcgagct     540
cttgccggga aactagataa atctctaaag gtaacagggg atatctctta taattgttat     600
gaacttcatg aatttgtacc tgagaaaaca gctgtgtata tcaaccaaca tgatctgcac     660
atagctgaga tgactgtgag ggaaacttta gacttctcag cccagtgcca aggtgttgga     720
agaagaccaa aaatactcaa ggaggtgaac acaaggggaga gtgtggctgg gatcataacc     780
gatgcggaca tcgatctata catgaaggta gtagcagttg aagcttcaga gcgaagccta     840
cagacagatt atattttgaa gatcatgggg ctagagacat gcgcagacac gatggttggg     900
gatgcaatga aagaggaat atcaggggggg cagaagaaaa gattaaccac agccgagatg     960
attgtgggac ccgcaaaagc atactttatg gatgaaatat caaatggtct ggatagctct    1020
accacttttc aaataatcaa ttgtttccag caactgacaa catcagcga gtacacgatg    1080 gttatttcac ttcttcaacc aacacctgag gtatttgatc ttttcgatga cctcatacta    1140
atggcagaag ggaagattat ctaccatggc cctcgaaatg aagccctcaa ttttttttgag    1200 gagtgtgggt tcaaatgccc agaaagaaaa gcggcagctg actttctcca agagatcttg    1260
tccaggaagg accaagaaca gtactggttg ggtccacatg aatcatacag atatatctca    1320
cctcatgaat tatcaagcat gttcaaggag aatcacaggg ggagaaaact acatgaacaa    1380
agtgtacctc ccaaaagcca gttcggcaag gaagctttag cattcaataa gtattcgcta    1440
cgaaaactgg aaatgttcaa agcctgtgga gcaagggaag cactcctaat gaaaaggaat    1500
atgtttgttt atgtcttcaa aacaggccag cttgccatta ttgcactcgt aacaatgtct    1560
gtattccttc gaactcgcat gacaataagt ttcactcatg caattactac tatgggagca    1620
ttattttttt ccatcttcat gattatgcta aatggcatac cagagatgag catgcagatt    1680
gggagactcc caagttttta caaacaaaag agctactatt tctattcatc atgggcatat    1740
gcaataccag cttcagtcct aaaggtccct gttttccatac tggattcgct tgtatggata    1800
tctatcacat attatggtat tggttataca cctactgttt caaggttctt ctgccagtttt    1860 ctgatacttt gtcttctcca tcattcagtc acctcgcagt atcgatttat tgcttcatac    1920
```

```
ttccaaacac ctattgtgtc tttcttctac cttttttcttg ctctaacagt attccttaca   1980
ttcggaggct tcattcttcc caagacctcc atgccagaat ggctaaactg gggattttgg   2040
atatctccaa tggcatatgc agaaatcagc atagttatta acgagttctt ggcaccaaga   2100
tggcagaagg aaagtattca aaacataaca attgggaacc aaatcctggt taatcacggc   2160
ctatattaca gttggcattt ttattggata tcctttggag ccttgcttgg atctattctt   2220
ttattttata tcgcttttgg attggcacta gattacagaa cacctacaga agaatatcat   2280
ggaagcaggc ctacaaagag cttatgtcaa cagcaggaaa aagattccac tattcaaaat   2340
gaatctgatg atcaatcaaa tatttccaaa gcaaagatga ctataccaac tatgcatctt   2400
ccaattacat tccacaatct gaactactac attgataccc caccggaaat gctgaaacaa   2460
ggctatccaa caagaagact tcgactgctt aataacataa ctggagcttt acgtcccggt   2520
gttctttctg cactaatggg tgttagtgga gctgggaaga caactctact agatgtatta   2580
gcaggaagga aaacaggagg ttatattgaa ggggacataa aataggtgg atatcccaag   2640
gtgcaggaaa catttgtcag aatcttgggt tactgcgaac aagtcgacat acattcccca   2700
cagcttacag ttgaagagtc tgtaacttat tctgcgtggc ttcgtctgcc ttctcatgtc   2760
gacaaacaaa caagatctaa atttgttgct gaagtccttg aaactgttga actagatcaa   2820
ataaaagatg tcttagtggg gtcaccacag aaaaatggat tgtccatgga gcagagaaag   2880
aggctaacga ttgcagtcga gcttgtttca aacccatcaa tcatactaat ggatgaacca   2940
acaacaggtt tagatacaag gtcagcagcc attgttattc gtgcagtcaa aaatatttgt   3000
gaaacaggaa ggacggtagt ctgtacaatc catcagccga gcactgaaat ttttgaggca   3060
tttgatgagc tcatattaat gaaaaccggt gggaaaacaa tctacaatgg accaatagga   3120
gagcgctcct gcaaagtgat tgagtacttt gagaaaattt ctggagtccc aaaaataaag   3180
agtaactgca atccagctac ctggatgatg gatgtaacat cgacatcaat ggaggttcaa   3240
cacaacatgg actttgcaat tttgtatgaa gagtcgtcac tgcatagaga agctgaagat   3300
ctagtggagc agctaagtat cccattacca aattcagaaa atctacgctt ctcccatagt   3360
tttgcacaga atggctggat tcaacttaaa gcttgcttgt ggaaacaaaa cataacttac   3420
tggagaagtc ctcagtataa cttgaggcgc attatgatga ctgtcatatc tgccctgatc   3480
tacgagtat tgttctggaa gcatgcaaaa gtattaaaca acgagcagga catgctcagt   3540
gtttttggtg caatgtatt gggttcaca accataggcg cttataatga tcagacaatc   3600
ataccattca gtacgactga gcgtattgta atgtatcgtg agaaatttgc aggaatgtat   3660
tcatcttggt catattcatt cgcacaggct ttcattgaga tacctatgt atttatccaa   3720
gtggtactgt atacgttaat tgtctatccg tcaactggtt attattggac agcacacaaa   3780
ttcctatggt tcttctacac tacattttgt tcaattctct cctatgttta tgttgggttg   3840
cttcttgttt caataacccc caatgttcaa gtagctacca tactggcttc attttttcaac   3900
accatgcaaa cactattctc aggatttatt ttacctgcac ctacgttgca gcaaatccca   3960
aagtggtgga cttggctcta ctatctcact cctacatctt gggcactcaa tgccctcttg   4020
acatcacaat acgaaacat agaaaaagag gtgaaagcat tggagaaaac taaatcagtt   4080
tcaatcttct tgaatgacta ttttgggttt catcaagaca agttgagcat agtagcaact   4140
gtcctcgttg cctttccttt tgtgttgata atcttgtttt cgttgtccat tgagaaactt   4200
aatttccaga agaggtaa                                                 4218
```

RESISTANCE GENES

FIELD OF THE INVENTION

The present invention relates to polynucleotides encoding adult plant pathogen resistance proteins. Also provided are transgenic plants expressing these polynucleotides to enhance the resistance of the plants to pathogens.

BACKGROUND OF THE INVENTION

Numerous genes conferring resistance to pathogens have been identified and used in plant breeding. However, single-gene pathogen resistance in plants often becomes ineffective due to the emergence of new virulent races of the disease agent. In contrast, durable disease resistance in plants is generally thought to be controlled by multiple genes.

The wheat (*Triticum aestivum*) quantitative trait locus, Lr34, provides durable adult plant resistance to the biotrophic fungi causing the diseases leaf rust, stripe rust, stem rust and powdery mildew (Dyck, 1977 and 1987; German and Kolmer, 1992; Bossolini et al. 2006; Spielmeyer et al. 2008). This is despite the limitation that it is not effective at the seedling stage under normal field conditions. Cultivars with the resistance locus Lr34 such as Frontana have had effective durable resistance to the leaf rust fungus *Puccinia triticina* Eriks (Dyck et al., 1966; Singh and Rajaram, 1994). To date, isolates of *P. triticina* with complete virulence to Lr34 have not been detected (Kolmer et al., 2003).

Lr34 resistance has remained genetically inseparable from Yr18 that confers resistance to stripe rust (*P. striiformis*) (Singh, 1992a; McIntosh, 1992). Co-segregation of Lr34/Yr18 with other traits such as leaf tip necrosis (Ltn1), powdery mildew (recently designated Pm38), tolerance to barley yellow dwarf virus (Bdv1) and spot blotch (*Bipolaris sorokiniana*) have been documented (Singh, 1992a, b; McIntosh, 1992; Joshi et al., 2004; Spielmeyer et al., 2005; Liang et al., 2006). These multi-pathogen resistance traits have made the Lr34/Yr18 locus one of the most valuable gene regions for disease resistance breeding in wheat.

A few rust resistance genes have been isolated and cloned from wheat (Feuillet et al., 2003; Huang et al., 2003; Cloutier et al., 2007) and other cereals (Collins et al., 1999; Brueggeman et al., 2002) and are predominantly from the nucleotide binding site-leucine rich repeat (NB-LRR) class of major resistance (R) genes. The only known exception is the barley Rpg1 rust resistance gene which encodes a protein kinase. These genes encode gene-for-gene resistance against single pathogens and generally lead to hypersensitive responses in the plant tissues upon infection. In contrast, Lr34 confers a broad spectrum resistance against several obligate biotrophic pathogens including fungi from the Ascomycetes and Basidiomycetes. Rubiales and Niks (1995) reported that Lr34 is associated with reduced intercellular hyphal growth but not with a hypersensitive response or papilla formation.

The molecular basis of quantitative non-race-specific, adult plant pathogen resistance-type or partial resistance encoded by genetic systems such as, for example, Lr34 therefore remains unknown.

SUMMARY OF THE INVENTION

The present inventors have identified genes and polypeptides which confer enhanced plant pathogen resistance to adult plants.

Accordingly, the present invention provides a transgenic plant which has integrated into its genome an exogenous polynucleotide encoding an adult plant pathogen resistance polypeptide and/or an exogenous polynucleotide which increases transcription of an endogenous gene encoding an adult plant pathogen resistance polypeptide.

In a preferred embodiment, the plant has accelerated senescence of flag leaf tips when compared to an isogenic plant lacking the exogenous polynucleotide.

In another preferred embodiment, the plant has enhanced resistance to a plant pathogen when compared to an isogenic plant lacking the exogenous polynucleotide.

In yet a further preferred embodiment, the polypeptide comprises amino acids having a sequence as provided in SEQ ID NO:1, a biologically active fragment thereof, or an amino acid sequence which is at least 40% identical, more preferably at least 80% identical, more preferably at least 90% identical, and even more preferably at least 95% identical, to SEQ ID NO:1. More preferably, the polypeptide comprises amino acids having a sequence as provided in SEQ ID NO:1.

In another preferred embodiment, the polynucleotide comprises nucleotides having a sequence as provided in SEQ ID NO:2, a sequence which is at least 40% identical to SEQ ID NO:2, and/or a sequence which hybridizes to SEQ ID NO:2.

In another embodiment, the exogenous polynucleotide which increases transcription of an endogenous gene encoding an adult plant pathogen resistance polypeptide is a genetic element, such as a promoter, which enhances the function of the endogenous gene promoter. Alternatively, the exogenous polynucleotide which increases transcription of an endogenous gene encoding an adult plant pathogen resistance polypeptide encodes a transcription factor which enhances expression of the endogenous gene.

Preferably, the plant is a cereal plant. Examples of transgenic cereal plants of the invention include, but are not limited to wheat, barley, maize, rice, oats and triticale. In a particularly preferred embodiment, the plant is wheat.

Examples of plant pathogens include, but are not limited to viruses, bacteria and fungi.

In a preferred embodiment, the pathogen is a biotrophic fungus. Examples of biotrophic fungi include, but are not limited to, *Fusarium graminearum* (which causes head blight), *Erysiphe graminis f.* sp. *tritici* (which causes powdery mildew), *Bipolaris sorokiniana* (which causes spot blotch), *Puccinia graminis f.* sp. *tritici* (which causes stem rust), *Puccinia striiformis* (which causes stripe rust) and *Puccinia recondite f.* sp. *tritici* (which causes leaf rust).

In an embodiment, the pathogen is barley yellow dwarf virus (BYDV).

In an embodiment, the plant comprises one or more further exogenous polynucleotides encoding a plant pathogen resistance polypeptide. Examples of such genes include, but are not limited to, Lr1, Lr3, Lr2a, Lr3ka, Lr11, Lr13, Lr16, Lr17, Lr18, Lr21 and LrB.

In another aspect, the present invention provides a process for identifying a polynucleotide encoding a plant pathogen resistance polypeptide comprising:

(i) obtaining a polynucleotide operably linked to a promoter, the polynucleotide encoding a polypeptide comprising amino acids having a sequence as provided in SEQ ID NO:1, a biologically active fragment thereof, or an amino acid sequence which is at least 40% identical to SEQ ID NO:1, (ii) introducing the polynucleotide into a plant, (iii) determining whether the level of resistance to a plant pathogen is modified relative to an isogenic plant lacking the polynucleotide, and (iv) optionally, selecting a polynucleotide which when expressed enhances resistance to the plant pathogen.

Preferably, the polynucleotide comprises nucleotides having a sequence as provided in SEQ ID NO:2, a sequence which is at least 40% identical to SEQ ID NO:2, and/or a sequence which hybridizes to SEQ ID NO:2.

Preferably, the plant is a cereal plant.

Preferably, the cereal plant is a wheat plant.

In a preferred embodiment, the polypeptide is a plant polypeptide or mutant thereof.

In a further embodiment, step (ii) further comprises stably integrating the polynucleotide operably linked to a promoter into the genome of the plant.

In yet another aspect, the present invention provides a substantially purified and/or recombinant adult plant pathogen resistance polypeptide.

In a preferred embodiment, the polypeptides comprises amino acids having a sequence as provided in SEQ ID NO:1, a biologically active fragment thereof, or an amino acid sequence which is at least 40% identical, more preferably at least 80% identical, more preferably at least 90% identical, and even more preferably at least 95% identical, to SEQ ID NO:1.

In a preferred embodiment, the polypeptide lacks a phenylalanine residue or any amino acid at a position corresponding to amino acid number 546 of SEQ ID NO:4.

In another preferred embodiment, the polypeptide has an amino acid other than a tyrosine residue at a position corresponding to amino acid number 634 of SEQ ID NO:4. More preferably, the polypeptide comprises a histidine residue at a position corresponding to amino acid number 634 of SEQ ID NO:4.

Also provided is a fusion protein further comprising at least one other polypeptide sequence. The at least one other polypeptide may be, for example, a polypeptide that enhances the stability of a polypeptide of the present invention, or a polypeptide that assists in the purification or detection of the fusion protein.

In a further aspect, the present invention provides an isolated and/or exogenous polynucleotide comprising nucleotides having a sequence as provided in SEQ ID NO:2, a sequence which is at least 40% identical to SEQ ID NO:2, a sequence encoding a polypeptide of the invention, and/or a sequence which hybridizes to SEQ ID NO:2.

Preferably, the polynucleotide comprises a sequence of nucleotides which hybridizes to SEQ ID NO:2 under stringent conditions.

Preferably, the polynucleotide hybridizes along the full length of a polynucleotide consisting of nucleotides having the sequence of SEQ ID NO:2.

Preferably, the polynucleotide encodes an adult plant pathogen resistance polypeptide.

In a further aspect, the present invention provides a chimeric vector comprising the polynucleotide of the invention.

Preferably, the polynucleotide is operably linked to a promoter.

In a further aspect, the present invention provides a recombinant cell comprising an exogenous polynucleotide of the invention and/or a vector of the invention.

The cell can be any cell type such as, but not limited to, a plant cell, a bacterial cell, an animal cell or a yeast cell.

Preferably, the cell is a plant cell. More preferably, the plant cell is a cereal plant cell. Even more preferably, the cereal plant cell is a wheat cell.

In a further aspect, the present invention provides a method of producing the polypeptide of the invention, the method comprising expressing in a cell or cell free expression system the polynucleotide of the invention.

Preferably, the method further comprises isolating the polypeptide.

In yet another aspect, the present invention provides a transgenic non-human organism comprising an exogenous polynucleotide of the invention, a vector of the invention and/or a recombinant cell of the invention.

Preferably, the transgenic non-human organism is a plant.

In another aspect, the present invention provides a method of producing the cell of the invention, the method comprising the step of introducing the polynucleotide of the invention, or a vector of the invention, into a cell.

Preferably, the cell is a plant cell.

In a further aspect, the present invention provides a method of producing a transgenic plant, the method comprising regenerating a transgenic plant from the cell of the invention.

Also provided is the use of the polynucleotide of the invention, or a vector of the invention, to produce a recombinant cell.

Further, provided is the use of the polynucleotide of the invention, or a vector of the invention, to produce a transgenic plant.

Preferably, the transgenic plant has accelerated senescence of flag leaf tips when compared to an isogenic plant lacking the exogenous polynucleotide and/or vector, and/or has enhanced resistance to a plant pathogen when compared to an isogenic plant lacking the exogenous polynucleotide and/or vector.

In another aspect, the present invention provides a transgenic plant, or progeny thereof, produced using a method of the invention.

In a further aspect, the present invention provides a plant part of the plant of the invention.

Examples of such plant parts include, but are not limited to, leaves, roots, stems and/or seeds. In a preferred embodiment, the plant part is a seed that comprises an exogenous polynucleotide encoding an adult plant pathogen resistance polypeptide.

In another aspect, the present invention provides a method of producing a plant part, the method comprising, a) growing a plant of the invention, and b) harvesting the plant part.

In yet a further aspect, the present invention provides a method of producing flour, wholemeal, starch or other product obtained from seed, the method comprising;

a) obtaining seed of the invention, and b) extracting the flour, wholemeal, starch or other product.

In another aspect, the present invention provides a product produced from a plant of the invention and/or a plant part of the invention.

In one embodiment, the product is a food product. Examples include, but are not limited to, flour, starch, leavened or unleavened breads, pasta, noodles, animal fodder, breakfast cereals, snack foods, cakes, malt, beer, pastries and foods containing flour-based sauces.

In another embodiment, the product is a non-food product. Examples include, but are not limited to, films, coatings, adhesives, building materials and packaging materials.

In a further aspect, the present invention provides a method of preparing a food product of the invention, the method comprising mixing seed, or flour, wholemeal or starch from said seed, with another ingredient.

In a further aspect, the present invention provides a method of preparing malt, comprising the step of germinating the seed of the invention.

In another embodiment, the present invention provides a composition comprising a polypeptide of the invention, a polynucleotide of the invention, a vector of the invention, and/or recombinant cell of the invention, and one or more acceptable carriers.

In another aspect, the present invention provides a substantially purified antibody, or fragment thereof, that specifically binds a polypeptide of the invention.

Also provided is a method of identifying a compound that binds to a polypeptide comprising amino acids having a sequence as provided in SEQ ID NO:1 or SEQ ID NO:4, a biologically active fragment thereof, or an amino acid sequence which is at least 40% identical to SEQ ID NO:1 and/or SEQ ID NO:4, the method comprising:

i) contacting the polypeptide with a candidate compound, and ii) determining whether the compound binds the polypeptide.

Further, provided is a method of identifying a compound that is transported across a cell membrane by a polypeptide comprising amino acids having a sequence as provided in SEQ ID NO:1 or SEQ ID NO:4, a biologically active fragment thereof, or an amino acid sequence which is at least 40% identical to SEQ ID NO:1 and/or SEQ ID NO:4, the method comprising:

i) contacting the polypeptide present in a cell membrane with a candidate compound, ii) determining whether the polypeptide transports the compound across the cell membrane.

Preferably, the polypeptide is expressed in a cell.

Preferably, the cell is a plant cell.

In an embodiment, the method further comprises comparing the binding, and/or transport, of the compound to a first polypeptide comprising an amino acid sequence provided as SEQ ID NO:1 to a second polypeptide comprising an amino acid sequence provided as SEQ ID NO:4.

In a further aspect, the present invention provides an isolated and/or exogenous polynucleotide which, when present in a cell of a plant, decreases the expression of at least one gene that hybridises under stringent conditions to a nucleic acid molecule encoding a polypeptide comprising amino acids having a sequence as provided in SEQ ID NO:1 or SEQ ID NO:4, a biologically active fragment thereof, or an amino acid sequence which is at least 40% identical to SEQ ID NO:1 and/or SEQ ID NO:4, said decreased expression being relative to an otherwise isogenic cell of a plant that lacks said polynucleotide.

In an embodiment, the polynucleotide encodes an adult plant pathogen resistance polypeptide.

Preferably, the polynucleotide of this aspect is operably linked to a promoter capable of directing expression of the polynucleotide in a cell of a plant.

Preferably, the polynucleotide of this aspect is an antisense polynucleotide, a sense polynucleotide, a catalytic polynucleotide, an artificial microRNA or a duplex RNA molecule.

In a further aspect, the present invention provides a method of identifying a plant comprising a gene encoding an adult plant pathogen resistance polypeptide, the method comprising i) amplifying and/or sequencing, from a sample of the plant, at least a portion of a polynucleotide which encodes a polypeptide comprising amino acids having a sequence as provided in SEQ ID NO:1 or SEQ ID NO:4, a biologically active fragment thereof, or an amino acid sequence which is at least 40% identical to SEQ ID NO:1 and/or SEQ ID NO:4, ii) determining if the plant comprises a polynucleotide encoding an adult plant pathogen resistance polypeptide.

As will be apparent, preferred features and characteristics of one aspect of the invention are applicable to many other aspects of the invention.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention is hereinafter described by way of the following non-limiting Examples and with reference to the accompanying figures.

BRIEF DESCRIPTION OF THE ACCOMPANYING DRAWINGS

FIG. 1. Consensus genetic map of wheat chromosome 7D including Lr34 based on three high-resolution mapping populations defined a 0.15 cM target interval for Lr34 between XSWSNP3 and XcsLVE17. Relative positions of molecule markers are shown together with the observed recombinational distances in cM.

Figure 2:
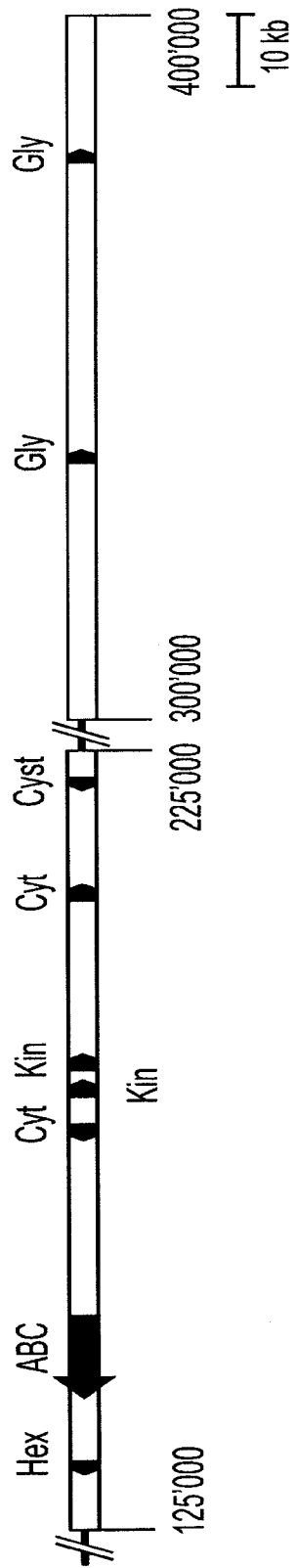

FIG. 2. Schematic of expanded view of part of wheat chromosome 7DS between XSWSNP3 and XcsLVE17 showing relative positions of open reading frames. The corresponding physical target interval sequenced on the +Lr34 cultivar 'Chinese Spring' contained ten candidate genes, nine of which are represented in the Figure by arrows. Numbers refer to the respective nucleotide positions within the 420 kb sequenced interval. Abbreviations: Gly, glycosyl transferase; Cyst, cysteine proteinase; Cyt, Cytochrome P450; LecK, lectin kinase; ABC, ABC transporter; Hex, hexose carrier.

Figure 3:
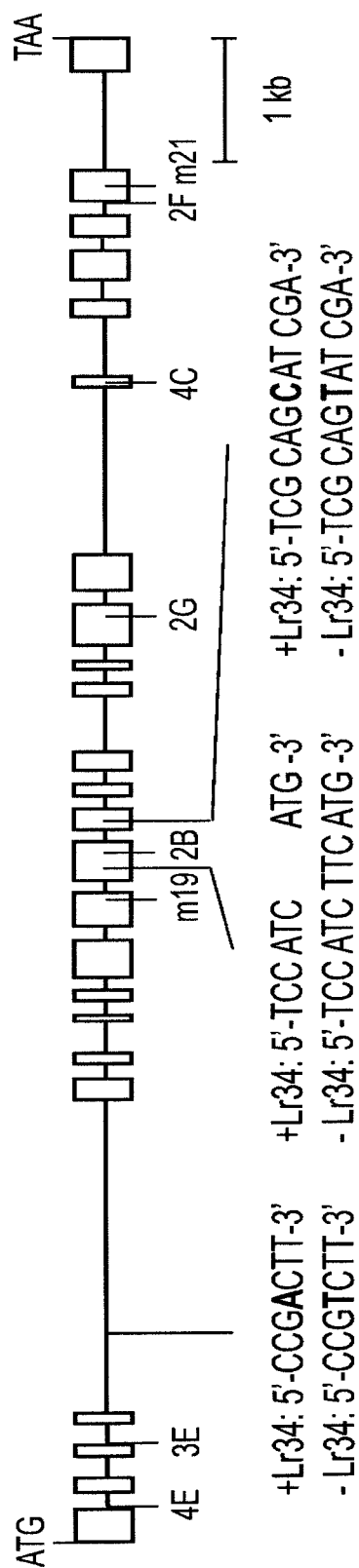

FIG. 3. Gene structure of Lr34. Open boxes indicate exons, while introns are shown as adjoining lines. Marks indicate the positions of mutation sites of the mutants labelled 2B, 2F, 2G, 3E, 4C, 4D, m19 and m21. The three sequence differences between susceptible and resistant alleles of Lr34 are indicated: +Lr34 resistant allele from Chinese Spring, −Lr34 susceptible allele from Renan.

FIG. 4. Lr34 protein sequence and polymorphisms between resistant and susceptible cultivars. Amino acid sequence of the Lr34 protein (susceptible allele) from cultivar 'Renan'. The two amino acids that are altered in the resistant allele are highlighted. Other boxes indicate the positions of the highly conserved motifs within the nucleotide binding domains. Motifs: "Walker A" GPPGCGKS (amino acids 168-175) (SEQ ID NO:50) and GVSGAGKT (amino acids 847-854) (SEQ ID NO:51); "ABC signature" ISGGQKKRLTTA (amino acids 307-318) (SEQ ID NO:52) and LSMEQRKRL-TIA (amino acids 954-965) (SEQ ID NO:53); "Walker B" AYFMD (amino acids 327-331) (SEQ ID NO:54) and IILMD (amino acids 974-978) (SEQ ID NO:55). Amino acid changes in the resistant allele of Lr34 in wheat cultivar Chinese Spring are deletion of amino acid 546 (Phe (F)) and substitution of amino acid 634 (tyrosine (Y)) to histidine. Underlined portions are the two transmembrane domains (amino acids 502-750 and 1152-1392).

Figure 5:
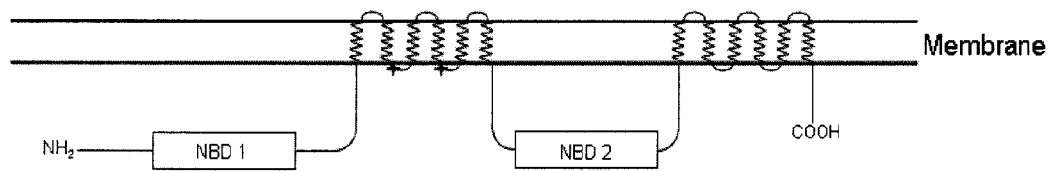

FIG. 5. Schematic representation of the Lr34 protein showing the two nucleotide binding domains (NBD) and the two transmembrane domains. The two diagnostic polymorphisms between resistant and susceptible alleles in the first transmembrane domain are indicated by stars.

Figure 6:
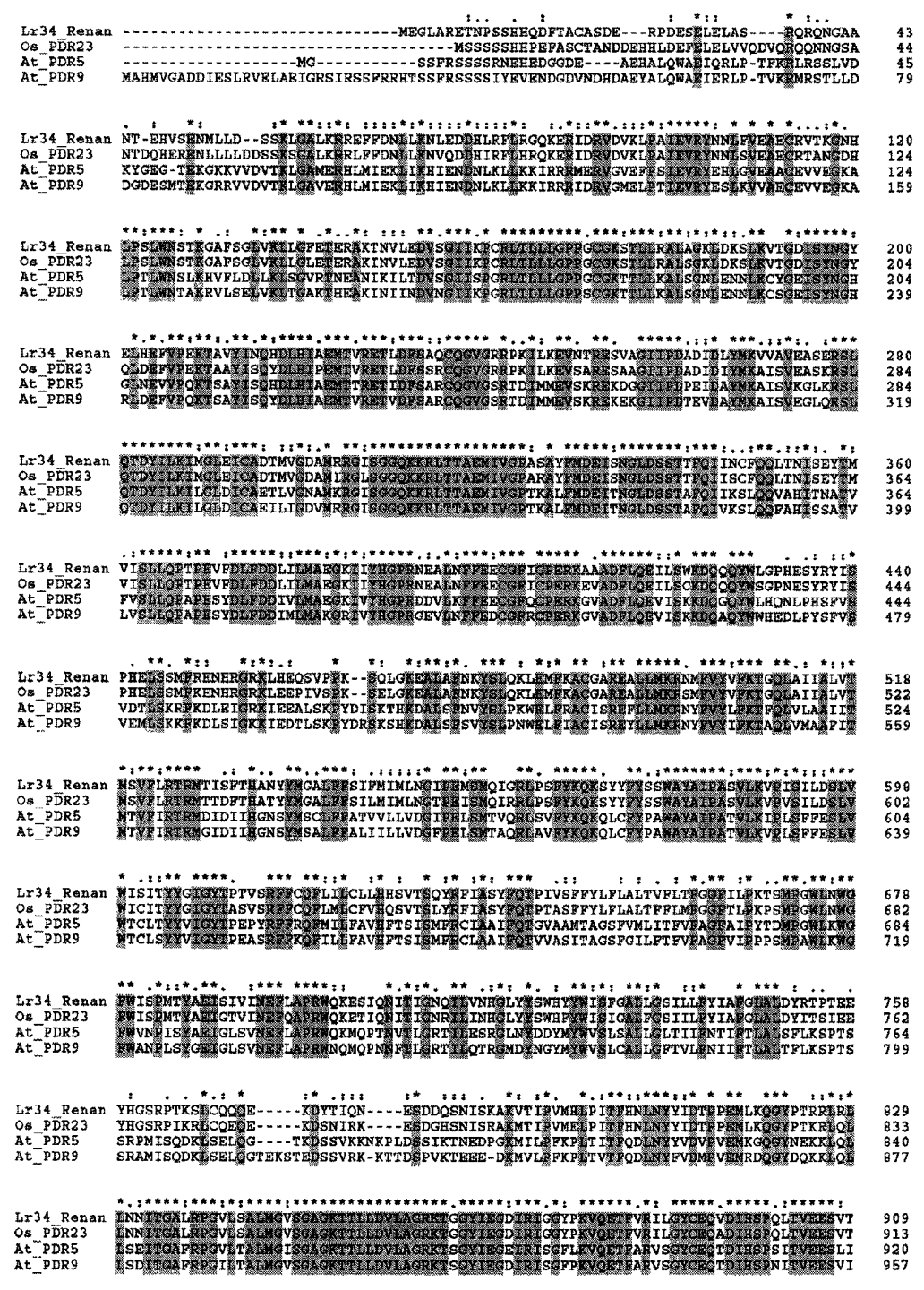

FIG. 6. Lr34 amino acid sequence alignment. Alignment of Lr34 of cultivar Renan with rice PDR23 (Os12g0512700) (SEQ ID NO:47) and *Arabidopsis* PDR5 (At3g53480) (SEQ ID NO:48) and PDR9 (At2g37280) (SEQ ID NO:49). Residues identical in all the four transporters are indicated. Rice PDR23 has been newly annotated according to the wheat Lr34 cDNA.

Figure 7:
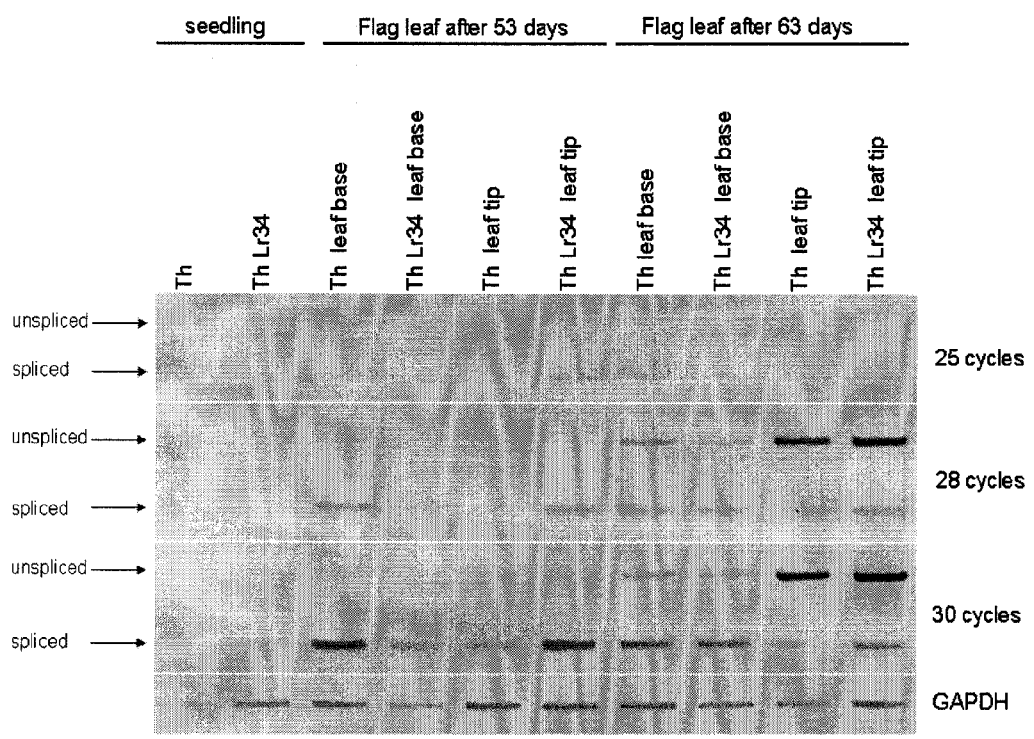

FIG. 7. Expression analysis of Lr34. Semi-quantitative RT-PCR using a probe from the 5' end of the gene. Leaves of the near isogenic lines 'Thatcher' and 'Thatcher Lr34' were harvested at the seedling stage after 14 days and of adult flag leaves on 53 and 63 days old plants. Adult leaves were halved to separately study expression levels of leaf base and leaf tip. Abbreviations: TH='Thatcher'; TH Lr34='Thatcher Lr34'; GAPDH=Glyceraldehyde 3-phosphate dehydrogenase.

Figure 8:
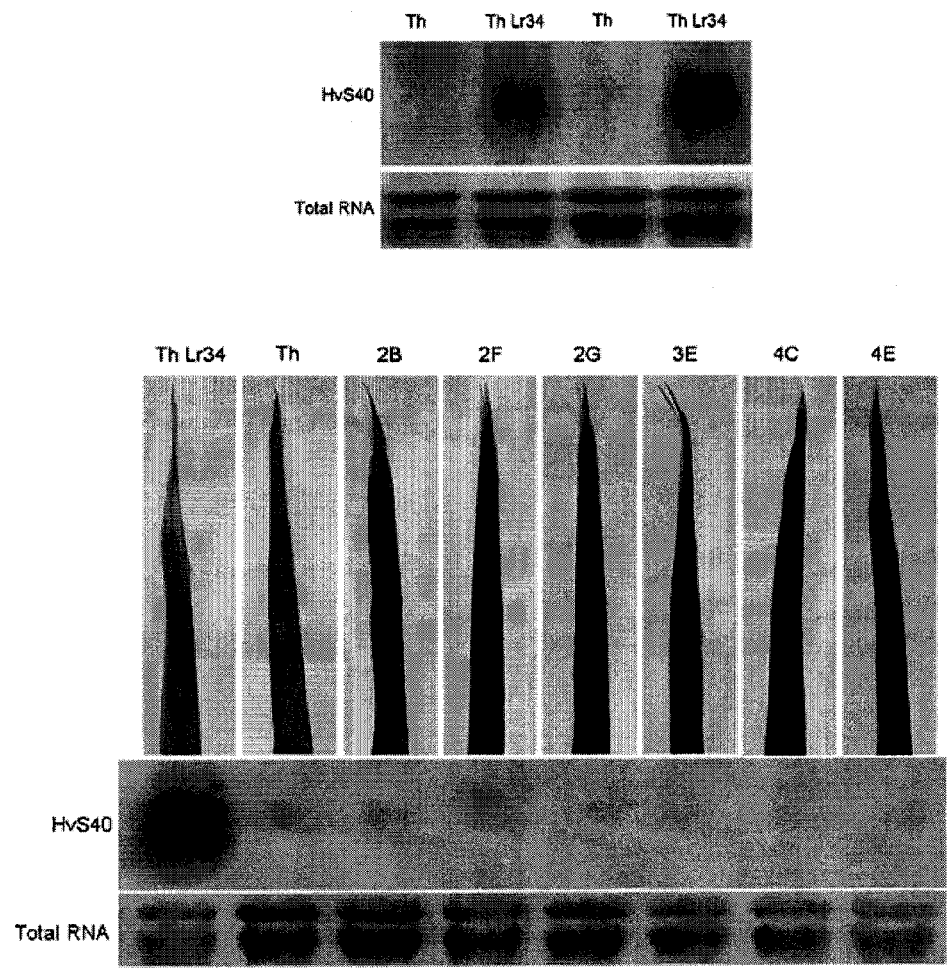

FIG. 8. Lr34 regulates senescence of flag leaves. Northern Blot using HvS40 on 63 days old flag leaves of the near isogenic lines 'Thatcher' and 'Thatcher Lr34' and the azide induced Lr34 mutants 2B, 2F, 2G, 3E, 4C and 4E. TH='Thatcher'; TH Lr34=' Thatcher Lr34'.

KEY TO THE SEQUENCE LISTING

SEQ ID NO:1—Amino acid sequence of Lr34 protein (resistant allele) from *Triticum aestivum* cv Chinese spring.
SEQ ID NO:2—Nucleotide coding sequence for Lr34 from *Triticum aestivum* cv Chinese spring.
SEQ ID NO:3—Nucleotide sequence of the Lr34 gene (genomic sequence) from *Triticum aestivum* cv Chinese spring. 24 exons are present which encode the Lr34 protein:
exon 1 starts at nucleotide 3042 and ends at nucleotide 3316;
exon 2 starts at nucleotide 3416 and ends at nucleotide 3539;
exon 3 starts at nucleotide 3693 and ends at nucleotide 3778;
exon 4 starts at nucleotide 3934 and ends at nucleotide 4018;
exon 5 starts at nucleotide 6527 and ends at nucleotide 6686;
exon 6 starts at nucleotide 6784 and ends at nucleotide 6860;
exon 7 starts at nucleotide 7119 and ends at nucleotide 7172;
exon 8 starts at nucleotide 7271 and ends at nucleotide 7361;
exon 9 starts at nucleotide 7439 and ends at nucleotide 7740;
exon 10 starts at nucleotide 7833 and ends at nucleotide 8108;
exon 11 starts at nucleotide 8187 and ends at nucleotide 8497;
exon 12 starts at nucleotide 8583 and ends at nucleotide 8743;
exon 13 starts at nucleotide 8825 and ends at nucleotide 8928;
exon 14 starts at nucleotide 9015 and ends at nucleotide 9168;
exon 15 starts at nucleotide 9606 and ends at nucleotide 9513;
exon 16 starts at nucleotide 9808 and ends at nucleotide 9581;
exon 17 starts at nucleotide 9985 and ends at nucleotide 10317;
exon 18 starts at nucleotide 10427 and ends at nucleotide 10717;
exon 19 starts at nucleotide 12159 and ends at nucleotide 12242;
exon 20 starts at nucleotide 12711 and ends at nucleotide 12844;
exon 21 starts at nucleotide 12995 and ends at nucleotide 13222;
exon 22 starts at nucleotide 13318 and ends at nucleotide 13489;
exon 23 starts at nucleotide 13569 and ends at nucleotide 13823; and
exon 24 starts at nucleotide 14613 and ends at nucleotide 14939.
SEQ ID NO:4—Amino acid sequence of Lr34 protein (susceptible allele) from *Triticum aestivum* "Renan".
SEQ ID NO:5—Nucleotide coding sequence for Lr34 (susceptible allele) from *Triticum aestivum* "Renan".
SEQ ID NO:6—Genomic DNA for *Aegilops tauschii* Lr34 equivalent. Coding region starts at nucleotide 2426 and ends at nucleotide 14212.
SEQ ID NO:7—EST of *Triticum aestivum* Lr34 (GenBank Accession No. CJ669561).
SEQ ID NO:8—EST of *Triticum aestivum* Lr34 (GenBank Accession No. DR733734).
SEQ ID NO:9—EST of *Triticum aestivum* Lr34 (GenBank Accession No. CJ562397).
SEQ ID NO:10—EST of *Triticum aestivum* Lr34 (GenBank Accession No. CV773074).
SEQ ID NO:11—EST for *Hordeum vulgare* Lr34 (GenBank Accession No. BU991506).
SEQ ID NO's: 12-46—Oligonucleotide primers.
SEQ ID NO:47—Rice ABC transporter PDR23.
SEQ ID NO:48—*Arabidopsis thaliana* ABC transporter PDR5.
SEQ ID NO:49—*Arabidopsis thaliana* ABC transporter PDR9.
SEQ ID NO: 50—N-terminal Walker A sequence of Lr34.
SEQ ID NO: 51—C-terminal Walker A sequence of Lr34.
SEQ ID NO: 52—N-terminal ABC signature sequence of Lr34.
SEQ ID NO: 53—C-terminal ABC signature sequence of Lr34.
SEQ ID NO: 54—N-terminal Walker B sequence of Lr34.
SEQ ID NO: 55—C-terminal Walker B sequence of Lr34.
SEQ ID NO: 56—Consensus Walker A sequence of ABC transporters.
SEQ ID NO: 57—Consensus Walker B sequence of ABC transporters.
SEQ ID NO: 58—Consensus ABC signature sequence of ABC transporters.
SEQ ID NO:59—PDR signature sequence 1.
SEQ ID NO:60—PDR signature sequence 2.
SEQ ID NO:61—PDR signature sequence 3.
SEQ ID NO:62—PDR signature sequence 4.
SEQ ID NO:63—Polypeptide encoded by Lr34 homeolog on wheat chromosome 7B.
SEQ ID NO:64—Open reading frame encoding Lr34 homeolog on wheat chromosome 7B.

DETAILED DESCRIPTION OF THE INVENTION

General Techniques

Unless specifically defined otherwise, all technical and scientific terms used herein shall be taken to have the same meaning as commonly understood by one of ordinary skill in the art (e.g., in cell culture, molecular genetics, plant molecular biology, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

Polypeptides/Peptides

By "substantially purified polypeptide" or "purified polypeptide" we mean a polypeptide that has generally been separated from the lipids, nucleic acids, other peptides, and other contaminating molecules with which it is associated in its native state. Preferably, the substantially purified polypeptide is at least 90% free from other components with which it is naturally associated.

The term "recombinant" in the context of a polypeptide refers to the polypeptide when produced by a cell, or in a cell-free expression system, in an altered amount or at an altered rate compared to its native state. In one embodiment, the cell is a cell that does not naturally produce the polypeptide. However, the cell may be a cell which comprises a non-endogenous gene that causes an altered amount of the polypeptide to be produced. A recombinant polypeptide of the invention includes polypeptides which have not been separated from other components of the transgenic (recombinant) cell, or cell-free expression system, in which it is produced, and polypeptides produced in such cells or cell-free systems which are subsequently purified away from at least some other components. In an embodiment, a "recombinant polypeptide" is a polypeptide made by the expression of a recombinant polynucleotide in a cell, preferably a plant cell and more preferably a cereal plant cell.

The terms "polypeptide" and "protein" are generally used interchangeably.

As used herein, the term "adult plant pathogen resistance polypeptide" refers to a protein encoded by a gene which ordinarily confers upon an adult plant an enhanced resistance to a plant pathogen when compared to an isogenic plant lacking said gene, and which confers on seedlings of the same plant substantially less or no resistance to the same pathogen when the plant is grown in normal field conditions. This term also refers to the naturally produced protein (or wild type protein from which a mutant protein is derived) encoded by a gene conferring upon an adult plant (for example, of the wheat cultivar Frontana), but not a seedling, when grown in normal field conditions, enhanced resistance to a plant pathogen. Typically, adult plant pathogen resistance polypeptides do not confer a hypersensitive response on the plants in the presence of the pathogen, and the resistance is durable in the field over time. As used herein, "adult plant" refers to a plant that has commenced the reproductive phase of growth and development. In an embodiment, less than half of the protein is produced per gram dry weight in leaves of a seedling when compared to leaves of the adult plant. Examples of plant pathogens for which resistance is enhanced include, but are not limited to, Fusarium graminearum, Erysiphe graminis f. sp. tritici, Bipolaris sorokiniana, Puccinia graminis f. sp. tritici, Puccinia striiformis and Puccinia recondite f. sp. tritici.

The % identity of a polypeptide is determined by GAP (Needleman and Wunsch, 1970) analysis (GCG program) with a gap creation penalty=5, and a gap extension penalty=0.3. The query sequence is at least 150 amino acids in length, and the GAP analysis aligns the two sequences over a region of at least 150 amino acids. More preferably, the query sequence is at least 500 amino acids in length, and the GAP analysis aligns the two sequences over a region of at least 500 amino acids. More preferably, the query sequence is at least 1,000 amino acids in length and the GAP analysis aligns the two sequences over a region of at least 1,000 amino acids. Even more preferably, the query sequence is at least 1,250 amino acids in length and the GAP analysis aligns the two sequences over a region of at least 1,250 amino acids. Even more preferably, the GAP analysis aligns two sequences over their entire length.

As used herein a "biologically active" fragment is a portion of a polypeptide of the invention which maintains a defined activity of the full-length polypeptide. Biologically active fragments can be any size as long as they maintain the defined activity but are preferably at least 1000 or at least 1200 amino acid residues long. Preferably, the biologically active fragment maintains at least 10% of the activity of the full length protein.

The phrase "enhanced resistance to a plant pathogen" is used herein as a relative term such that a plant of the invention has an increased level of resistance to a plant pathogen when compared to a genetically identical lacking the exogenous polynucleotide. Enhanced resistance can be determined by a number of methods known in the art such as analysing the plants for the amount of pathogen and/or analysing plant growth or the amount of damage to a plant in the presence of the pathogen.

As used herein, the term "has accelerated senescence of flag leaf tips" refers to an early onset of aging of the extremity of the lowermost leaf on the stem of a plant. This is used herein as a relative term such that a plant of the invention has an increased senescence of flag leaf tips when compared to a genetically identical flag leaf lacking the exogenous polynucleotide. Accelerated senescence of flag leaf tips can be measured by any means known in the art, such as that described in Example 5.

With regard to a defined polypeptide, it will be appreciated that % identity figures higher than those provided above will encompass preferred embodiments. Thus, where applicable, in light of the minimum % identity figures, it is preferred that the polypeptide comprises an amino acid sequence which is at least 60%, more preferably at least 65%, more preferably at least 70%, more preferably at least 75%, more preferably at least 76%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

As used herein, the phrase "at a position corresponding to amino acid number" or variations thereof refers to the relative position of the amino acid compared to surrounding amino acids. In this regard, in some embodiments a polypeptide of the invention may have deletional or substitutional mutations which alters the relative positioning of the amino acid when aligned against, for instance, SEQ ID NO:1 and/or SEQ ID NO:4. For example, the polypeptide with a sequence as provided in SEQ ID NO:1 has a single amino acid deletion when compared to the polypeptide with a sequence as provided in SEQ ID NO:4, namely the phenylalanine at position number 546 of SEQ ID NO:4 is missing in SEQ ID NO:1 and has not be substituted with another amino acid. As a result, the skilled person will appreciate that amino acid number 634 of SEQ ID NO:4 (Y) corresponds to amino acid number 633 of SEQ ID NO:4 (H).

Amino acid sequence mutants of the polypeptides of the present invention can be prepared by introducing appropriate nucleotide changes into a nucleic acid of the present invention, or by in vitro synthesis of the desired polypeptide. Such mutants include, for example, deletions, insertions or substitutions of residues within the amino acid sequence. A combination of deletion, insertion and substitution can be made to arrive at the final construct, provided that the final peptide product possesses the desired characteristics. Preferred amino acid sequence mutants have only one, two, three, four or less than 10 amino acid changes relative to the reference wildtype polypeptide.

Mutant (altered) peptides can be prepared using any technique known in the art. For example, a polynucleotide of the invention can be subjected to in vitro mutagenesis. Such in vitro mutagenesis techniques include sub-cloning the polynucleotide into a suitable vector, transforming the vector into a "mutator" strain such as the *E. coli* XL-1 red (Stratagene) and propagating the transformed bacteria for a suitable number of generations. In another example, the polynucleotides of the invention are subjected to DNA shuffling techniques as broadly described by Harayama (1998). Products derived from mutated/altered DNA can readily be screened using techniques described herein to determine if they possess pathogen resistance and/or ABC transporter activity.

In designing amino acid sequence mutants, the location of the mutation site and the nature of the mutation will depend on characteristic(s) to be modified. The sites for mutation can be modified individually or in series, e.g., by (1) substituting first with conservative amino acid choices and then with more radical selections depending upon the results achieved, (2) deleting the target residue, or (3) inserting other residues adjacent to the located site.

Amino acid sequence deletions generally range from about 1 to 15 residues, more preferably about 1 to 10 residues and typically about 1 to 5 contiguous residues.

Substitution mutants have at least one amino acid residue in the polypeptide molecule removed and a different residue inserted in its place. The sites of greatest interest for substitutional mutagenesis include sites identified as the active site(s). Other sites of interest are those in which particular residues obtained from various strains or species are identical. These positions may be important for biological activity. These sites, especially those falling within a sequence of at least three other identically conserved sites, are preferably substituted in a relatively conservative manner. Such conservative substitutions are shown in Table 1 under the heading of "exemplary substitutions".

In a preferred embodiment a mutant/variant polypeptide has one or two or three or four conservative amino acid changes when compared to a naturally occurring polypeptide. Details of conservative amino acid changes are provided in Table 1. In a preferred embodiment, the changes are not in one or more of the motifs which are highly conserved between the different polypeptides provided herewith. As the skilled person would be aware, such minor changes can reasonably be predicted not to alter the activity of the polypeptide when expressed in a recombinant cell.

TABLE 1

Exemplary substitutions.

| Original Residue | Exemplary Substitutions |
|---|---|
| Ala (A) | val; leu; ile; gly |
| Arg (R) | lys |
| Asn (N) | gln; his |
| Asp (D) | glu |
| Cys (C) | ser |
| Gln (Q) | asn; his |
| Glu (E) | asp |
| Gly (G) | pro, ala |
| His (H) | asn; gln |
| Ile (I) | leu; val; ala |
| Leu (L) | ile; val; met; ala; phe |

TABLE 1-continued

Exemplary substitutions.

| Original Residue | Exemplary Substitutions |
|---|---|
| Lys (K) | arg |
| Met (M) | leu; phe |
| Phe (F) | leu; val; ala |
| Pro (P) | gly |
| Ser (S) | thr |
| Thr (T) | ser |
| Trp (W) | tyr |
| Tyr (Y) | trp; phe |
| Val (V) | ile; leu; met; phe, ala |

In an embodiment, the protein of the invention is a PDR (pleiotropic drug resistance homolog) ABC transporter and comprises two nucleotide binding domains (NBD) and two transmembrane domains configured as shown in FIG. 5.

The primary amino acid sequence of Lr34 can be used to design variants/mutants thereof based on comparisons with closely related ABC transporters. As the skilled addressee will appreciate, residues highly conserved amongst closely related PDR ABC transporters are less likely to be able to be altered, especially with non-conservative substitutions, and activity maintained than less conserved residues. Such conserved regions and possible substitutions are described by Rae (2007), van den Brule and Smart (2002) and Verrier et al. (2008). The polypeptide generally comprises two Walker A boxes ($GX_4GK[ST]$) (SEQ ID NO:56) (corresponds to SEQ ID NO's: 50 and 51 of Lr34) and two Walker B boxes ((hydrophobic)$_4$[DE]) (SEQ ID NO:57) (corresponds to SEQ ID NO's: 54 and 55 of Lr34), and two ABC signature motifs ([LIVMFY]S[SGM][GE]$X_3$[RKA][LIVMYA]X[LIVFMT][AG]) (SEQ ID NO:58) (corresponds to SEQ ID NO's: 52 and 53 of Lr34), with each NBD comprising, in order from the N-terminus, a Walker A, ABC signature and Walker B motif (see, for example, FIG. 4). In the above sequences X may be any amino acid, and may be independently the same or different.

Furthermore, the polypeptide generally comprises a PDR signature 1 (LLLGPP) (SEQ ID NO:59) which is immediately N-terminal to and slightly overlaps with the N-terminal Walker A box; PDR signature 2 (GLDSST) (SEQ ID NO:60) which starts about four residues C-terminal to the N-terminal Walker B box; PDR signature 3 (GLD[AT]R[AS]AAIV[MI]R) (SEQ ID NO:61) which starts about four residues C-terminal to the C-terminal Walker B box; and PDR signature 4 (VCTIHQPS) (SEQ ID NO:62) which starts about 86 residues C-terminal to PDR signature 3.

In an embodiment, the polypeptide of the invention comprises one or more of the amino acids motifs provided as SEQ ID NO's: 56 to 58, preferably two copies of all three. More preferably, the polypeptide of the invention comprises one or more of the amino acids motifs provided as SEQ ID NO's: 50 to 55, preferably all six.

In addition, in yet a further embodiment the polypeptide of the invention comprises one or more of the amino acids motifs provided as SEQ ID NO's: 59 to 62, preferably all four.

Sources of naturally occurring variants of SEQ ID NO:1 which confer resistance as described herein are outlined in Table 5. Based on the information provided herein, the skilled person could readily determine the amino acid sequence of these naturally occurring variants, as well as polynucleotides encoding therefor.

Also included within the scope of the invention are polypeptides of the present invention which are differentially modified during or after synthesis, e.g., by biotinylation, benzylation, glycosylation, acetylation, phosphorylation, amidation, derivatization by known protecting/blocking groups, proteolytic cleavage, linkage to an antibody molecule or other cellular ligand, etc. The polypeptides may be post-translationally modified in a cell, for example by phosphorylation, which may modulate its activity. These modifications may serve to increase the stability and/or bioactivity of the polypeptide of the invention.

Polypeptides of the present invention can be produced in a variety of ways, including production and recovery of natural polypeptides, production and recovery of recombinant polypeptides, and chemical synthesis of the polypeptides. In one embodiment, an isolated polypeptide of the present invention is produced by culturing a cell capable of expressing the polypeptide under conditions effective to produce the polypeptide, and recovering the polypeptide. A preferred cell to culture is a recombinant cell of the present invention. Effective culture conditions include, but are not limited to, effective media, bioreactor, temperature, pH and oxygen conditions that permit polypeptide production. An effective medium refers to any medium in which a cell is cultured to produce a polypeptide of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art. A preferred means of producing the polypeptides is in a transgenic plant, preferably a transgenic cereal plant.

Polynucleotides and Genes

The present invention refers to various polynucleotides. As used herein, a "polynucleotide" or "nucleic acid" or "nucleic acid molecule" means a polymer of nucleotides, which may be DNA or RNA or a combination thereof, and includes mRNA, cRNA, cDNA, tRNA, siRNA, shRNA and hpRNA. It may be DNA or RNA of cellular, genomic or synthetic origin, for example made on an automated synthesizer, and may be combined with carbohydrate, lipids, protein or other materials, labelled with fluorescent or other groups, or attached to a solid support to perform a particular activity defined herein, or comprise one or more modified nucleotides not found in nature, well known to those skilled in the art. The polymer may be single-stranded, essentially double-stranded or partly double-stranded. An example of a partly-double stranded RNA molecule is a hairpin RNA (hpRNA), short hairpin RNA (shRNA) or self-complementary RNA which include a double stranded stem formed by basepairing between a nucleotide sequence and its complement and a loop sequence which covalently joins the nucleotide sequence and its complement. Basepairing as used herein refers to standard basepairing between nucleotides, including G: U basepairs. "Complementary" means two polynucleotides are capable of basepairing (hybridizing) along part of their lengths, or along the full length of one or both. A "hybridized polynucleotide" means the polynucleotide is actually basepaired to its complement. The term "polynucleotide" is used interchangeably herein with the term "nucleic acid".

By "isolated polynucleotide" we mean a polynucleotide which has generally been separated from the polynucleotide sequences with which it is associated or linked in its native state. Preferably, the isolated polynucleotide is at least 90% free from other components with which it is naturally associated.

The present invention involves modification of gene activity and the construction and use of chimeric genes. As used herein, the term "gene" includes any deoxyribonucleotide sequence which includes a protein coding region or which is transcribed in a cell but not translated, as well as associated non-coding and regulatory regions. Such associated regions are typically located adjacent to the coding region or the transcribed region on both the 5' and 3' ends for a distance of about 2 kb on either side. In this regard, the gene may include control signals such as promoters, enhancers, termination and/or polyadenylation signals that are naturally associated with a given gene, or heterologous control signals in which case the gene is referred to as a "chimeric gene". The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene.

A "Lr34 gene" as used herein refers to a nucleotide sequence which is homologous to the isolated Lr34 gene (SEQ ID NO:3) or Lr34 cDNA (SEQ ID NO:2) described herein, which encodes a protein that confers resistance to a pathogen, preferably a fungal pathogen, on a plant, preferably a cereal plant and more preferably a wheat plant. Preferably, the protein confers resistance to more than one fungal pathogen. Lr34 genes include the naturally occurring alleles or variants existing in cereals such as wheat, including those encoded by the D genomes of hexaploid wheat and its D genome diploid progenitors or relatives, as well as non-naturally occurring variants which may be produced by those skilled in the art of gene modification. Nucleic acid molecules having the nucleotide sequence shown herein as SEQ ID NO:2 (cDNA) or SEQ ID NO:3 (genomic sequence), encoding a protein with amino acid sequence SEQ ID NO:1, are examples of an Lr34 gene. In a preferred embodiment, a Lr34 gene refers to a nucleic acid molecule comprising nucleotides having a sequence having at least 90% identity to SEQ ID NO:2.

A genomic form or clone of a gene containing the transcribed region may be interrupted with non-coding sequences termed "introns" or "intervening regions" or "intervening sequences." An "intron" as used herein is a segment of a gene which is transcribed as part of a primary RNA transcript but is not present in the mature mRNA molecule. Introns are removed or "spliced out" from the nuclear or primary transcript; introns therefore are absent in the messenger RNA (mRNA). Introns may contain regulatory elements such as enhancers. "Exons" as used herein refer to the DNA regions corresponding to the RNA sequences which are present in the mature mRNA or the mature RNA molecule in cases where the RNA molecule is not translated. An mRNA functions during translation to specify the sequence or order of amino acids in a nascent polypeptide. The term "gene" includes a synthetic or fusion molecule encoding all or part of the proteins of the invention described herein and a complementary nucleotide sequence to any one of the above. A gene may be introduced into an appropriate vector for extrachromosomal maintenance in a cell or for integration into the host genome.

As used herein, a "chimeric gene" refers to any gene that is not a native gene in its native location. Typically, a chimeric gene comprises regulatory and transcribed or protein coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. The term "endogenous" is used herein to refer to a substance that is normally present or produced in an unmodified plant at the same developmental stage as the plant under investigation. An "endogenous gene" refers to a native gene in its natural location in the genome of an organism. As used herein, "recombinant nucleic acid molecule", "recombinant polynucleotide" or variations thereof refer to a nucleic acid molecule which has been constructed or modified by recombinant DNA technology. The terms "foreign polynucleotide" or "exogenous polynucleotide" or "heterologous polynucleotide" and the like refer to any nucleic acid which is introduced into the genome of a cell by experimental manipulations. For example, the present inventors have identified the Lr34 homeolog on wheat chromosome 7B (see SEQ ID NO's 63 and 64). The skilled person can use this information to mutant the Lr34 gene homeolog in durum wheat such that it encodes a protein of the invention which lacks a phenylalanine residue or any amino acid at a position corresponding to amino acid number 546 of SEQ ID NO:4, and has an amino acid other than a tyrosine residue at a position corresponding to amino acid number 634 of SEQ ID NO:4. Such a mutated gene, and the encoded mRNA, would be considered as an "exogenous" polynucleotide of the invention.

Foreign or exogenous genes may be genes that are inserted into a non-native organism, native genes introduced into a new location within the native host, or chimeric genes. A "transgene" is a gene that has been introduced into the genome by a transformation procedure. The term "genetically modified" includes introducing genes into cells by transformation or transduction, mutating genes in cells and altering or modulating the regulation of a gene in a cell or organisms to which these acts have been done or their progeny.

Furthermore, the term "exogenous" in the context of a polynucleotide (nucleic acid) refers to the polynucleotide when present in a cell, or in a cell-free expression system, in an altered amount compared to its native state. In one embodiment, the cell is a cell that does not naturally comprise the polynucleotide. However, the cell may be a cell which comprises a non-endogenous polynucleotide resulting in an altered amount of production of the encoded polypeptide. An exogenous polynucleotide of the invention includes polynucleotides which have not been separated from other components of the transgenic (recombinant) cell, or cell-free expression system, in which it is present, and polynucleotides produced in such cells or cell-free systems which are subsequently purified away from at least some other components. The exogenous polynucleotide (nucleic acid) can be a contiguous stretch of nucleotides existing in nature, or comprise two or more contiguous stretches of nucleotides from different sources (naturally occurring and/or synthetic) joined to form a single polynucleotide. Typically such chimeric polynucleotides comprise at least an open reading frame encoding a polypeptide of the invention operably linked to a promoter suitable of driving transcription of the open reading frame in a cell of interest.

The % identity of a polynucleotide is determined by GAP (Needleman and Wunsch, 1970) analysis (GCG program) with a gap creation penalty=5, and a gap extension penalty=0.3. The query sequence is at least 450 nucleotides in length, and the GAP analysis aligns the two sequences over a region of at least 450 nucleotides. Preferably, the query sequence is at least 1,500 nucleotides in length, and the GAP analysis aligns the two sequences over a region of at least 1,500 nucleotides. Even more preferably, the query sequence is at least 3,000 nucleotides in length and the GAP analysis aligns the two sequences over a region of at least 3,000 nucleotides. Even more preferably, the GAP analysis aligns two sequences over their entire length.

With regard to the defined polynucleotides, it will be appreciated that % identity figures higher than those provided above will encompass preferred embodiments. Thus, where applicable, in light of the minimum % identity figures, it is preferred that the polynucleotide comprises a polynucleotide sequence which is at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

In a preferred embodiment, the polynucleotide of the invention is not a sequence of nucleotides as provided in any one of SEQ ID NO's 7 to 11.

In a further embodiment, the present invention relates to polynucleotides which are substantially identical to those specifically described herein. As used herein, with reference to a polynucleotide the term "substantially identical" means the substitution of one or a few (for example 2, 3, or 4) nucleotides whilst maintaining at least one activity of the native protein encoded by the polynucleotide. In addition, this term includes the addition or deletion of nucleotides which results in the increase or decrease in size of the encoded native protein by one or a few (for example 2, 3, or 4) amino acids whilst maintaining at least one activity of the native protein encoded by the polynucleotide.

The present invention refers to use of oligonucleotides. As used herein, "oligonucleotides" are polynucleotides up to 50 nucleotides in length. The minimum size of such oligonucleotides is the size required for the formation of a stable hybrid between an oligonucleotide and a complementary sequence on a nucleic acid molecule of the present invention. They can be RNA, DNA, or combinations or derivatives of either. Oligonucleotides are typically relatively short single stranded molecules of 10 to 30 nucleotides, commonly 15-25 nucleotides in length. When used as a probe or as a primer in an amplification reaction, the minimum size of such an oligonucleotide is the size required for the formation of a stable hybrid between the oligonucleotide and a complementary sequence on a target nucleic acid molecule. Preferably, the oligonucleotides are at least 15 nucleotides, more preferably at least 18 nucleotides, more preferably at least 19 nucleotides, more preferably at least 20 nucleotides, even more preferably at least 25 nucleotides in length. Oligonucleotides of the present invention used as a probe are typically conjugated with a label such as a radioisotope, an enzyme, biotin, a fluorescent molecule or a chemiluminescent molecule.

The present invention includes oligonucleotides that can be used as, for example, probes to identify nucleic acid molecules, or primers to produce nucleic acid molecules. Probes and/or primers can be used to clone homologues of the polynucleotides of the invention from other species. Furthermore, hybridization techniques known in the art can also be used to screen genomic or cDNA libraries for such homologues.

Polynucleotides and oligonucleotides of the present invention include those which hybridize under stringent conditions to a sequence provided as SEQ ID NO's: 2 and/or 3. As used herein, stringent conditions are those that (1) employ low ionic strength and high temperature for washing, for example, 0.015 M NaCl/0.0015 M sodium citrate/0.1% NaDodSO$_4$ at 50° C.; (2) employ during hybridisation a denaturing agent such as formamide, for example, 50% (vol/vol) formamide with 0.1% bovine serum albumin, 0.1% Ficoll, 0.1% polyvinylpyrrolidone, 50 mM sodium phosphate buffer at pH 6.5 with 750 mM NaCl, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 g/ml), 0.1% SDS and 10% dextran sulfate at 42° C. in 0.2×SSC and 0.1% SDS.

Polynucleotides of the present invention may possess, when compared to naturally occurring molecules, one or more mutations which are deletions, insertions, or substitutions of nucleotide residues. Mutants can be either naturally occurring (that is to say, isolated from a natural source) or synthetic (for example, by performing site-directed mutagenesis on the nucleic acid). A variant of a polynucleotide or an oligonucleotide of the invention includes molecules of varying sizes of, and/or are capable of hybridising to, the wheat genome close to that of the reference polynucleotide or oligonucleotide molecules defined herein. For example, variants may comprise additional nucleotides (such as 1, 2, 3, 4, or more), or less nucleotides as long as they still hybridise to the target region. Furthermore, a few nucleotides may be substituted without influencing the ability of the oligonucleotide to hybridise to the target region. In addition, variants may readily be designed which hybridise close to, for example to within 50 nucleotides, the region of the plant genome where the specific oligonucleotides defined herein hybridise. In particular, this includes polynucleotides which encode the same polypeptide or amino acid sequence but which vary in nucleotide sequence by redundancy of the genetic code. The terms "polynucleotide variant" and "variant" also include naturally occurring allelic variants.

Nucleic Acid Constructs

The present invention includes nucleic acid constructs comprising the polynucleotides of the invention, and vectors and host cells containing these, methods of their production and use, and uses thereof. The present invention refers to elements which are operably connected or linked. "Operably connected" or "operably linked" and the like refer to a linkage of polynucleotide elements in a functional relationship. Typically, operably connected nucleic acid sequences are contiguously linked and, where necessary to join two protein coding regions, contiguous and in reading frame. A coding sequence is "operably connected to" another coding sequence when RNA polymerase will transcribe the two coding sequences into a single RNA, which if translated is then translated into a single polypeptide having amino acids derived from both coding sequences. The coding sequences need not be contiguous to one another so long as the expressed sequences are ultimately processed to produce the desired protein.

As used herein, the term "cis-acting sequence", "cis-acting element" or "cis-regulatory region" or "regulatory region" or similar term shall be taken to mean any sequence of nucleotides, which when positioned appropriately and connected relative to an expressible genetic sequence, is capable of regulating, at least in part, the expression of the genetic sequence. Those skilled in the art will be aware that a cis-regulatory region may be capable of activating, silencing, enhancing, repressing or otherwise altering the level of expression and/or cell-type-specificity and/or developmental specificity of a gene sequence at the transcriptional or post-transcriptional level. In preferred embodiments of the present invention, the cis-acting sequence is an activator sequence that enhances or stimulates the expression of an expressible genetic sequence.

"Operably connecting" a promoter or enhancer element to a transcribable polynucleotide means placing the transcribable polynucleotide (e.g., protein-encoding polynucleotide or other transcript) under the regulatory control of a promoter, which then controls the transcription of that polynucleotide. In the construction of heterologous promoter/structural gene combinations, it is generally preferred to position a promoter or variant thereof at a distance from the transcription start site of the transcribable polynucleotide which is approximately the same as the distance between that promoter and the protein coding region it controls in its natural setting; i.e., the gene from which the promoter is derived. As is known in the art, some variation in this distance can be accommodated without loss of function. Similarly, the preferred positioning of a regulatory sequence element (e.g., an operator, enhancer etc) with respect to a transcribable polynucleotide to be placed under its control is defined by the positioning of the element in its natural setting; i.e., the genes from which it is derived.

"Promoter" or "promoter sequence" as used herein refers to a region of a gene, generally upstream (5') of the RNA encoding region, which controls the initiation and level of transcription in the cell of interest. A "promoter" includes the transcriptional regulatory sequences of a classical genomic gene, such as a TATA box and CCAAT box sequences, as well as additional regulatory elements (i.e., upstream activating sequences, enhancers and silencers) that alter gene expression in response to developmental and/or environmental stimuli, or in a tissue-specific or cell-type-specific manner. A promoter is usually, but not necessarily (for example, some PolIII promoters), positioned upstream of a structural gene, the expression of which it regulates. Furthermore, the regulatory elements comprising a promoter are usually positioned within 2 kb of the start site of transcription of the gene. Promoters may contain additional specific regulatory elements, located more distal to the start site to further enhance expression in a cell, and/or to alter the timing or inducibility of expression of a structural gene to which it is operably connected.

"Constitutive promoter" refers to a promoter that directs expression of an operably linked transcribed sequence in many or all tissues of an organism such as a plant. The term constitutive as used herein does not necessarily indicate that a gene is expressed at the same level in all cell types, but that the gene is expressed in a wide range of cell types, although some variation in level is often detectable. "Selective expression" as used herein refers to expression almost exclusively in specific organs of, for example, the plant, such as, for example, endosperm, embryo, leaves, fruit, tubers or root. In a preferred embodiment, a promoter is expressed selectively or preferentially in leaves and/or stems of a plant, preferably a cereal plant. Selective expression may therefore be contrasted with constitutive expression, which refers to expression in many or all tissues of a plant under most or all of the conditions experienced by the plant.

Selective expression may also result in compartmentation of the products of gene expression in specific plant tissues, organs or developmental stages. Compartmentation in specific subcellular locations such as the plastid, cytosol, vacuole, or apoplastic space may be achieved by the inclusion in the structure of the gene product of appropriate signals, eg. a signal peptide, for transport to the required cellular compartment, or in the case of the semi-autonomous organelles (plastids and mitochondria) by integration of the transgene with appropriate regulatory sequences directly into the organelle genome.

A "tissue-specific promoter" or "organ-specific promoter" is a promoter that is preferentially expressed in one tissue or organ relative to many other tissues or organs, preferably most if not all other tissues or organs in, for example, a plant. Typically, the promoter is expressed at a level 10-fold higher in the specific tissue or organ than in other tissues or organs.

The promoters contemplated by the present invention may be native to the host plant to be transformed or may be derived from an alternative source, where the region is functional in the host plant. Other sources include the *Agrobacterium* T-DNA genes, such as the promoters of genes for the biosynthesis of nopaline, octapine, mannopine, or other opine promoters, tissue specific promoters (see, e.g., U.S. Pat. No. 5,459,252 and WO 91/13992); promoters from viruses (including host specific viruses), or partially or wholly synthetic promoters. Numerous promoters that are functional in mono- and dicotyledonous plants are well known in the art (see, for example, Greve, 1983; Salomon et al., 1984; Garfinkel et al., 1983; Barker et al., 1983); including various promoters isolated from plants and viruses such as the cauliflower mosaic virus promoter (CaMV 35S, 19S). Non-limiting methods for assessing promoter activity are disclosed by Medberry et al. (1992, 1993), Sambrook et al. (1989, supra) and U.S. Pat. No. 5,164,316.

Alternatively or additionally, the promoter may be an inducible promoter or a developmentally regulated promoter which is capable of driving expression of the introduced polynucleotide at an appropriate developmental stage of the, for example, plant. Other cis-acting sequences which may be employed include transcriptional and/or translational enhancers. Enhancer regions are well known to persons skilled in the art, and can include an ATG translational initiation codon and adjacent sequences. When included, the initiation codon should be in phase with the reading frame of the coding sequence relating to the foreign or exogenous polynucleotide to ensure translation of the entire sequence if it is to be translated. Translational initiation regions may be provided from the source of the transcriptional initiation region, or from a foreign or exogenous polynucleotide. The sequence can also be derived from the source of the promoter selected to drive transcription, and can be specifically modified so as to increase translation of the mRNA.

In an embodiment, the promoter is at least capable of expressing the polypeptide in leaves of the plant, particularly adult leaves. Examples of leaf-specific promoters which can be used include those described in Yamamoto et al. (1994 and 1997), Kwon et al. (1994), Gotor et al. (1993), Orozco et al. (1993), Matsuoka et al. (1993) and Stockhaus et al. (1987 and 1989).

The nucleic acid construct of the present invention may comprise a 3' non-translated sequence from about 50 to 1,000 nucleotide base pairs which may include a transcription termination sequence. A 3' non-translated sequence may contain a transcription termination signal which may or may not include a polyadenylation signal and any other regulatory signals capable of effecting mRNA processing. A polyadenylation signal functions for addition of polyadenylic acid tracts to the 3' end of a mRNA precursor. Polyadenylation signals are commonly recognized by the presence of homology to the canonical form 5' AATAAA-3' although variations are not uncommon. Transcription termination sequences which do not include a polyadenylation signal include terminators for PolI or PolIII RNA polymerase which comprise a run of four or more thymidines. Examples of suitable 3' non-translated sequences are the 3' transcribed non-translated regions containing a polyadenylation signal from an octopine synthase (ocs) gene or nopaline synthase (nos) gene of *Agrobacterium tumefaciens* (Bevan et al., 1983). Suitable 3' non-translated sequences may also be derived from plant genes such as the ribulose-1,5-bisphosphate carboxylase (ssRUBISCO) gene, although other 3' elements known to those of skill in the art can also be employed.

As the DNA sequence inserted between the transcription initiation site and the start of the coding sequence, i.e., the untranslated 5' leader sequence (5'UTR), can influence gene expression if it is translated as well as transcribed, one can also employ a particular leader sequence. Suitable leader sequences include those that comprise sequences selected to direct optimum expression of the foreign or endogenous DNA sequence. For example, such leader sequences include a preferred consensus sequence which can increase or maintain mRNA stability and prevent inappropriate initiation of translation as for example described by Joshi (1987).

Vectors

The present invention includes use of vectors for manipulation or transfer of genetic constructs. By "chimeric vector" is meant a nucleic acid molecule, preferably a DNA molecule derived, for example, from a plasmid, bacteriophage, or plant virus, into which a nucleic acid sequence may be inserted or cloned. A vector preferably is double-stranded DNA and contains one or more unique restriction sites and may be capable of autonomous replication in a defined host cell including a target cell or tissue or a progenitor cell or tissue thereof, or capable of integration into the genome of the defined host such that the cloned sequence is reproducible. Accordingly, the vector may be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector may contain any means for assuring self-replication. Alternatively, the vector may be one which, when introduced into a cell, is integrated into the genome of the recipient cell and replicated together with the chromosome(s) into which it has been integrated. A vector system may comprise a single vector or plasmid, two or more vectors or plasmids, which together contain the total DNA to be introduced into the genome of the host cell, or a transposon. The choice of the vector will typically depend on the compatibility of the vector with the cell into which the vector is to be introduced. The vector may also include a selection marker such as an antibiotic resistance gene, a herbicide resistance gene or other gene that can be used for selection of suitable transformants. Examples of such genes are well known to those of skill in the art.

The nucleic acid construct of the invention can be introduced into a vector, such as a plasmid. Plasmid vectors typically include additional nucleic acid sequences that provide for easy selection, amplification, and transformation of the expression cassette in prokaryotic and eukaryotic cells, e.g., pUC-derived vectors, pSK-derived vectors, pGEM-derived vectors, pSP-derived vectors, pBS-derived vectors, or binary vectors containing one or more T-DNA regions. Additional nucleic acid sequences include origins of replication to provide for autonomous replication of the vector, selectable marker genes, preferably encoding antibiotic or herbicide resistance, unique multiple cloning sites providing for multiple sites to insert nucleic acid sequences or genes encoded in the nucleic acid construct, and sequences that enhance transformation of prokaryotic and eukaryotic (especially plant) cells.

By "marker gene" is meant a gene that imparts a distinct phenotype to cells expressing the marker gene and thus allows such transformed cells to be distinguished from cells that do not have the marker. A selectable marker gene confers a trait for which one can "select" based on resistance to a selective agent (e.g., a herbicide, antibiotic, radiation, heat, or other treatment damaging to untransformed cells). A screenable marker gene (or reporter gene) confers a trait that one can identify through observation or testing, i.e., by "screening" (e.g., β-glucuronidase, luciferase, GFP or other enzyme activity not present in untransformed cells). The marker gene and the nucleotide sequence of interest do not have to be linked.

To facilitate identification of transformants, the nucleic acid construct desirably comprises a selectable or screenable marker gene as, or in addition to, the foreign or exogenous polynucleotide. The actual choice of a marker is not crucial as long as it is functional (i.e., selective) in combination with the plant cells of choice. The marker gene and the foreign or exogenous polynucleotide of interest do not have to be linked, since co-transformation of unlinked genes as, for example, described in U.S. Pat. No. 4,399,216 is also an efficient process in plant transformation.

Examples of bacterial selectable markers are markers that confer antibiotic resistance such as ampicillin, erythromycin, chloramphenicol or tetracycline resistance, preferably kanamycin resistance. Exemplary selectable markers for selection of plant transformants include, but are not limited to, a hyg gene which encodes hygromycin B resistance; a neomycin phosphotransferase (nptII) gene conferring resistance to kanamycin, paromomycin, G418; a glutathione-S-transferase gene from rat liver conferring resistance to glutathione derived herbicides as, for example, described in EP 256223; a glutamine synthetase gene conferring, upon overexpression, resistance to glutamine synthetase inhibitors such as phosphinothricin as, for example, described in WO 87/05327, an acetyltransferase gene from Streptomyces viridochromogenes conferring resistance to the selective agent phosphinothricin as, for example, described in EP 275957, a gene encoding a 5-enolshikimate-3-phosphate synthase (EPSPS) conferring tolerance to N-phosphonomethylglycine as, for example, described by Hinchee et al. (1988), a bar gene conferring resistance against bialaphos as, for example, described in WO91/02071; a nitrilase gene such as bxn from Klebsiella ozaenae which confers resistance to bromoxynil (Stalker et al., 1988); a dihydrofolate reductase (DHFR) gene conferring resistance to methotrexate (Thillet et al., 1988); a mutant acetolactate synthase gene (ALS), which confers resistance to imidazolinone, sulfonylurea or other ALS-inhibiting chemicals (EP 154,204); a mutated anthranilate synthase gene that confers resistance to 5-methyl tryptophan; or a dalapon dehalogenase gene that confers resistance to the herbicide.

Preferred screenable markers include, but are not limited to, a uidA gene encoding a β-glucuronidase (GUS) enzyme for which various chromogenic substrates are known, a β-galactosidase gene encoding an enzyme for which chromogenic substrates are known, an aequorin gene (Prasher et al., 1985), which may be employed in calcium-sensitive bioluminescence detection; a green fluorescent protein gene (Niedz et al., 1995) or derivatives thereof; a luciferase (luc) gene (Ow et al., 1986), which allows for bioluminescence detection, and others known in the art. By "reporter molecule" as used in the present specification is meant a molecule that, by its chemical nature, provides an analytically identifiable signal that facilitates determination of promoter activity by reference to protein product.

Preferably, the nucleic acid construct is stably incorporated into the genome of, for example, the plant. Accordingly, the nucleic acid comprises appropriate elements which allow the molecule to be incorporated into the genome, or the construct is placed in an appropriate vector which can be incorporated into a chromosome of a plant cell.

One embodiment of the present invention includes a recombinant vector, which includes at least one polynucleotide molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid.

A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Gelvin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

The level of a protein, for example Lr34 protein, may be modulated by increasing the level of expression of a nucleotide sequence that codes for the protein in a plant cell, or decreasing the level of expression of a gene encoding the protein in the plant, leading to modified pathogen resistance. The level of expression of a gene may be modulated by altering the copy number per cell, for example by introducing a synthetic genetic construct comprising the coding sequence and a transcriptional control element that is operably connected thereto and that is functional in the cell. A plurality of transformants may be selected and screened for those with a favourable level and/or specificity of transgene expression arising from influences of endogenous sequences in the vicinity of the transgene integration site. A favourable level and pattern of transgene expression is one which results in a substantial modification of pathogen resistance or other phenotype. Alternatively, a population of mutagenized seed or a population of plants from a breeding program may be screened for individual lines with altered pathogen resistance or other phenotype associated with pathogen resistance.

Recombinant Cells

Another embodiment of the present invention includes a recombinant cell comprising a host cell transformed with one or more recombinant molecules of the present invention, or progeny cells thereof. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Preferred host cells are plant cells, more preferably cells of a cereal plant, more preferably barley or wheat cells, and even more preferably a wheat cell.

Transgenic Plants

The term "plant" as used herein as a noun refers to whole plants and refers to any member of the Kingdom Plantae, but as used as an adjective refers to any substance which is present in, obtained from, derived from, or related to a plant, such as for example, plant organs (e.g. leaves, stems, roots, flowers), single cells (e.g. pollen), seeds, plant cells and the like. Plantlets and germinated seeds from which roots and shoots have emerged are also included within the meaning of "plant". The term "plant parts" as used herein refers to one or more plant tissues or organs which are obtained from a plant and which comprises genomic DNA of the plant. Plant parts include vegetative structures (for example, leaves, stems), roots, floral organs/structures, seed (including embryo, cotyledons, and seed coat), plant tissue (for example, vascular tissue, ground tissue, and the like), cells and progeny of the same. The term "plant cell" as used herein refers to a cell obtained from a plant or in a plant and includes protoplasts or other cells derived from plants, gamete-producing cells, and cells which regenerate into whole plants. Plant cells may be cells in culture. By "plant tissue" is meant differentiated tissue in a plant or obtained from a plant ("explant") or undifferentiated tissue derived from immature or mature embryos, seeds, roots, shoots, fruits, tubers, pollen, tumor tissue, such as crown galls, and various forms of aggregations of plant cells in culture, such as calli. Exemplary plant tissues in or from seeds are cotyledon, embryo and embryo axis. The invention accordingly includes plants and plant parts and products comprising these, particularly seed comprising modified oil composition.

As used herein, the term "seed" refers to "mature seed" of a plant, which is either ready for harvesting or has been harvested from the plant, such as is typically harvested commercially in the field, or as "developing seed" which occurs in a plant after fertilization and prior to seed dormancy being established and before harvest.

A "transgenic plant" as used herein refers to a plant that contains a nucleic acid construct not found in a wild-type plant of the same species, variety or cultivar. That is, transgenic plants (transformed plants) contain genetic material (a transgene) that they did not contain prior to the transformation. The transgene may include genetic sequences obtained from or derived from a plant cell, or another plant cell, or a non-plant source, or a synthetic sequence. Typically, the transgene has been introduced into the plant by human manipulation such as, for example, by transformation but any method can be used as one of skill in the art recognizes. The genetic material is preferably stably integrated into the genome of the plant. The introduced genetic material may comprise sequences that naturally occur in the same species but in a rearranged order or in a different arrangement of elements, for example an antisense sequence. Plants containing such sequences are included herein in "transgenic plants". A "non-transgenic plant" is one which has not been genetically modified by the introduction of genetic material by recombinant DNA techniques. In a preferred embodiment, the transgenic plants are homozygous for each and every gene that has been introduced (transgene) so that their progeny do not segregate for the desired phenotype.

As used herein, the term "compared to an isogenic plant" refers to a plant which is isogenic relative to the transgenic plant but without the transgene of interest. Preferably, the corresponding non-transgenic plant is of the same cultivar or variety as the progenitor of the transgenic plant of interest, or a sibling plant line which lacks the construct, often termed a "segregant", or a plant of the same cultivar or variety transformed with an "empty vector" construct, and may be a non-transgenic plant. "Wild type", as used herein, refers to a cell, tissue or plant that has not been modified according to the invention. Wild-type cells, tissue or plants may be used as controls to compare levels of expression of an exogenous nucleic acid or the extent and nature of trait modification with cells, tissue or plants modified as described herein.

Transgenic plants, as defined in the context of the present invention include progeny of the plants which have been genetically modified using recombinant techniques, wherein the progeny comprise the transgene of interest. Such progeny may be obtained by self-fertilization of the primary transgenic plant or by crossing such plants with another plant of the same species. This would generally be to modulate the production of at least one protein defined herein in the desired plant or plant organ. Transgenic plant parts include all parts and cells of said plants comprising the transgene such as, for example, cultured tissues, callus and protoplasts.

Plants contemplated for use in the practice of the present invention include both monocotyledons and dicotyledons. Target plants include, but are not limited to, the following: cereals (for example, wheat, barley, rye, oats, rice, maize, sorghum and related crops); beet (sugar beet and fodder beet); pomes, stone fruit and soft fruit (apples, pears, plums, peaches, almonds, cherries, strawberries, raspberries and black-berries); leguminous plants (beans, lentils, peas, soybeans); oil plants (rape or other Brassicas, mustard, poppy, olives, sunflowers, safflower, flax, coconut, castor oil plants, cocoa beans, groundnuts); cucumber plants (marrows, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocados, cinnamon, camphor); or plants such as maize, tobacco, nuts, coffee, sugar cane, tea, vines, hops, turf, bananas and natural rubber plants, as well as ornamentals (flowers, shrubs, broad-leaved trees and evergreens, such as conifers). Preferably, the plant is a cereal plant, more preferably wheat, rice, maize, triticale, oats or barley, even more preferably wheat.

As used herein, the term "wheat" refers to any species of the Genus *Triticum*, including progenitors thereof, as well as progeny thereof produced by crosses with other species. Wheat includes "hexaploid wheat" which has genome organization of AABBDD, comprised of 42 chromosomes, and "tetraploid wheat" which has genome organization of AABB, comprised of 28 chromosomes. Hexaploid wheat includes *T. aestivum, T. spelta, T. macha, T. compactum, T. sphaerococcum, T. vavilovii,* and interspecies cross thereof. A preferred species of hexaploid wheat is *T. aestivum* ssp *aestivum* (also termed "breadwheat"). Tetraploid wheat includes *T. durum* (also referred to herein as durum wheat or *Triticum turgidum* ssp. *durum*), *T. dicoccoides, T. dicoccum, T. polonicum,* and interspecies cross thereof. In addition, the term "wheat" includes potential progenitors of hexaploid or tetraploid *Triticum* sp. such as *T. uartu, T. monococcum* or *T. boeoticum* for the A genome, *Aegilops speltoides* for the B genome, and *T. tauschii* (also known as *Aegilops squamosa* or *Aegilops tauschii*) for the D genome. Particularly preferred progenitors are those of the A genome, even more preferably the A genome progenitor is *T. monococcum*. A wheat cultivar for use in the present invention may belong to, but is not limited to, any of the above-listed species. Also encompassed are plants that are produced by conventional techniques using *Triticum* sp. as a parent in a sexual cross with a non-*Triticum* species (such as rye [*Secale cereale*]), including but not limited to *Triticale*.

As used herein, the term "barley" refers to any species of the Genus *Hordeum*, including progenitors thereof, as well as progeny thereof produced by crosses with other species. It is preferred that the plant is of a *Hordeum* species which is commercially cultivated such as, for example, a strain or cultivar or variety of *Hordeum vulgare* or suitable for commercial production of grain.

Transgenic plants, as defined in the context of the present invention include plants (as well as parts and cells of said plants) and their progeny which have been genetically modified using recombinant techniques to cause production of at least one polypeptide of the present invention in the desired plant or plant organ. Transgenic plants can be produced using techniques known in the art, such as those generally described in A. Slater et al., Plant Biotechnology—The Genetic Manipulation of Plants, Oxford University Press (2003), and P. Christou and H. Klee, Handbook of Plant Biotechnology, John Wiley and Sons (2004).

In a preferred embodiment, the transgenic plants are homozygous for each and every gene that has been introduced (transgene) so that their progeny do not segregate for the desired phenotype. The transgenic plants may also be heterozygous for the introduced transgene(s), such as, for example, in F1 progeny which have been grown from hybrid seed. Such plants may provide advantages such as hybrid vigour, well known in the art.

Four general methods for direct delivery of a gene into cells have been described: (1) chemical methods (Graham et al., 1973); (2) physical methods such as microinjection (Capecchi, 1980); electroporation (see, for example, WO 87/06614, U.S. Pat. Nos. 5,472,869, 5,384,253, WO 92/09696 and WO 93/21335); and the gene gun (see, for example, U.S. Pat. No. 4,945,050 and U.S. Pat. No. 5,141,131); (3) viral vectors (Clapp, 1993; Lu et al., 1993; Eglitis et al., 1988); and (4) receptor-mediated mechanisms (Curiel et al., 1992; Wagner et al., 1992).

Acceleration methods that may be used include, for example, microprojectile bombardment and the like. One example of a method for delivering transforming nucleic acid molecules to plant cells is microprojectile bombardment. This method has been reviewed by Yang et al., Particle Bombardment Technology for Gene Transfer, Oxford Press, Oxford, England (1994). Non-biological particles (microprojectiles) that may be coated with nucleic acids and delivered into cells by a propelling force. Exemplary particles include those comprised of tungsten, gold, platinum, and the like. A particular advantage of microprojectile bombardment, in addition to it being an effective means of reproducibly transforming monocots, is that neither the isolation of protoplasts, nor the susceptibility of *Agrobacterium* infection are required. A particle delivery system suitable for use with the present invention is the helium acceleration PDS-1000/He gun is available from Bio-Rad Laboratories. For the bombardment, immature embryos or derived target cells such as scutella or calli from immature embryos may be arranged on solid culture medium.

In another alternative embodiment, plastids can be stably transformed. Method disclosed for plastid transformation in higher plants include particle gun delivery of DNA containing a selectable marker and targeting of the DNA to the plastid genome through homologous recombination (U.S. Pat. No. 5,451,513, U.S. Pat. No. 5,545,818, U.S. Pat. No. 5,877,402, U.S. Pat. No. 5,932,479, and WO 99/05265.

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art (see, for example, U.S. Pat. No. 5,177,010, U.S. Pat. No. 5,104,310, U.S. Pat. No. 5,004,863, U.S. Pat. No. 5,159,135). Further, the integration of the T-DNA is a relatively precise process resulting in few rearrangements. The region of DNA to be transferred is defined by the border sequences, and intervening DNA is usually inserted into the plant genome.

*Agrobacterium* transformation vectors are capable of replication in *E. coli* as well as *Agrobacterium*, allowing for convenient manipulations as described (Klee et al., Plant DNA Infectious Agents, Hohn and Schell, (editors), Springer-Verlag, New York, (1985): 179-203). Moreover, technological advances in vectors for *Agrobacterium*-mediated gene transfer have improved the arrangement of genes and restriction sites in the vectors to facilitate construction of vectors capable of expressing various polypeptide coding genes. The vectors described have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant varieties where *Agrobacterium*-mediated transformation is efficient, it is the method of choice because of the facile and defined nature of the gene transfer.

A transgenic plant formed using *Agrobacterium* transformation methods typically contains a single genetic locus on one chromosome. Such transgenic plants can be referred to as being hemizygous for the added gene. More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants for the gene of interest.

It is also to be understood that two different transgenic plants can also be mated to produce offspring that contain two independently segregating exogenous genes. Selfing of appropriate progeny can produce plants that are homozygous for both exogenous genes. Back-crossing to a parental plant and out-crossing with a non-transgenic plant are also contemplated, as is vegetative propagation. Descriptions of other breeding methods that are commonly used for different traits and crops can be found in Fehr, Breeding Methods for Cultivar Development, J. Wilcox (editor) American Society of Agronomy, Madison Wis. (1987).

Transformation of plant protoplasts can be achieved using methods based on calcium phosphate precipitation, polyethylene glycol treatment, electroporation, and combinations of these treatments. Application of these systems to different plant varieties depends upon the ability to regenerate that particular plant strain from protoplasts. Illustrative methods for the regeneration of cereals from protoplasts are described (Fujimura et al., 1985; Toriyama et al., 1986; Abdullah et al., 1986).

Other methods of cell transformation can also be used and include but are not limited to introduction of DNA into plants by direct DNA transfer into pollen, by direct injection of DNA into reproductive organs of a plant, or by direct injection of DNA into the cells of immature embryos followed by the rehydration of desiccated embryos.

The regeneration, development, and cultivation of plants from single plant protoplast transformants or from various transformed explants is well known in the art (Weissbach et al., Methods for Plant Molecular Biology, Academic Press, San Diego, (1988)). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired exogenous nucleic acid is cultivated using methods well known to one skilled in the art.

Methods for transforming dicots, primarily by use of *Agrobacterium tumefaciens*, and obtaining transgenic plants have been published for cotton (U.S. Pat. No. 5,004,863, U.S. Pat. No. 5,159,135, U.S. Pat. No. 5,518,908); soybean (U.S. Pat. No. 5,569,834, U.S. Pat. No. 5,416,011); *Brassica* (U.S. Pat. No. 5,463,174); peanut (Cheng et al., 1996); and pea (Grant et al., 1995).

Methods for transformation of cereal plants such as wheat and barley for introducing genetic variation into the plant by introduction of an exogenous nucleic acid and for regeneration of plants from protoplasts or immature plant embryos are well known in the art, see for example, CA 2,092,588, AU 61781/94, AU 667939, U.S. Pat. No. 6,100,447, WO 97/048814, U.S. Pat. No. 5,589,617, U.S. Pat. No. 6,541,257, and other methods are set out in WO 99/14314. Preferably, transgenic wheat or barley plants are produced by *Agrobacterium tumefaciens* mediated transformation procedures. Vectors carrying the desired nucleic acid construct may be introduced into regenerable wheat cells of tissue cultured plants or explants, or suitable plant systems such as protoplasts. The regenerable wheat cells are preferably from the scutellum of immature embryos, mature embryos, callus derived from these, or the meristematic tissue.

To confirm the presence of the transgenes in transgenic cells and plants, a polymerase chain reaction (PCR) amplification or Southern blot analysis can be performed using methods known to those skilled in the art. Expression products of the transgenes can be detected in any of a variety of ways, depending upon the nature of the product, and include Western blot and enzyme assay. One particularly useful way to quantitate protein expression and to detect replication in different plant tissues is to use a reporter gene, such as GUS. Once transgenic plants have been obtained, they may be grown to produce plant tissues or parts having the desired phenotype. The plant tissue or plant parts, may be harvested, and/or the seed collected. The seed may serve as a source for growing additional plants with tissues or parts having the desired characteristics.

Marker Assisted Selection

Marker assisted selection is a well recognised method of selecting for heterozygous plants required when backcrossing with a recurrent parent in a classical breeding program. The population of plants in each backcross generation will be heterozygous for the gene of interest normally present in a 1:1 ratio in a backcross population, and the molecular marker can be used to distinguish the two alleles of the gene. By extracting DNA from, for example, young shoots and testing with a specific marker for the introgressed desirable trait, early selection of plants for further backcrossing is made whilst energy and resources are concentrated on fewer plants. To further speed up the backcrossing program, the embryo from immature seeds (25 days post anthesis) may be excised and grown up on nutrient media under sterile conditions, rather than allowing full seed maturity. This process, termed "embryo rescue", used in combination with DNA extraction at the three leaf stage and analysis of at least one Lr34 gene or allele that confers enhanced resistance to pathogens to the plant, allows rapid selection of plants carrying the desired trait, which may be nurtured to maturity in the greenhouse or field for subsequent further backcrossing to the recurrent parent.

Any molecular biological technique known in the art can be used in the methods of the present invention. Such methods include, but are not limited to, the use of nucleic acid amplification, nucleic acid sequencing, nucleic acid hybridization with suitably labeled probes, single-strand conformational analysis (SSCA), denaturing gradient gel electrophoresis (DGGE), heteroduplex analysis (HET), chemical cleavage analysis (CCM), catalytic nucleic acid cleavage or a combination thereof (see, for example, Lemieux, 2000; Langridge et al., 2001). The invention also includes the use of molecular marker techniques to detect polymorphisms linked to alleles of (for example) Lr34 gene which confers enhanced resistance to plant pathogens. Such methods include the detection or analysis of restriction fragment length polymorphisms (RFLP), RAPD, amplified fragment length polymorphisms (AFLP) and microsatellite (simple sequence repeat, SSR) polymorphisms. The closely linked markers can be obtained readily by methods well known in the art, such as Bulked Segregant Analysis, as reviewed by Langridge et al., (2001).

The "polymerase chain reaction" ("PCR") is a reaction in which replicate copies are made of a target polynucleotide using a "pair of primers" or "set of primers" consisting of "upstream" and a "downstream" primer, and a catalyst of polymerization, such as a DNA polymerase, and typically a thermally-stable polymerase enzyme. Methods for PCR are known in the art, and are taught, for example, in "PCR" (M. J. McPherson and S. G Moller (editors), BIOS Scientific Publishers Ltd, Oxford, (2000)). PCR can be performed on cDNA obtained from reverse transcribing mRNA isolated from plant cells expressing a Lr34 gene or allele which confers enhanced resistance to plants pathogens. However, it will generally be easier if PCR is performed on genomic DNA isolated from a plant.

A primer is an oligonucleotide sequence that is capable of hybridising in a sequence specific fashion to the target sequence and being extended during the PCR. Amplicons or PCR products or PCR fragments or amplification products are extension products that comprise the primer and the newly synthesized copies of the target sequences. Multiplex PCR systems contain multiple sets of primers that result in simultaneous production of more than one amplicon. Primers may be perfectly matched to the target sequence or they may contain internal mismatched bases that can result in the introduction of restriction enzyme or catalytic nucleic acid recognition/cleavage sites in specific target sequences. Primers may also contain additional sequences and/or contain modified or labelled nucleotides to facilitate capture or detection of amplicons. Repeated cycles of heat denaturation of the DNA, annealing of primers to their complementary sequences and extension of the annealed primers with polymerase result in exponential amplification of the target sequence. The terms target or target sequence or template refer to nucleic acid sequences which are amplified.

Methods for direct sequencing of nucleotide sequences are well known to those skilled in the art and can be found for example in Ausubel et al., (supra) and Sambrook et al., (supra). Sequencing can be carried out by any suitable method, for example, dideoxy sequencing, chemical sequencing or variations thereof. Direct sequencing has the advantage of determining variation in any base pair of a particular sequence.

TILLING

Plants of the invention can be produced using the process known as TILLING (Targeting Induced Local Lesions I N Genomes). In a first step, introduced mutations such as novel single base pair changes are induced in a population of plants by treating seeds (or pollen) with a chemical mutagen, and then advancing plants to a generation where mutations will be stably inherited. DNA is extracted, and seeds are stored from all members of the population to create a resource that can be accessed repeatedly over time.

For a TILLING assay, PCR primers are designed to specifically amplify a single gene target of interest. Specificity is especially important if a target is a member of a gene family or part of a polyploid genome. Next, dye-labeled primers can be used to amplify PCR products from pooled DNA of multiple individuals. These PCR products are denatured and reannealed to allow the formation of mismatched base pairs. Mismatches, or heteroduplexes, represent both naturally occurring single nucleotide polymorphisms (SNPs) (i.e., several plants from the population are likely to carry the same polymorphism) and induced SNPs (i.e., only rare individual plants are likely to display the mutation). After heteroduplex formation, the use of an endonuclease, such as Cel I, that recognizes and cleaves mismatched DNA is the key to discovering novel SNPs within a TILLING population.

Using this approach, many thousands of plants can be screened to identify any individual with a single base change as well as small insertions or deletions (1-30 bp) in any gene or specific region of the genome. Genomic fragments being assayed can range in size anywhere from 0.3 to 1.6 kb. At 8-fold pooling, 1.4 kb fragments (discounting the ends of fragments where SNP detection is problematic due to noise) and 96 lanes per assay, this combination allows up to a million base pairs of genomic DNA to be screened per single assay, making TILLING a high-throughput technique.

TILLING is further described in Slade and Knauf (2005), and Henikoff et al. (2004).

In addition to allowing efficient detection of mutations, high-throughput TILLING technology is ideal for the detection of natural polymorphisms. Therefore, interrogating an unknown homologous DNA by heteroduplexing to a known sequence reveals the number and position of polymorphic sites. Both nucleotide changes and small insertions and deletions are identified, including at least some repeat number polymorphisms. This has been called Ecotilling (Comai et al., 2004).

Each SNP is recorded by its approximate position within a few nucleotides. Thus, each haplotype can be archived based on its mobility. Sequence data can be obtained with a relatively small incremental effort using aliquots of the same amplified DNA that is used for the mismatch-cleavage assay. The left or right sequencing primer for a single reaction is chosen by its proximity to the polymorphism. Sequencher software performs a multiple alignment and discovers the base change, which in each case confirmed the gel band.

Ecotilling can be performed more cheaply than full sequencing, the method currently used for most SNP discovery. Plates containing arrayed ecotypic DNA can be screened rather than pools of DNA from mutagenized plants. Because detection is on gels with nearly base pair resolution and background patterns are uniform across lanes, bands that are of identical size can be matched, thus discovering and genotyping SNPs in a single step. In this way, ultimate sequencing of the SNP is simple and efficient, made more so by the fact that the aliquots of the same PCR products used for screening can be subjected to DNA sequencing.

Antibodies

The term "antibody" as used in this invention includes polyclonal antibodies, monoclonal antibodies, bispecific antibodies, diabodies, triabodies, heteroconjugate antibodies, chimeric antibodies including intact molecules as well as fragments thereof, such as Fab, F(ab')2, and Fv which are capable of binding the epitopic determinant, and other antibody-like molecules.

The term "specifically binds" refers to the ability of the antibody to bind to at least one polypeptide of the present invention but not significantly to known proteins in the sample/organism to be tested.

As used herein, the term "epitope" refers to a region of a polypeptide of the invention which is bound by the antibody. An epitope can be administered to an animal to generate antibodies against the epitope, however, antibodies of the present invention preferably specifically bind the epitope region in the context of the entire polypeptide.

If polyclonal antibodies are desired, a selected mammal (e.g., mouse, rabbit, goat, horse, etc.) is immunised with an immunogenic polypeptide of the invention. Serum from the immunised animal is collected and treated according to known procedures. If serum containing polyclonal antibodies contains antibodies to other antigens, the polyclonal antibodies can be purified by immunoaffinity chromatography. Techniques for producing and processing polyclonal antisera are known in the art. In order that such antibodies may be made, the invention also provides polypeptides of the invention or fragments thereof haptenised to another polypeptide for use as immunogens in animals.

Monoclonal antibodies directed against polypeptides of the invention can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. Panels of monoclonal antibodies produced can be screened for various properties; i.e., for isotype and epitope affinity.

An alternative technique involves screening phage display libraries where, for example the phage express scFv fragments on the surface of their coat with a large variety of complementarity determining regions (CDRs). This technique is well known in the art.

Other techniques for producing antibodies of the invention are known in the art.

Antibodies of the invention may be bound to a solid support and/or packaged into kits in a suitable container along with suitable reagents, controls, instructions and the like.

In an embodiment, antibodies of the present invention are detectably labeled. Exemplary detectable labels that allow for direct measurement of antibody binding include radiolabels, fluorophores, dyes, magnetic beads, chemiluminescers, colloidal particles, and the like. Examples of labels which permit indirect measurement of binding include enzymes where the substrate may provide for a coloured or fluorescent product. Additional exemplary detectable labels include covalently bound enzymes capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. Further, exemplary detectable labels include biotin, which binds with high affinity to avidin or streptavidin; fluorochromes (e.g., phycobiliproteins, phycoerythrin and allophycocyanins; fluorescein and Texas red), which can be used with a fluorescence activated cell sorter; haptens; and the like. Preferably, the detectable label allows for direct measurement in a plate luminometer, for example, biotin. Such labeled antibodies can be used in techniques known in the art to detect polypeptides of the invention.

EXAMPLES

Example 1

Materials and Methods

Microscopic Analysis of Seedling Rust Infection

Plants were grown in a growth chamber maintained at 4-8° C. under a 12 hour light and dark regime. Seedlings were inoculated at the two leaf stage using leaf rust culture 467 and transferred into a humidity chamber (with a temperature range of 16-20° C.) for 24 hours and returned to the 4-8° C. growth chamber. For microscopic visualisation of internal infection structures, the first leaf tissue was autoclaved in 1M KOH, washed in 50 mM $KPO_4$ and stained with a 50 mM $KPO_4$ (pH 7.8) solution containing 20 ug/ml of wheat germ agglutinin (WGA) conjugated to the fluorophore alexa 488 (Invitrogen, USA) staining solution. All WGA-alexa stained tissue was examined under blue light excitation.

RNA Isolation for Semi-Quantitative PCR and Northern Blot

Total RNA was extracted from leaves using a TRIzol solution (38% Phenol, 0.8M guanidine thiocyanate, 0.4M ammonium thiocyanate, 0.1M sodium acetate pH 5 and 10% glycerol). First-strand cDNA for RT-PCR was synthesized using Superscript II reverse transcriptase (Invitrogen). A specific fragment for semi-quantitative RT-PCR of the 5' end of the PDR was amplified using the primers Lr34_RT_fl: 5'-catcaagatttcaccgcctgtgc-3' (SEQ ID NO:12) and Lr34_RT_rl: 5'-gaagcctagcaacttcacgaggc-3' (SEQ ID NO:13) at an annealing temperature of 70° C.

For the Northern blot hybridization analysis, 15 μg of total RNA per sample was blotted on a membrane (Hybond-XL, Amersham Biosiences). The probe HvS40 (Spielmeyer et al., 2002) was $^{32}$P-labeled at 65° C. using the NEBlot® kit (New England BioLabs). Membranes were washed with a 0.5× SSC, 0.1% SDS solution at 65° C. and exposed to hypersensitive X-ray films (BioMax MS film, Kodak).

Rapid Amplification of cDNA Ends (RACE)

To determine the exact start of the cDNA, a 5' RACE approach was used. Poly A$^+$ RNA was purified from 300 μg of total RNA using the Oligotex® mRNA Mini Kit (Qiagen). Reverse transcription was done using the SMART™ RACE cDNA Amplification Kit (Clonetech Laboratories), where an adapter was ligated to the 5' end of the cDNA. Amplification of the 5' end was done using an adapter specific primer and the gene specific primer ABC_5RACE_r2: 5'-gcggggcccacaatcatctcggc-3' (SEQ ID NO:14).

Example 2

Genetic Mapping of Lr34

Plant Materials

Three backcross populations were produced and used for genetic mapping of Lr34. The parental parents for the backcrossing, scored phenotypes, population size, and markers mapped on each population are summarized in Table 2.

TABLE 2

The three backcross populations that have been used for the high-resolution genetic mapping of Lr34.

| +Lr34 parent | −Lr34 parent | +Lr34 backcross line | origin | phenotypic scoring | nr. of plants | markers mapped |
|---|---|---|---|---|---|---|
| Forno | Arina | Arina Lr34 (Arina*3/Forno) | Swiss winter wheat | Leaf tip necrosis, leaf rust infection | 1728 | BE493812, SWSNP1, SWSNP2, SWSNP3, SWDEL1, SWDEL2, SWDEL3, SWM10, csLVMS |
| PI58548 | Thatcher | RL6058 (Thatcher*6/PI58548) | Chinese landrace | Leaf, stripe, and stem rust; powdery mildew | 1152 | Gwm1220, BJ280740, csLVD13, csLVD2, csLVMS, BF473324, csLV34 |
| Parula | Avocet | Avocet Lr34 (Avocet*5/Parula) | CIMMYT | Leaf and stripe rust, leaf tip necrosis | 1152 | Gwm1220, csLVD13, csLVD2, csLVE17, csLVMS, csLV34 |

The 'Arina×Formo' fine-mapping population was developed by crossing the highly resistant Swiss winter wheat cultivar 'Formo' with the susceptible Swiss winter wheat cultivar 'Arina'. Subsequent backcrossing to Arina and several generations produced by self-fertilization resulted in 103 plants that were "backcross two F4" (BC2F4) containing Lr34 and on average 12.5% of the 'Formo' genome in an otherwise Arina genetic background. These plants were analyzed for the presence of the Lr34 chromosomal segment from 'Formo' using two flanking RFLP markers BE493812 and BF473324. One of these plants containing the Lr34 region was again crossed to 'Arina' and the progeny selfed to produce 1728 BC3F2 plants, having on average 6.25% of the 'Formo' genome. Recombinants were selected using the two flanking markers BE493812 and SWM10. Phenotyping of the 'Arina×Formo' population was done at Agroscope Reckenholz, Zurich, Switzerland during 2006 (BC3F3) and 2007

(BC3F4). Infection rows containing a mixture of susceptible varieties were inoculated with urediniospores of the Swiss leaf rust isolates Nr. 90035, 91047, 93003, 93012, 94015, 95001, 95012, 95028, 95037, 95039, 95219, 95251, 96002, 96004, 96209, and 96257. Disease rating was done on two replicas.

The Thatcher×RL6058 (Thatcher Lr34) and Avocet×Avocet Lr34 high resolution mapping family, disease evaluation in Australia and at CIMMYT, Mexico were as described in Lagudah et al. (2006) and Spielmeyer et al. (2002). Other genetic stocks used in this work were the near isogenic lines 'Thatcher', 'Thatcher Lr34' (=RL6058, Thatcher*6/PI5848), 'Arina', 'Arina Lr34' (Arina*3/Formo).

Marker Development for Genetic Mapping

New molecular markers for mapping were generated by exploiting the syntenic information of rice, the model grass *Brachypodium sylvaticum* and the diploid D-genome progenitor *Aegilops tauschii* as described by Bossolini et al. (2006).

To gain physical information of the Lr34 target interval, a partially fingerprinted Bacterial Artificial Chromosome (BAC) library of *Aegilops tauschii* (J. Dvorak, U C Davis) was screened using wheat ESTs related to genes from the syntenic region of rice and *Brachypodium sylvaticum*. Thirteen BAC clones from three different contigs (HI057C6/HD036L7/HD102K14/HI056G21/HD062G18/HI031F14/HI135B2/RI004I15/RI042I4/HI148C23/BB045B13/HB067N4/BB062G18) were sequenced by low-pass sequencing using an ABI® 3730 sequencer (Applied Biosystems). Sequences were assembled using PHRAP and mined for simple sequence repeats (SSR). SSRs were amplified by designing primers in the flanking regions (Table 3).

PCR products were analyzed using the LiCOR® DNA Sequencer 4200. Polymorphic SSRs were identified and designated with prefixes "SWM" or "cs". Sequence tagged sites were developed by designing primers on low-copy sequences. Locus-specific probes were sequenced and mined for single nucleotide polymorphisms (SNP) and insertion/deletions (InDel). Polymorphic SNP-based makers and InDels were designated as Swiss Wheat SNP (SWSNP) and Swiss Wheat Deletion (SWDEL), respectively. Primer sequences for the PCR based markers mapped on the populations are summarized in Table 3. Additional low copy probes, csLVD2, csLVD13, csLVE17, for RFLP analysis were isolated from shotgun plasmid libraries from the *Ae tauschii* BAC contigs by screening with total genomic DNA from *Ae tauschii*. Recombinant plasmids where no DNA hybridization signals were detected after an overnight exposure were selected as potential low copy probes.

Using these genetic markers and the mapping populations for Lr34, the high-resolution mapping revealed a 0.15 cM target interval for Lr34 flanked by genetic markers XSWSNP3 and XcsLVE17 (FIG. 1). Several markers (FIG. 1) were cosegregating with Lr34.

Example 3

Mutagenesis and Isolation of Lr34 Mutants

Seeds of the Lr34 isoline, 'Lalbahadur Lr34' were irradiated using a $^{60}$Co source at a dosage of 20 krad and the subsequent M1-M5 generations evaluated at CIMMYT, Mexico and in Australia as reported in Spielmeyer et al. (2002). Eight mutants were identified from the gamma-irradiated population. These were analysed using some of the new genetic markers (Example 2). Of the eight mutants, six were interstitial deletions spanning the Lr34/Yr18/Pm38/Ltn1 locus while the two mutants designated m19 and m21 showed no loss of markers in the aforementioned genetic locus. Mutants m19 and m21 were therefore subjected to further analysis utilising the newly identified markers and cosegregating genes.

Sodium azide mutants were developed using seed from a single head of an RL6058 plant grown in the glasshouse to multiply pure seed stocks for mutagenesis. Seeds were pre-soaked for 12 hrs at 4° C. before treating the grains in an oxygenated solution of 7 mM sodium azide at pH 3.0 for 2 hrs. The grains were rinsed and planted in the field. The M2 progenies were planted as single ear rows and scored for stripe, leaf and stem rust infection in the field in the presence of the pathogens.

TABLE 3

Primer sequences of molecular markers used in this study.

| marker name | primer forward | primer reverse | marker type | Tm [° C.] |
|---|---|---|---|---|
| SWSNP1 | 5'-catctttcgtatacatga gaaac-3' (SEQ ID NO: 15) | 5'-gtgtcgattcatgtgag atgc-3' (SEQ ID NO: 16) | SNP c -> t | 60 |
| SWSNP2 | 5'-cattatgttagcagct tagcg-3' (SEQ ID NO: 17) | 5'-ccaaccatcattttggag catg-3' (SEQ ID NO: 18) | SNP c -> t | 60 |
| SWSNP3 | 5'-gta gat cgt gtc gtg ttc aac-3' (SEQ ID NO: 19) | 5'-ctg cta atc cta agt aac gct c-3' (SEQ ID NO: 20) | SNP t -> a | 65 |
| SWDEL1 | 5'-cgt gag caa gac atg ggc g-3' (SEQ ID NO: 21) | 5'-gct aca gct ctg aaa cta cac-3' (SEQ ID NO: 22) | 6 bp InDel | 66.2 |
| SWDEL2 | 5'gat ttg cac gtt gat gaa acc ag-3' (SEQ ID NO: 23) | 5'-cag aat gaa gtt taa cct ggc ctg-3' (SEQ ID NO: 24) | 1 bp InDel | 60 |
| SWDEL3 | 5'- ggc tgg cta cta cga cga cg-3' (SEQ ID NO: 25) | 5'-atg gtc ttt ttt cct tca gcc-3' (SEQ ID NO: 26) | 180 bp InDel | 65 |

TABLE 3-continued

Primer sequences of molecular markers used in this study.

| marker name | primer forward | primer reverse | marker type | Tm [° C.] |
|---|---|---|---|---|
| SWM10 | 5'-gcc tac ttt gac ggc ata tgg-3' (SEQ ID NO: 27) | 5'-cca tct tga cat act ttg gcc ttc c-3' (SEQ ID NO: 28) | SSR (ca)25 | 60 |
| csLVMS | 5'-ctc cct ccc gtg agt ata ttc-3' (SEQ ID NO: 29) | 5'-atc aaa atc cca ttg cct gac-3' (SEQ ID NO: 30) | SSR (at)6tt(at)6 | 62 |
| csLV34 | 5'-gtt ggt taa gac tgg tga tgg-3' (SEQ ID NO: 31) | 5'-tgc ttg cta ttg ctg aat agt-3' (SEQ ID NO: 32) | STS | 60 |
| SWSNP1_f | 5'-cat ctt tcg tat aca tga gaa ac-3' (SEQ ID NO: 33) | 5'-gtg tcg att cat gtg aga tgc-3' (SEQ ID NO: 34) | SNP c -> t | 60 |
| SWSNP2_f | 5'-cat tat gtt agc agc tta gcg-3' (SEQ ID NO: 35) | 5'-cca acc atc att tg gag cat g-3' (SEQ ID NO: 36) | SNP c -> t | 60 |
| SWSNP3_f | 5'-gta gat cgt gtc gtg ttc aac-3' (SEQ ID NO: 37) | 5'-ctg cta atc cta agt aac gct c-3' (SEQ ID NO: 38) | SNP t -> a | 65 |
| SWDEL1_f | 5'-cgt gag caa gac atg ggc g-3' (SEQ ID NO: 39) | 5'-gct aca gct ctg aaa cta cac-3' (SEQ ID NO: 40) | 6 bp InDel | 66.2 |
| SWDEL2_f | 5'gat ttg cac gtt gat gaa acc ag-3' (SEQ ID NO: 41) | 5'-cag aat gaa gtt taa cct ggc ctg-3' (SEQ ID NO: 42) | 1 bp InDel | 60 |
| SWDEL3_f | 5'- ggc tgg cta cta cga cga cg-3' (SEQ ID NO: 43) | 5'-atg gtc ttt ttt cct tca gcc-3' (SEQ ID NO: 44) | 180 bp InDel | 65 |
| SWM10f | 5'-gcc tac ttt gac ggc ata tgg-3' (SEQ ID NO: 45) | 5'-cca tct tga cat act ttg gcc ttc c-3' (SEQ ID NO: 46) | SSR (ca)25 | 60 |

Six susceptible mutants were isolated and rated 70MS to 90MS for stripe rust, 50MS to 80MS for leaf rust and 50MS for stem rust under field conditions. Two mutants 4C (glycine to glutamic acid at amino acid position 1030 of SEQ ID NO:1) and 2G (glycine to aspartic acid at amino acid position 889 of SEQ ID NO:1) were the result of single nucleotide transitions that resulted in a single amino acid change within the second predicted nucleotide binding domain (FIGS. 3 and 5). These mutants showed only partial loss of resistance to leaf rust when examined microscopically (Example 1). Mutant 2B incorporated a single nucleotide transition in exon 11 (FIG. 3) that resulted in an early stop codon. Three mutants 3E, 4E and 2F were the result of single nucleotide transitions at splice junctions resulting in mis-spliced transcripts. The retention of introns in mutants 3E and 4E introduced early stop codons near the 5' end which was predicted to result in a non-functional protein. At the microscopic level mutants 3E and 4E were fully susceptible to leaf rust and indistinguishable from the susceptible near-isogenic line 'Thatcher'. The transcript of mutant 2F lost the second last exon (FIG. 3) which was predicted to delete 85 amino acids from the second transmembrane domain. The 2F mutant was more susceptible to leaf rust than the susceptible control 'Thatcher' during the early infection process.

The lack of resistance resulting from loss of a functional Lr34 protein observed in the mutation study is consistent with analysis of the Lr34 gene from Jagger. Jagger has Lr34-associated alleles of the csLV34 marker but is susceptible to leaf rust and stripe rust. Sequencing of the Lr34 gene in Jagger identified a G/T point mutation that resulted in a premature stop codon. Consequently, the predicted protein of cultivar Jagger lacks 185 amino acids of the C-terminus and this allele is most likely not functional. This point mutation probably occurred in a resistant cultivar that carried the +Lr34 allele.

Example 4

Physical Information of the Target Interval and Identification of the Lr34 Gene

Two BAC libraries of the +Lr34 (resistant) cultivar 'Chinese Spring' and the −Lr34 (susceptible) cultivar 'Renan' (INRA, Toulouse, France) were screened using PCR probes covering the target interval between the two flanking markers SWSNP3 and csLVE17. The 420 kb physical interval containing both flanking markers was fully sequenced in the resistant hexaploid wheat cultivar 'Chinese Spring'. To do this, four 'Chinese Spring' BAC clones, namely 345C22, 93N17, 1964C18 and 413N16, and the 'Renan' clone 656106 were selected and fully sequenced at the Genome Sequencing Center, St. Louis, Mo., USA.

Sequence analysis revealed the presence of a gene-rich island containing ten open reading frames (FIG. 2) encoding proteins with homologies to two glycosyl transferases, two cysteine proteinases, two receptor lectin kinases, two cytochrome P450 proteins, a hexose carrier and an ATP binding cassette (ABC) transporter. None of these genes was present in the syntenic region in *Brachypodium sylvaticum* and only the hexose carrier was found to be conserved in the homologous region on rice chromosome 6 (rice gene Os06g0141000). Significantly and surprisingly, none of the genes appeared to be typical LRR-NBS type genes of the class commonly associated with pathogen resistance in plants. Therefore, none of the coding regions was an obvious candidate for encoding Lr34.

To determine whether one of these candidate genes corresponded to Lr34, locus-specific PCR-amplified regions corresponding to the ten candidate genes on each of the eight Lr34 mutants were sequenced. Candidate genes were amplified by developing locus-specific PCR probes, amplified from resistant and susceptible cultivars as well as on the eight Lr34 mutants, and sequenced. The mutants were the six azide mutants in the genetic background of 'Thatcher Lr34' and two gamma irradiation mutants in the 'Lalbahadur Lr34' background (Example 3).

All of the mutant lines showed a sequence alteration in the open reading frame encoding the ABC transporter (FIG. 3). The three azide mutants 2F, 3E and 4E all had a G to A transition at an intron-exon boundary leading to splice site mutations (FIG. 7, showing retained introns). Transitions in the two azide induced mutants 2G and 4C resulted in amino acid substitutions and line 2B carried a premature stop codon in exon 11. The two gamma irradiation mutants m19 and m21 each showed a 1 bp deletion in exon 10 and 23, respectively, leading to frame shifts and premature stop codons (FIG. 3).

To remove the possibility of additional mutation sites in the other cosegregating genes, DNA fragments covering 12.7 kb of the other nine candidate genes and intergenic regions on the four azide mutants 2B, 3E, 4C and 4E were sequenced, without finding any additional sequence alterations. Similarly, sequencing showed that the gamma-radiation generated mutants m19 and m21 did not harbour any sequence changes in the coding regions of the remaining nine candidate genes. Therefore, the possibility that the eight mutations found in the ABC transporter were due to a very high mutation frequency in these lines could be excluded, and we concluded that the ABC transporter was responsible for conferring the durable Lr34 disease resistance.

Lr34 co-segregated with partial resistance to adult plant stripe rust (Yr18), powdery mildew (Pm38) as well as leaf tip necrosis (Ltn1). All of the mutants were more susceptible, as adult plants, to stripe rust and powdery mildew attributed to the loss of Yr18 and Pm38 and also exhibited complete or partial loss of Ltn1. These observations represented an important finding, in that eight independent mutations within a single ABC transporter gene encoding the Lr34 resistance also accounted for Yr18/Pm38/Ltn1, and demonstrated that a single gene conferred resistance to multiple pathogens.

The protein coding sequence of Lr34 spanned 11.7 kb in the wheat genome. Sequencing of the entire cDNA and comparison of the nucleotide sequence with the genomic sequence (SEQ ID NO:3) revealed that Lr34 had 24 exons. The gene contained 23 introns including a large intron of 2.5 kb between exons 4 and 5 (FIG. 3). The protein encoded by Lr34 from the resistant cultivar Chinese Spring had 1401 amino acids (SEQ ID NO:1), while the protein from the susceptible cultivar Renan had 1402 amino acids (SEQ ID NO:4, FIG. 4). Comparison of the amino acid sequence with other ABC transporters showed that the Lr34 proteins belonged to the Pleiotropic Drug Resistance (PDR) subfamily of ABC transporters. PDRs share a common basic structure containing two distinct domains: a cytosolic nucleotide binding domain (NBD) that contains the conserved motifs "Walker A" and "Walker B" involved in ATP binding and hydrolysis, and a hydrophobic transmembrane domain (TMD) involved in translocating the substrate. Both domains are present in duplicate, therefore the structure of PDRs is designated [NBD-TMD]$_2$ (FIG. 5).

The PDR family is only found in fungi and plants. Fifteen PDR-like genes have been identified in the genome of *Arabidopsis* and 23 members were described in rice (Crouzet et al., 2006). It is known that PDRs confer resistance to various drugs, but little is known about the substrate specificity of this protein class (Rogers et al., 2001). It has previously been reported that PEN3/PDR8, a PDR from *Arabidopsis*, contributes to nonhost resistance to pathogens (Stein et al., 2006). The closest Lr34 homolog in rice is PDR23, showing 88% identity on the amino acid level (Table 4). In *Arabidopsis*, Lr34 shows closest homology to the two transporters PDR5 and PDR9, with 56% identity. The alignment of these amino acid sequences is shown in FIG. 6.

TABLE 4

Percentage amino acid identity of wheat Lr34 to homologs of Lr34 from other plant species.

| SPECIES | GenBank Accession No. | % Identity |
| --- | --- | --- |
| Rice | EAZ20654 | 78 |
|  | EAY83289 | 76 |
|  | CAD59575 | 55 |
| Tobacco | CAH39853 (NtPDR3) | 56 |
| Grape | CAN65735 | 56 |
| Arabidopsis | NP_181265 (PDR5) | 56 |
|  | NP_190916 (PDR9) | 55 |
|  | DAA00881 (PDR13) | 54 |
|  | DAA00869 (PDR2) | 52 |
|  | NP_176196 (PDR8/PEN3) | 50 |

The present inventors next determined the sequence differences between the Lr34 alleles in cultivars with or without Lr34-based resistance. Comparison of genomic sequences of the PDR in the +Lr34 cultivar 'Chinese Spring' and the −Lr34 French winter wheat cultivar 'Renan' revealed that the gene was present in both wheat varieties. There were only three polymorphisms in the coding sequences between these two lines (FIG. 3). One SNP was located in the large intron 4. The other two sequence alterations were located in exons 11 and 12. A deletion of three base pairs 'TTC' found in exon 11 in 'Chinese Spring' results in the deletion of a phenylalanine residue whereas a second SNP in exon 12 converted a tyrosine to a histidine in the resistant cultivar. Both sequence differences located in exons affect the first transmembrane domain connecting the two nucleotide binding domains and they may alter the structure and binding specificity of the transporter (FIG. 4). Sequence comparison of 2 kb of the putative promoter regions did not reveal any differences between the resistant and susceptible alleles.

To find out which of these three sequence differences were required for determining the resistance, their diagnostic value was determined on a set of +/−Lr34 genotypes sourced from different Lr34 breeding lineages (Table 5). All the +Lr34 lines showed the same haplotype as 'Chinese Spring' and all the −Lr34 lines were identical to that of 'Renan'. Hence, all of the three reported sequence differences may be important for determining the resistance conferred by Lr34, although we have no evidence that the SNP in intron 4 affects the splice efficiency of either of the alleles. Given that the same haplotype was found in the Lr34 PDR-ABC transporter gene for the spring wheats from the South/North American breeding programs, winter wheats from Europe and the oriental Lr34 genotypes (Table 5), we infer that a single event likely accounts for the origin of Lr34 in a wheat landrace. Evidence linking the American and European wheats containing Lr34 is traced back to the founder sib cultivars, 'Mentana' and 'Ardito' developed at the beginning of the last century (Kolmer et al., 2008).

When testing the diagnostic potential of the SNP located in intron 4 a third allele was identified. The winter wheat cultivars Zinal, Allalin and Galaxie, as well as the spelt (*Triticum spelta*) varieties Ostro and Rouquin showed the +Lr34 haplotype in intron 4, but had the −Lr34 haplotype for the two markers in exons 11 and 12. Hence, these lines form a third haplotype. Interestingly, the reciprocal allele (T, for SNP in intron 4 and +Lr34 for both exon markers) was never observed. This finding suggests that this haplotype arose through mutation rather than recombination and probably represents the progenitor of the functional +Lr34 haplotype.

TABLE 5

Polymorphisms in Lr34 alleles of wheat genotypes.

| Genotype | Origin | +/− Lr34 | A/T SNP | TTC/DEL | C/T SNP |
| --- | --- | --- | --- | --- | --- |
| Chinese Spring | China | + | A | DEL | C |
| RL6058* | China | + | A | DEL | C |
| Fukuho | Japan | + | A | DEL | C |
| Mentana | Italy | + |   | DEL | C |
| Frontana | Brazil | + | A | DEL | C |
| Frontierra | Brazil | − | T | TTC | T |
| Ardito | Italy | + | A | DEL | C |
| JupatecoR | CIMMYT | + | A | DEL | C |
| JupatecoS | CIMMYT | − | T | TTC | T |
| Glenlea | Canada | + | A | DEL | C |
| Thatcher | Canada | − | T | TTC | T |
| Anza | USA | + | A | DEL | C |
| Chris | USA | + | A | DEL | C |
| Condor | Australia | + | A | DEL | C |
| Penjamo 62 | CIMMYT | + |   |   |   |
| Inia66 | CIMMYT | − |   |   |   |
| LalbahadurLr34 | CIMMYT | + | A | DEL | C |
| Lalbahadur | India | − | T | TTC | T |
| Forno | Switzerland | + |   |   |   |
| Arina | Switzerland | − |   |   |   |
| Pegaso | Italy | + | A | DEL | C |
| Bezostaja | Russia | + | A | DEL | C |
| Kavkaz | Russia | + | A | DEL | C |
| Roazon | France | − |   |   |   |
| Capelle Desprez | UK | − | T | TTC | T |
| Maris Huntsman | UK | − | T | TTC | T |
| Renan | France | − | T | TTC | T |
| "Synthetic"_taus |   | − | T | TTC | T |
| AL8/78_taus | Armenia | − | T | TTC | T |
| AUS18913_taus | Iran | − | T | TTC | T |

Example 5

Expression of Lr34

Lr34 is a model for adult plant resistance, which is not effective at the seedling stage under normal field conditions. To determine whether this was related to lower expression of Lr34 at the seedling stage, semi-quantitative RT-PCR was used to measure expression levels at various stages of plant development using the near isogenic lines 'Thatcher' and 'Thatcher Lr34'. The PDR was expressed at very low levels in 14 days old seedlings grown at 20° C. whereas the expression level was significantly higher in flag leaves of adult plants after 53 and 63 days (FIG. 7). There was no substantial difference in expression between resistant and susceptible plants which was in agreement with the finding that there were no sequence differences in the promoter regions of the resistant and susceptible alleles. Interestingly, the unspliced product was observed to accumulate in adult plants after 63 days. Also, an altered transcript in 'ThatcherLr34' had 92 nucleotides missing from exon 10 which was predicted to disrupt the reading frame and result in a truncated protein.

It has been shown that Lr34 confers resistance at the seedling stage to leaf rust cultures at low temperatures (Dyck and Samborski, 1982). Analysis of the mutants and the parental Lr34 lines grown, as seedlings, at low temperatures (4-8° C.) and infected with leaf rust revealed a "slow rusting" resistance response with the intact Lr34 gene. In the initial 2-3 weeks post infection, differences in colonized mesophyl cells between mutants m19, m21 and lalbahadur Lr34' were insignificant. However by the fifth week the colonized area had extended at least four times in size with mutants m19 and m21 when compared with the active Lr34 gene. External symptoms of sporulation in seedlings were evident in the mutants by the fifth week whereas the presence of the active Lr34 gene delayed visible symptoms until after the sixth week post infection. This observation was akin to the longer latency period that was characteristic of the slow rusting mechanism of Lr34 resistance.

Lr34 conferred a broad spectrum resistance against several obligate biotrophic pathogens including fungi from the Ascomycetes and Basidiomycetes. Rubiales and Nicks (1995) reported that Lr34 was associated with reduced intercellular hyphal growth but not with a hypersensitive response or papilla formation. The eight Lr34 mutants were affected in their resistance against leaf rust, stripe rust and powdery mildew and they did not show leaf tip necrosis as described above. Infection experiments revealed that the level of resistance was coupled to the development of leaf tip necrosis and that artificial inoculation with leaf rust before emergence of leaf tip necrosis led to more severe disease symptoms than infections at later time points. These observations suggested that the resistance mechanism of Lr34 was due to a general physiological effect rather than to a 'classical' resistance mechanisms involving recognition of pathogen elicitors or secretion of antifungal components.

From this, a hypothesis was formed that the durable resistance conferred by Lr34 was associated with and at least partly due to premature senescence of the flag leaf, in particular the leaf tips. In contrast to necrosis, senescence is a highly controlled process including the remobilization of nutrients and the degradation of chlorophyll. It was considered that premature leaf senescence starting from the leaf tip could hamper the feeding of the pathogen from host cells and might retard its growth and multiplication. Senescence-related genes were therefore analysed in the wheat plants with or without Lr34.

The gene HvS40 was known to be highly upregulated during senescence in barley (Krupinska et al., 2007). A probe corresponding to this gene was prepared from cDNA. Using this probe in a Northern blot hybridization analysis revealed that wheat HvS40 was highly expressed in flag leaf tips of 'Thatcher Lr34' but not of 'Thatcher' in 63 days old plants. Furthermore the gene was down-regulated or not expressed in the six Lr34 azide mutants (FIG. 8). This was strong evidence that Lr34 regulated senescence of flag leaves in adult wheat plants. On the other hand, microscopic observations have indicated the build up of cell wall appositions following leaf rust infection of Lr34 genotypes. It is therefore likely that Lr34 mediated resistance affected pathogen development in a more complex way.

The cloning of Lr34 is the first reported cloning of a multi-pathogen resistance QTL from wheat, which includes Lr34, Yr18, Pm38, Ltn1 and demonstrated this was controlled by a single gene. An ABC transporter of the PDR subfamily was identified as the gene being responsible for conferring this durable adult plant resistance. Resistant and susceptible alleles differed by only three minor sequence alterations within the coding sequence. The resistant allele was thought to accelerate senescence of flag leaf tips and therefore compromise nutrient uptake by obligate biotrophic pathogens.

Example 6

Related Genes from Wheat and Other Species

The homoeologous genes from the A and B genomes of wheat, and genes encoding homologs in other species were isolated by using probes derived from the wheat Lr34 gene to probe cDNA or genomic libraries. The homoeologous genes from the A and B genomes were isolated. A homologous gene was isolated from *Aegilops tauschii*, a diploid cereal (D genome) related to wheat (SEQ ID NO:6). Other related sequences were identified from EST databases, containing partial sequences (Table 6).

TABLE 6

ESTs which are homologous to Lr34. The percentage sequence identity over the matching region is shown.

| EST's | Identity | Region of SEQ ID NO: 2 corresponding to the EST |
|---|---|---|
| Wheat | | |
| CJ669561 | 99% | 1496-2333 |
| DR733734 | 96% | 3089-3802 |
| CJ562397 | 99% | 3561-4206 |
| CV773074 | 100% | 3732-4206 |
| Rice | | |
| AK102367 | 91% | 569-2775 |
| AK103110 | 91% | 569-2775 |
| CB630740 | 91% | 1280-2085 |
| CI097424 | 92% | 2292-2775 |
| CI380443 | 93% | 2425-2775 |
| CI361087 | 93% | 2432-2775 |
| CI522302 | 90% | 1904-2252 |
| Barley | | |
| BU991506 | 71% | 2518-2991 |
| Sugarcane | | |
| CA075859 | 77% | 3216-3883 |
| CA267101 | 77% | 3407-3995 |

A related gene member was also detected in barley when a cDNA probe derived from the 3' half of the gene was hybridised to genomic barley DNA under standard conditions.

The present inventors have also determined the homeolog of Lr34 present on chromosome 7B of wheat. The protein sequence of this homeolog is provided as SEQ ID NO:63 and the cDNA sequence as SEQ ID NO:64.

Example 7

Production of Transgenic Wheat Expressing an Exogenous Adult Plant Pathogen Resistance Gene In order to produce transgenic wheat, the polynucleotide comprising a sequence of nucleotides as provided in SEQ ID NO:2 is sub-cloned into a pPlex vector (Schunmann et al., 2003) such that the subterranean clover stunt virus promoter is able to drive gene transcription in a wheat cell.

Transformation of wheat embryos from the cultivar Bobwhite 26 is performed according to the method of Pellegrineschi et al. (2002). To confirm that the plants that were produced contained the construct, PCR analysis is performed on genomic DNA extracted from leaves using a FastDNA® kit (BIO 101 Inc., Vista, Calif., USA) according to the suppliers instructions. The DNA is eluted into 100 µl sterile deionized water and 1 µl used in PCR.

Plants are tested for enhanced resistance to plant pathogens such as *Puccinia graminis f. sp. tritici* (which causes stem rust), *Puccinia striiformis* (which causes stripe rust) and/or *Puccinia recondite f. sp. tritici* (which causes leaf rust).

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The present application claims priority from AU 2008904364 filed 25 Aug. 2008, the entire contents of which are incorporated herein by reference.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Abdullah et al. (1986) Biotechnology 4:1087.
Barker et al. (1983) Plant Mol. Biol. 2: 235-350.
Bevan et al. (1983) Nucl. Acid Res. 11: 369-385.
Bossolini et al. (2006) Theor. Appl. Genet. 113:1049-1062.
Brueggeman et al. (2002) Proc. Natl. Acad. Sci. USA 99:9328-9333.
Capecchi (1980) Cell 22:479-488
Cheng et al. (1996) Plant Cell Rep. 15:653-657.
Clapp (1993) Clin. Perinatol. 20:155-168.
Cloutier et al. (2007) Plant Mol. Biol. 65:93-106.
Collins et al. (1999) Plant Cell 11:1365-1376.
Comai et al. (2004) Plant J 37: 778-786.
Crouzet et al. (2006) FEBS Letters 580: 1123-1130.
Curiel et al. (1992) Hum. Gen. Ther. 3:147-154.
Dyck (1977) Can. J. Genet. Cytol. 19:711-716.
Dyck et al. (1987) Genome 29:467-469.
Dyck and Samborski (1982) Can. J. Genet. Cytol. 24: 273-283.
Dyck et al. (1966) Can. J. Genet. Cytol. 8: 665-671.
Eglitis et al. (1988) Biotechniques 6:608-614.
Feuillet et al. (2003) Proc. Natl. Acad. Sci. 100:15253-15258.
Fujimura et al. (1985) Plant Tissue Cultural Letters 2:74.
Garfinkel et al. (1983) Cell 27: 143-153.
German and Kolmer (1992) Theor. Appl. Genet. 84: 97-105.
Gotor et al. (1993) Plant J. 3:509-518.
Graham et al. (1973) Virology 54:536-539.
Grant et al. (1995) Plant Cell Rep. 15:254-258.
Greve (1983) J. Mol. Appl. Genet. 1: 499-511.
Harayama (1998) Trends Biotechnol. 16:76-82.
Henikoff et al. (2004) Plant Physiol 135: 630-636.

Hinchee et al. (1988) Biotech. 6:915.
Huang et al. (2003) Genetics 164:655-664.
Joshi et al. (2004) Crop Science 44:792-796.
Joshi (1987) Nucl. Acid Res. 15: 6643-6653.
Kolmer et al. (2003) Plant Disease 87: 859-866.
Kolmer et al. (2008) Crop Science 48:1037-1047.
Krupinska et al. (2002) Plant Physiol. 130: 1172-1180.
Kwon et al. (1994) Plant Physiol. 105: 357-367.
Lagudah et al. (2006) Theor. and Appl. Genet. 114: 21-30.
Langridge et al. (2001) Aust. J. Agric. Res. 52: 1043-1077.
Lemieux (2000) Current Genomics 1: 301-311.
Liang et al. (2006) Phytopathology 96:784-789.
Lu et al. (1993) J. Exp. Med. 178:2089-2096.
Matsuoka et al. (1993) Proc. Natl. Acad. Sci. USA 90:9586-9590.
McIntosh (1992) Plant Pathol. 41:523-527.
Medberry et al. (1992) Plant Cell 4: 185-192.
Medberry et al. (1993) Plant J. 3: 619-626.
Needleman and Wunsch (1970) J. Mol. Biol. 45:443-453.
Niedz et al. (1995) Plant Cell Reports 14: 403-406.
Orozco et al. (1993) Plant Mol. Biol. 23:1129-1138.
Ow et al. (1986) Science 234: 856-859.
Pellegrineschi et al. (2002) Genome 45:421-430.
Prasher et al. (1985) Biochem. Biophys. Res. Comm. 126: 1259-68.
Rae (2007) Annu Rev. Plant Biol. 58:347-375.
Rogers et al (2001) J. Mol. Microbiol. Biotechnol. 3: 207-214.
Rubiales and Niks (1995) Plant Dis. 79:1208-1212.
Salomon et al. (1984) EMBO J. 3: 141-146.
Schunmann et al. (2003) Functional Plant Biology 30:453-460.
Singh (1992a) Phytopathology 82: 835-838.
Singh (1992b) Crop Science 32: 874-878.
Singh and Rajaram (1994) Euphytica 72: 1-7.
Slade and Knauf (2005) Transgenic Res. 14: 109-115.
Spielmeyer et al. (2002) Theor. Appl. Genet. 116, 481-490.
Spielmeyer et al. (2005) Theor. Appl. Genet. 111: 731-735.
Spielmeyer et al. (2008) Theor Appl Genetics 116: 481-490.
Stalker et al. (1988) Science 242:419-423.
Stein et al. (2006) The Plant Cell 18: 731-746.
Stockhaus et al. (1987) Proc. Natl. Acad. Sci. USA 84:7943-7947.
Stockhaus et al. (1989) EMBO J. 8:2445-2451.
Thillet et al. (1988) J. Biol. Chem. 263:12500.
Toriyama et al. (1986) Theor. Appl. Genet. 205:34.
van den Brule and Smart (2002) Planta 216:95-106.
Verrier et al. (2007) Trends Plant Sci. 13:151-159.
Wagner et al. (1992) Proc. Natl. Acad. Sci. USA 89:6099-6103.
Yamamoto et al. (1994) Plant Cell Physiol. 35: 73-778.
Yamamoto et al. (1997) Plant J. 1:255-265.

The invention claimed is:

1. A transgenic cereal plant which has integrated into its genome an exogenous polynucleotide encoding an Lr34 adult plant pathogen resistance polypeptide comprising an amino acid sequence at least 95% identical to the amino acid sequence set forth as SEQ ID NO:1, wherein the adult plant pathogen resistance polypeptide provides enhanced resistance to a plant pathogen when compared to an isogenic cereal plant lacking the exogenous polynucleotide, and wherein the pathogen is one or more of the following pathogens: *Bipolaris sorokiniana, Erysiphe graminis* f. sp. *tritici, Puccinia graminis* f. sp. *tritici, Puccinia striiformis* and *Puccinia recondite* f. sp. *tritici.*

2. The transgenic cereal plant of claim 1 wherein the plant is a wheat plant.

3. The transgenic cereal plant of claim 1, wherein the amino acid sequence of the Lr34 adult plant pathogen resistance polypeptide is at least 98% identical to the amino acid sequence set forth as SEQ ID NO:1.

4. The transgenic cereal plant of claim 1, wherein the amino acid sequence of the Lr34 adult plant pathogen resistance polypeptide comprises the amino acid sequence set forth as SEQ ID NO:1.

5. The transgenic cereal plant of claim 4 wherein the plant is a wheat plant.

6. A transgenic cereal seed which has integrated into its genome an exogenous polynucleotide encoding an Lr34 adult plant pathogen resistance polypeptide comprising an amino acid sequence at least 95% identical to the amino acid sequence set forth as SEQ ID NO:1, wherein the adult plant pathogen resistance polypeptide provides enhanced resistance to a cereal plant produced from the seed to a plant pathogen when compared to an isogenic cereal plant lacking the exogenous polynucleotide, and wherein the pathogen is one or more of the following pathogens: *Bipolaris sorokiniana, Erysiphe graminis* f. sp. *tritici, Puccinia graminis* f. sp. *tritici, Puccinia striiformis* and *Puccinia recondita* f. sp. *tritici.*

7. The transgenic cereal seed of claim 6 wherein the seed is a wheat seed.

8. The transgenic cereal seed of claim 6, wherein the amino acid sequence of the Lr34 adult plant pathogen resistance polypeptide is at least 98% identical to the amino acid sequence set forth as SEQ ID NO:1.

9. The transgenic cereal seed of claim 6, wherein the amino acid sequence of the Lr34 adult plant pathogen resistance polypeptide comprises the amino acid sequence set forth as SEQ ID NO:1.

10. The transgenic cereal seed of claim 9 wherein the seed is a wheat seed.

11. A method of producing a transgenic cereal plant which has integrated into its genome an exogenous polynucleotide encoding an Lr34 adult plant pathogen resistance polypeptide comprising an amino acid sequence at least 95% identical to the amino acid sequence set forth as SEQ ID NO:1, the method comprising i) introducing said exogenous polynucleotide encoding the Lr34 adult plant pathogen resistance polypeptide into a cereal plant cell, wherein the polynucleotide is operably linked to a promoter, and ii) generating a transgenic cereal plant from the cell, thereby producing the transgenic cereal plant, wherein the adult plant pathogen resistance polypeptide provides enhanced resistance to the plant to a plant pathogen when compared to an isogenic cereal plant lacking the exogenous polynucleotide, and wherein the pathogen is one or more of the following pathogens: *Bipolaris sorokiniana, Erysiphe graminis* f. sp. *tritici, Puccinia graminis* f. sp. *tritici, Puccinia striiformis* and *Puccinia recondita* f. sp. *tritici.*

12. The method of claim 11, wherein the cereal plant is a wheat plant.

13. The method of claim 11, wherein the amino acid sequence of the Lr34 adult plant pathogen resistance polypeptide is at least 98% identical to the amino acid sequence set forth as SEQ ID NO:1.

14. The method of claim 11, wherein the amino acid sequence of the Lr34 adult plant pathogen resistance polypeptide comprises the amino acid sequence set forth as SEQ ID NO:1.

15. The method of claim 14, wherein the cereal plant is a wheat plant.

16. A method of producing a transgenic cereal plant part which has integrated into its genome an exogenous polynucleotide encoding an Lr34 adult plant pathogen resistance polypeptide comprising an amino acid sequence at least 95% identical to the amino acid sequence set forth as SEQ ID NO:1, the method comprising, a) growing the transgenic cereal plant of claim 1, and b) harvesting a transgenic cereal plant part from the plant.

17. The method of claim 16, wherein the cereal plant is a wheat plant.

18. The method of claim 16, wherein the amino acid sequence of the Lr34 adult plant pathogen resistance polypeptide is at least 98% identical to the amino acid sequence set forth as SEQ ID NO:1.

19. The method of claim 16, wherein the amino acid sequence of the Lr34 adult plant pathogen resistance polypeptide comprises the amino acid sequence set forth as SEQ ID NO:1.

20. The method of claim 19, wherein the cereal plant is a wheat plant.

* * * * *